(12) United States Patent
Olejnik et al.

(10) Patent No.: US 7,145,019 B2
(45) Date of Patent: Dec. 5, 2006

(54) PHOTOCLEAVABLE ISOTOPE-CODED AFFINITY TAGS

(75) Inventors: Jerzy Olejnik, Brookline, MA (US); Kenneth J. Rothschild, Newton, MA (US)

(73) Assignee: Ambergen, Inc., Waltham, MA (US)

( * ) Notice: Subject to any disclaimer, the term of this patent is extended or adjusted under 35 U.S.C. 154(b) by 56 days.

(21) Appl. No.: 10/687,297

(22) Filed: Oct. 16, 2003

(65) Prior Publication Data
US 2005/0085630 A1 Apr. 21, 2005

(51) Int. Cl.
*C07D 495/04* (2006.01)
(52) U.S. Cl. .................................. 548/304.1
(58) Field of Classification Search .............. 548/304.1
See application file for complete search history.

(56) References Cited

U.S. PATENT DOCUMENTS 5,219,764 A * 6/1993 Huber et al. ................ 436/536
6,852,544 B1 * 2/2005 Aebersold et al. .......... 436/173

OTHER PUBLICATIONS

Pandori et al., Chemistry & Biology, vol. 9, 567-573, May 2002.*

Kumar et al., Organic Letters, vol. 5, No. 5, pp. 613-616, Oct. 7, 2002.*

\* cited by examiner

*Primary Examiner*—Kamal A. Saeed
*Assistant Examiner*—Susannah L. Chung
(74) *Attorney, Agent, or Firm*—Medlen & Carroll, LLP

(57) ABSTRACT

This invention relates to agents and conjugates that can be used to detect and isolate target components from complex mixtures such as proteins and protein fragments from biological samples from in vivo and in vitro sources. Agents comprise a detectable group bound to a photoreactive group. Conjugates comprise agents coupled to substrates by covalent bounds which can be selectively cleaved with the administration of electromagnetic radiation. Targets substances labeled with detectable molecules can be easily identified and separated from a heterologous mixture of substances. Exposure of the conjugate to radiation releases the target in a functional form and completely unaltered. Using photocleavable molecular precursors as the conjugates, label can be incorporated into macromolecules, the nascent macromolecules isolated and the label completely removed. The invention also relates to targets isolated with these conjugates which may be useful as pharmaceutical agents or compositions that can be administered to humans and other mammals.

12 Claims, 39 Drawing Sheets

Step 1: Synthesis of Photocleavable Biotin
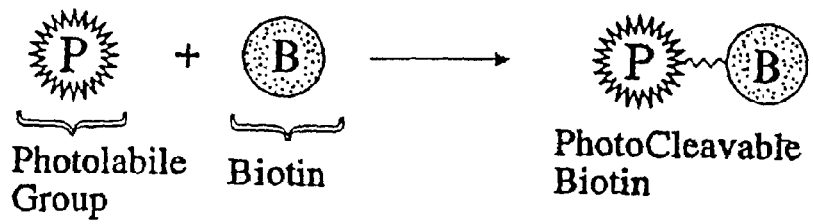
Photolabile Group   Biotin   PhotoCleavable Biotin
Step 2: Modification of the substrate by Photocleavable Biotin
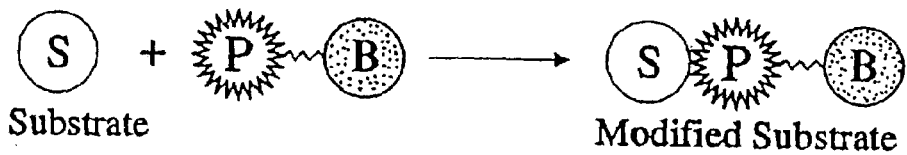
Substrate   Modified Substrate
Step 3: Isolation of the Modified Substrate using Avidin
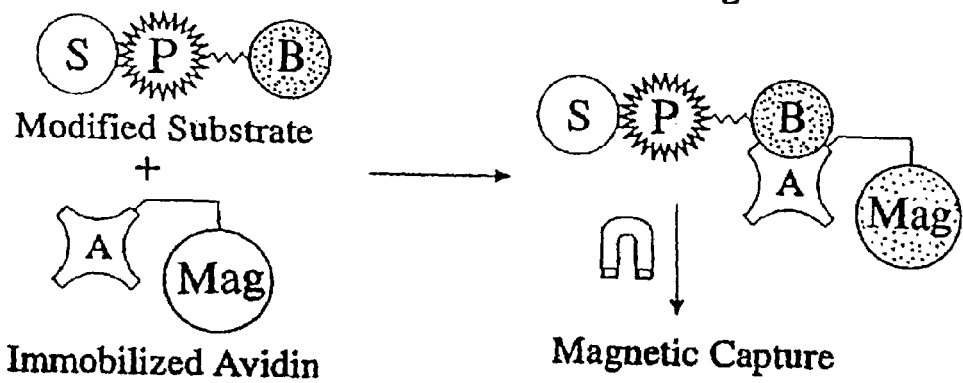
Modified Substrate
+
Immobilized Avidin
Magnetic Capture
Step 4: Detachment of Pure Substrate
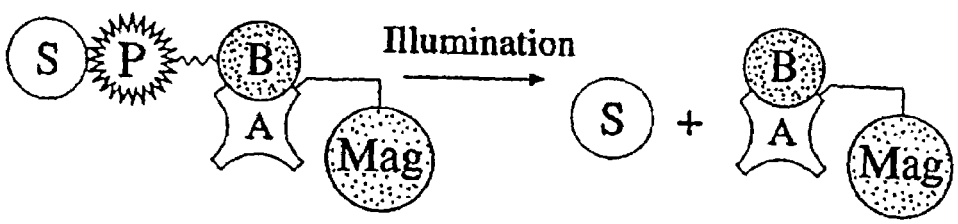
Illumination
Figure 9

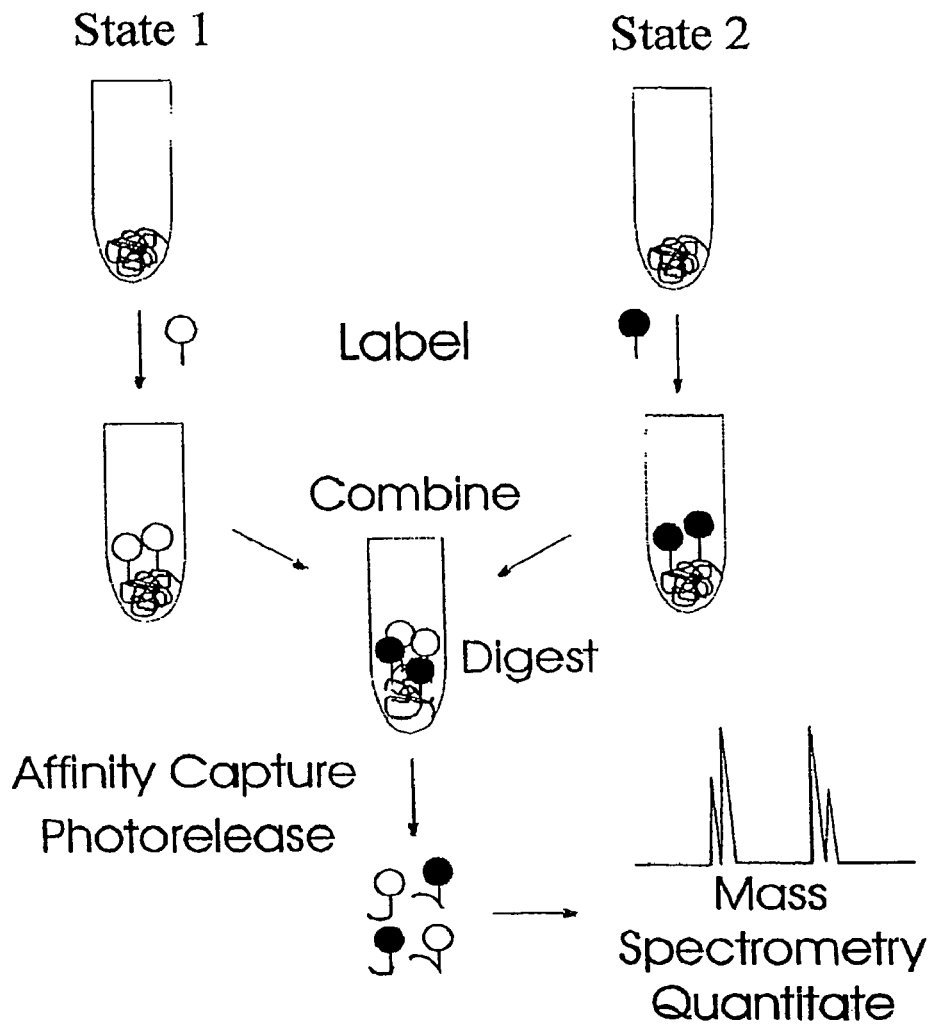
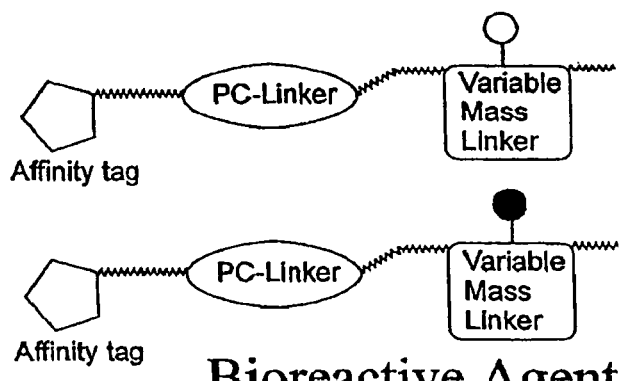
Figure 10

Figure 14E
| PC-ICAT Reagent | Reactive Group (Reactivity) | Mass change (after cleavage) |
|---|---|---|
| PC-ICAT #1 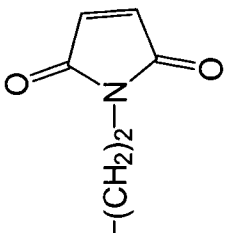 | Maleimide (Sulfhydryls) | 297.3 |
| PC-ICAT #2 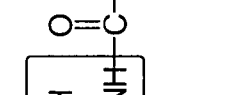 | Iodocetamide (Sulfhydryls) | 186.2 |
| PC-ICAT #3 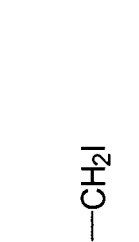 | NHS ester (Amines) | 242.3 |

Figure 20

| Analyte | Mass calculated (MH)⁺ | Mass measured (solution) | Mass measured (Streptavidin beads) |
|---|---|---|---|
| Reagent PC-ICAT#1 | 976.41 (uncleaved); 635.28 (cleaved) | 976.94; 635.66 | N/a |
| SV-40 peptide analog | 1378.69; 2755.38 (homodimer) | 2755.06 (homodimer); 1378.74; | N/a |
| SV-40 peptide analog+ PC-ICAT#1 | 2355.1 (uncleaved); 1676.0 (cleaved) | 2755.53 (homodimer) 2355.36; 1675.98; 1378.36 | Streptavidin beads: 2355.45; 1676.33; Photocleaved/supernatant: 1676.23 |
| HIV gp120 peptide | 2721.30 | 2721.52; 1361.14 $(MH_2)^{+2}$ | N/a |
| HIV gp120 peptide + PC-ICAT#1 | 3697.71 (uncleaved) 3018.61 (cleaved) | 3697.09; 3018.82; 2721.45; 1849.13 (uncleaved $(MH_2)^{2+}$); 1509.18 (cleaved, $MH_2)^{2+}$); 1360.88 $(MH_2)^{+2}$ | Streptavidin beads: 3697.13; 3018.62; Cleaved/supernatant: 3018.89 |

Figure 25

| Peptide | H:L ratio (theory) | H:L ratio (experiment) | Standard Deviation | Error, [%] |
|---|---|---|---|---|
| HIV gp120 | 1 | 1.4898 | 0.126 | 48.0 |
| | 0.50 | 0.7838 | 0.038 | 56.0 |
| | 0.20 | 0.2403 | 0.004 | 20.0 |
| | 0.10 | 0.1579 | 0.043 | 9.0 |
| SV40 | 1 | 1.0593 | 0.019 | 6.0 |
| | 2 | 1.9220 | 0.024 | 4.0 |
| | 5 | 3.7449 | 0.362 | 25.0 |
| | 10 | 5.7204 | 0.250 | 56.0 |

| # | Rank/Sp | (M+H)+C*10^4 | | Ions | Reference | Peptide |
|---|---------|--------------|--------|-------|-----------|---------|
| 1. | 1/ 1 | 1994.3 | 4.4675 | 17/26 | G3P_RABIT | (R)VPTPNVSVVDLTC#R (SEQ ID NO:60) |
| 2. | 2/ 403 | 1995.1 | 2.7366 | 13/34 | SLTRNGL | (E)LGKPVLTANQVTIWEGLR (SEQ ID No:61) |
| 3. | 3/ 3 | 1995.0 | 2.6591 | 16/36 | FLP_LACCA | (N)LANPNVYTETLTAATVCTI (SEQ ID NO:62) |
| 4. | 4/ 209 | 1995.0 | 2.6335 | 14/36 | A42912 | (Y)LALLPSDAEGPHGQFVTDK (SEQ ID NO:63) |
| 5. | 5/ 381 | 1995.1 | 2.4634 | 13/38 | H69373 | (L)ALLVLVAPAMAAGNGEDLRN (SEQ ID NO:64) |

Figure 27B

PHOTOCLEAVABLE ISOTOPE-CODED AFFINITY TAGS

FIELD OF THE INVENTION

This invention relates to agents and conjugates used in the detection and isolation of targets from heterologous mixtures in combination with isotope-coded affinity tags. Agents comprise, for example, an affinity moiety (e.g. capable of binding to a capture reagent) attached via a first linker to a photoreactive group, which is in turn attached via a second linker to a protein reactive group. In addition, the agents of the present invention may comprise one or more detectable moieties or groups. Conjugates comprise agents which are coupled to substrates by one or more covalent bonds. These bonds can be easily and selectively photocleaved with the application of electromagnetic radiation. Substrates which may be coupled to agents include amino acids, peptides, proteins and protein fragments. The invention also relates to rapid and efficient methods for the detection and isolation of targets, such as cells and proteins, and to kits which contain these components.

BACKGROUND

With the completion of an increasing number of genomic sequences, attention is currently focused on how the data contained in sequence databases might be interpreted in terms of the structure, function and control of biological systems. Approaches for global profiling of gene expression at the mRNA level as a function of the cellular state have been developed (DeRisi, et al., Science 278:680–686, 1997; Roth, et al., Nat. Biotechnol, 16:939–945, 1998; Velculescu, et al., Cell, 88:243–251, 1997) and are widely used to identify clusters of genes for which the expression is idiotypic for a specific state. These methods, though exquisitely sensitive, do not indicate changes in protein expression. Quantitative proteome analysis, the global analysis of protein expression, is a complementary method to study steady-state gene expression and perturbation-induced changes. In comparison to gene expression analysis at the mRNA level, proteome analysis provides more accurate information about biological systems and pathways because the measurement directly focuses on the actual biological effector molecules.

Most approaches to quantitative protein analysis are accomplished by combining protein separation, most commonly by high-resolution two-dimensional polyacryamide gel electrophoresis (2D-PAGE), with mass spectrometry (MS)-based or tandem mass spectrometry (MS/MS)-based sequence identification of selected, separated protein species (Link, et al., Electrophoresis, 18:1314–1334, 1997; Shevchenko, et al., PNAS, USA, 93:14440–14445, 1996; Gygi, et al., Mol Cell Biol, 19:1720–1730, 1999; Garreis, et al., Electrophoresis, 18:1347–1360, 1997; Boucheria, et al., Electrophoresis, 17:1683–1699, 1996). This method is sequential, labor intensive and difficult to automate. In addition, it selects against specific classes of proteins, such as membrane proteins, very large and very small proteins and extremely acidic or basic proteins. However, the techniques most significant flaw lies in its bias towards highly abundant proteins, as lower abundant regulatory proteins (e.g., transcription factors, protein kinases, etc.) are rarely detected when total cell lysates are analyzed. (Link, et al., Electrophoresis, 18:1314–1334, 1997; Shevchenko, et al., PNAS, USA, 93:14440–14445, 1996; Gygi, et al., Mol Cell Biol, 19:1720–1730, 1999; Garreis, et al., Electrophoresis, 18:1347–1360, 1997; Boucheria, et al., Electrophoresis, 17:1683–1699, 1996).

The development of methods and instrumentation for automated, data-dependent electrospray ionization (ESI) MS/MS, in conjunction with microcapillary liquid chromatography (mLC) and database searching, has significantly increased the sensitivity and speed for the identification of gel-separated proteins. Moreover, mLC-MS/MS has also been used successfully for the large-scale identification of proteins directly from mixtures without gel electrophoretic separation (Link, et al., Nat Biotechnol, 17:676–682, 1999; Opiteck, et al., Anal Chem, 69:1518–1524, 1997). These analyses, though fast and easily automated, are not quantitative and are also incompatible with the analysis of low-abundance proteins. Thus, there is a great need for a general and quantitative technology for proteome analysis.

One recent development in proteome analysis is the use of a technology called isotope-coded affinity tag (ICAT). However, this technology suffers from an inherent problem whereby steric hindrance caused by the tag often interferes with downstream processing and analysis of the identified and/or isolated protein or protein fragment.

Unfortunately, an easy to use method for the tagging, detection and characterization of molecules that does not have the shortcomings of the prior art methods (e.g., stearic hindrance, radioactivity, and undue complexity of use) is not available. Therefore, what is needed is a novel method for whereby proteins and proteins fragments can be isolated and identified without the interference of stearic hindrance and other prior art problems before any downstream analysis and processing.

SUMMARY OF THE INVENTION

The present invention overcomes the problems and disadvantages associated with current strategies and designs and provides new methods for the detection and isolation of molecules from complex mixtures as well as problems inherent in more current technologies such as isotope-coded affinity tag (ICAT) procedures (detailed in U.S. Patent Application No. US 2002/0076739 A1 and incorporated herein by reference).

One embodiment of the invention is directed to bioreactive agents comprising a detectable group bonded to a photoreactive group wherein the photoreactive group contains at least one group capable of covalently bonding to a substrate to form a conjugate that can be selectively photocleaved to release said substrate. In one embodiment, detectable groups have a selectively detectable physical property such as fluorescence, absorption or an ability to specifically bind to a coupling agent such as avidin or streptavidin, antibodies, antigens or binding proteins. In one embodiment, the bioreactive agent does not comprise a detectable group. In a preferred embodiment, the detectable group comprises stable isotopes so as to form part of a differentially isotopically labeled reagent.

In one embodiment, it is contemplated that the detectable group is bound to the bioreactive reagent or a portion of the bioreactive agents of the present invention are altered or function as a detectable group. In another embodiment, the detectable group or element is part of a linker, such as the linker which links the photoreative group with a protein reactive group.

The photoreactive group should be capable of forming one or more covalent bonds with a chemical group of a substrate or other reagents comprising the bioreactive agent.

Those covalent bonds may be photocleaved with electromagnetic radiation releasing the substrate or the substrate and a portion of the bioreactive reagent, depending on the arrangement of the various groups of the bioreactive reagent.

In a first particular embodiment, the present invention contemplates a compound of the general formula:

A-L-PR-AL-PRG wherein A is an affinity moiety (which may also function as, or be bound to, a detectable group) which binds to a capture reagent, L is a first linker that is not labeled with stable isotopes (although it may comprise other detectable groups), PR is a photoreactive group, AL is a second linker comprising one or more —H$_2$C—NH— groups, wherein said second linker is labeled with one or more stable isotopes, and PRG is the protein reactive group that reacts with functional groups on proteins, polypeptides and peptides (and amino acids if desired). In one embodiment, said second linker comprises a structure of the general formula: —HN—(CH$_2$)n-NH— wherein n is a whole number between 1 and 10. In a particular embodiment, said second linker comprises a structure derived from a diamine, wherein said diamine is selected from the group consisting of 1,3 diaminopropane, 1,4-diaminobutane, 1,5-diaminopentane, 1,6-diaminohexane, 1,7-diaminoheptane, 1,8-diaminooctane and 2,2-(Ethylenedioxy)-diethylamine. By derived from a diamine it is meant that the reactant used to make the linker is a diamine, with the understanding that the linker produced may reflect modifications to the structure of the diamine (e.g. lacking one or more hydrogens and/or amino groups). In yet another embodiment, said second linker comprises a structure of the general formula: —HN—(CH$_2$—CH$_2$—O)$_n$—CH$_2$—CH$_2$—NH— wherein n is a whole number between 1 and 10.

It is not intended that the present invention be limited to a particular affinity moiety. A variety of affinity moieties are contemplated. Typically, the affinity moiety is contemplated in the context of a particular capture reagent. In other words, it is preferred that affinity moieties are chosen for their high affinity for a particular capture reagent. In preferred embodiments of the compounds and methods of the present invention, said affinity moiety comprises biotin (e.g. a biotinyl group). Similarly, it is not intended that the present invention be limited to a particular protein reactive group. A variety are contemplated. In one embodiment, said protein reactive group is a sulfhydryl reactive group. In another embodiment said protein reactive group is an amine reactive group. In a second particular embodiment, the present invention contemplates a photocleavable compound having the general formula:

A-L-PR-AAL-PRG wherein A is an affinity moiety that binds to a capture reagent; L is a first linker that is not labeled with stable isotopes; PR is a photocleavable group, AAL is a second linker comprising one or more amino and carboxyl groups (and in a preferred embodiment, comprises a structure derived from an amino acid), said second linker labeled with one or more stable isotopes; and PRG is a protein reactive group that reacts with functional groups on proteins, polypeptides, and peptides (and amino acids if desired). In one embodiment where said second linker comprises a structure derived from an amino acid, the amino acid is selected from the group consisting of valine, leucine, and isoleucine. In one embodiment, the structure derived from an amino acid is linked to said photocleavable group through an alpha-amino group and linked to said protein reactive group through an alpha-carboxyl group. In another embodiment, the structure derived from an amino acid (e.g. valine, leucine, and isoleucine) is linked to said protein reactive group through an alpha-amino group and linked to said photocleavable group through an alpha-carboxyl group. In a particular embodiment, said second linker comprises a structure derived from lysine, wherein said structure is linked to said photocleavable group through an alpha-amino group and linked to said protein reactive group through an alpha-amino group. In another embodiment where said second linker comprises a structure derived from lysine, said amino acid structure is linked to said protein reactive group through an alpha-amino group and linked to said photocleavable group through an alpha-amino group. By derived from an amino acid it is meant that the reactant used to make the linker is an amino acid (whether common, rare, naturally occurring or synthetic), with the understanding that the reaction to make the linker may modify the number of hydrogens on the amino group (for example) or remove the hydroxyl group of the carboxyl group of the amino acid. In one embodiment, said second linker is of the general formula:

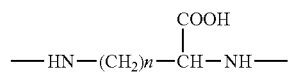

wherein n is a whole number between 1 and 10. In another embodiment, said second linker is of the general formula:

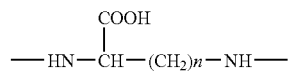

wherein n is a whole number between 1 and 10. Again, it is not intended that the invention be limited to any particular protein reactive group. In one embodiment, said protein reactive group is a sulfhydryl reactive group or an amine reactive group.

In a third particular embodiment, the present invention contemplates a photocleavable compound having the general formula:

A-L-PR-AAL-AL PRG wherein A is an affinity moiety that binds to a capture reagent; L is a first linker that is not labeled with stable isotopes; PR is a photocleavable group; AAL is a second linker comprising one or more amino and carboxyl groups (and in a preferred embodiment, comprises a structure derived from an amino acid), said second linker labeled with one or more stable isotopes; AL is a third linker comprising one or more —H$_2$C—NH— groups (and in a preferred embodiment, comprises a structure derived from a diamine); and PRG is a protein reactive group that reacts with functional groups on proteins, polypeptides, and peptides (and amino acids if desired). In one embodiment, the AAL-AL portion is of the general formula:

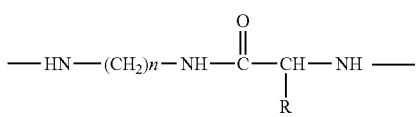

In a fourth particular embodiment, the present invention contemplates a photocleavable compound having the general formula:

A-L-PR-AL-AAL-PRG wherein A is an affinity moiety that binds to a capture reagent; L is a first linker that is not labeled with stable isotopes; PR is a photocleavable group; AL is a second linker comprising one or more —H$_2$C—NH— groups (and in a preferred embodiment, comprises a structure derived from a diamine); AAL is third linker comprising one or more amino and carboxyl groups (and in a preferred embodiment, comprises a structure derived from an amino acid), said structure labeled with one or more stable isotopes; and PRG linkers) are given in FIGS. 12, 13 and 14A–F (the present invention is not limited to the examples shown in the specification or in the Figures). Functionally, the first linker is designed to link the functional groups of the compound in a manner whereby there is sufficient spacing to avoid interference (e.g. steric hindrance and the like). The first linker is also designed, in preferred embodiments, to contribute to the solubility of the entire compound.

It should be noted that, when considering the general formulas described above as well as the compounds depicted below and in the figures, the present invention contemplates that one or more protecting groups may be added to avoid certain interactions. For example, in each case described above, the protein reactive group may contain removable protecting groups so as to control when (in a particular method) the protein reactive group reacts. Moreover, the term protein reactive group is meant to imply groups reactive with amino acids, peptides, and polypeptides, as well as proteins.

In a particularly preferred embodiment, the present invention contemplates a photocleavable compound having the general formula:

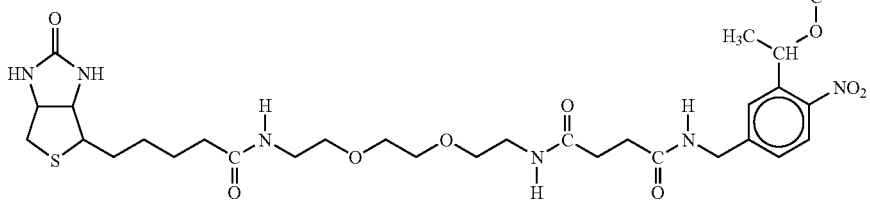

is a protein reactive group that reacts with functional groups on proteins, polypeptides, and peptides (and amino acids if desired). In one embodiment, the AL-AAL portion is of the general formula:

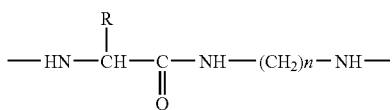

In the various preferred embodiments, it is not intended that the present invention be limited to a particular type of first linker. The first linker may be linear or branched. A linear first linker may be up to fifty atoms in length, but more preferably, less than thirty atoms in length, and still more preferably, less than twenty-five atoms in length (but preferably more than eight atoms in length). The linker may contain primarily carbon-carbon linkages, but more preferably one or more C—O—C— linkages, as well as other types of atoms in the chain (e.g. N or S). Examples of compounds of the present invention (with various first wherein R is an aliphatic hydrocarbon chain; wherein the portion defined by

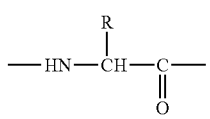

comprises one or more stable isotopes; and PRG is a protein reactive group that reacts with functional groups on proteins, polypeptides, peptides and amino acids. Again, it is not intended that the present invention be limited to a particular protein reactive group. In one embodiment, said protein reactive group is a sulfhydryl reactive group or an amine reactive group. It is also not intended that the present invention be limited to the length or nature of R; in one embodiment said aliphatic hydrocarbon chain is greater than two carbons in length (but preferably less than ten carbons in length) and said aliphatic hydrocarbon chain is branched (although linear embodiments are also contemplated).

In still another particularly preferred embodiment, the present invention contemplates a photocleavable compound having the general formula:

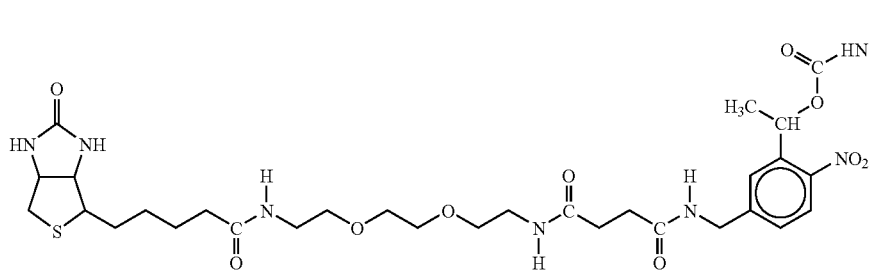

wherein R is an aliphatic hydrocarbon chain; wherein the portion defined by

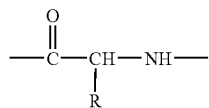

comprises one or more stable isotopes; and PRG is a protein reactive group that reacts with functional groups on proteins. (n=between 1 and 10).

Again, it is not intended that the present invention be limited to a particular type of protein reactive group. In one embodiment, said protein reactive group is a sulfhydryl reactive group or an amine reactive group. Again, the R group can be of various lengths and types; in one embodiment, said aliphatic hydrocarbon chain is greater than two carbons in length (but preferably less than ten carbons in length) and said aliphatic hydrocarbon chain is branched (although linear embodiments are also contemplated).

In yet another particularly preferred embodiment, the present invention contemplates a photocleavable compound having the general formula:

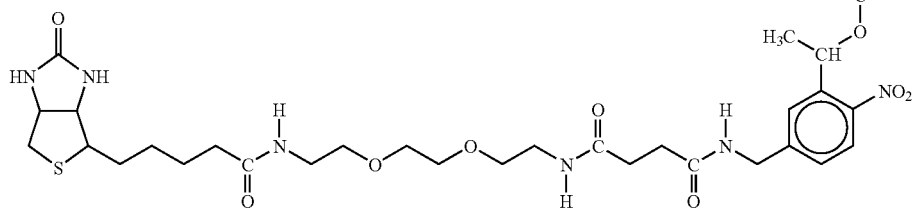

wherein x is a whole number between 1 and 10; wherein the portion defined by:

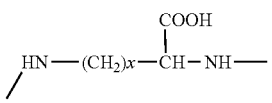

comprises one or more stable isotopes; and PRG is a protein reactive group that reacts with functional groups on proteins.

Again, it is not intended that the present invention be limited to a particular type of protein reactive group. In one embodiment, said protein reactive group is a sulfhydryl reactive group or an amine reactive group.

In still another particularly preferred embodiment, the present invention contemplates a photocleavable compound having the general formula:

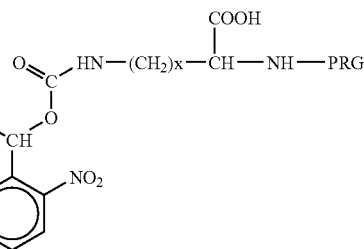

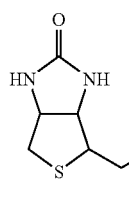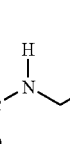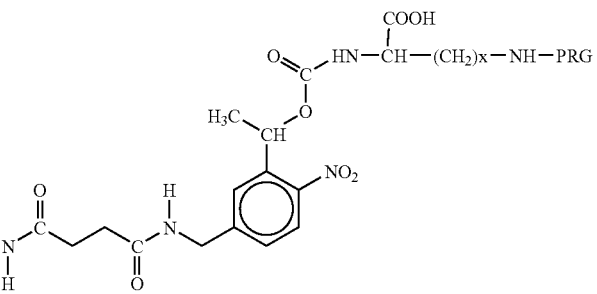

wherein x is a whole number between 1 and 10; wherein the portion defined by

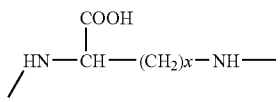

comprises one or more stable isotopes; and PRG is a protein reactive group that reacts with functional groups on proteins.

While many of the above-described embodiments have second linkers comprising amino groups, the present invention also contemplates second linkers lacking amino groups. In one embodiment, the present invention contemplates second linkers derived from dicarboxylic acids (e.g. malonic acid, succinic acid, glutaric acid, adipic acid, pimelic acid, suberic acid, azelaic acid, and sebacic acid, etc.). In one embodiment, said second linker comprises a structure of the general formula:

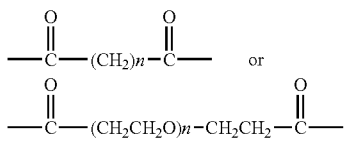

wherein n is a whole number between 1 and 10.

The compounds described herein can be made in a variety of ways using a variety of synthesis schemes. In one embodiment, the present invention contemplates a first method, comprising: a) providing i) a diamine; and ii) a photocleavable biotin-NHS (PC-Biotin-NHS); and b) reacting said diamine with said PC-Biotin-NHS under conditions such that a first product is generated of the general formula:

Biotin-L-PR-AL wherein L is a first linker that is not labeled with stable isotopes; PR is a photocleavable group, and AL is a second linker comprising one or more —H$_2$C—NH— groups. In one embodiment, the method further comprises c) reacting said first product with a compound comprising an amino acid structure (e.g. comprising one or more amino groups and carboxylic groups) so as to generate a second product of the general formula:

Biotin-L-PR-AL-AAL wherein AAL is a third linker comprising a structure derived from an amino acid. In a preferred embodiment, said second linker is labeled with one or more stable isotopes. In another embodiment, said third linker is labeled with one or more stable isotopes. In one embodiment of this first method, said diamine is of the general formula:

In a particular embodiment of this first method, said diamine is selected from the group consisting of 1,3-diaminopropane, 1,4-diaminobutane, 1,5-diaminopentane, 1,6-diamino-hexane, 1,7-diaminoheptane, 1,8-diaminooctane and 2,2' (Ethylenedioxy) diethylamine.

In yet another embodiment of this first method, said diamine is of the general formula:

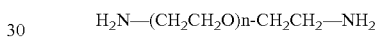

wherein n is a whole number between 1 and 10. Moreover, in this first method, a variety of PC-Biotin-NHS compounds are contemplated. For example, in one embodiment, said PC-Biotin-NHS compound is selected from the group of compounds shown in FIG. 1. In another embodiment, the PC-Biotin-NHS compounds are modified from those shown in FIG. 1 such that the linker —(—CH$_2$)$_4$—CO—NH—CH$_2$— is replaced with longer linkers, whether linear or branched. The linker may be up to fifty atoms in length, but more preferably, less than thirty atoms in length, and still more preferably, less than twenty-five atoms in length, and most preferably less than twenty atoms in length (but preferably more than eight atoms in length). The linker may contain primarily carbon-carbon linkages, but more preferably one or more C—O—C— linkages, as well as other types of atoms in the chain (e.g. N or S). Again, reference to figures other than FIG. 1 provide examples of compounds with a variety of linkers.

In particular embodiments of this first method (see above), the present invention contemplates that the AL-AAL portion is of the general formula:

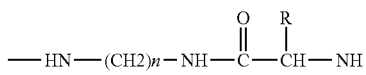

wherein n is a whole number between 1 and 10.

The present invention contemplates, in another embodiment, a second method, comprising: a) providing i) a compound comprising an amino acid structure (e.g. comprising one or more amino groups and carboxylic groups), and ii) PC-Biotin-NHS; and b) reacting said compound with said PC-Biotin-NHS under conditions such that a first product is generated of the general formula:

Biotin-L-PR-AAL wherein L is a first linker that is not labeled with stable isotopes; PR is a photocleavable group, and AAL is a second linker comprising a structure derived from an amino acid. Once again, the present invention contemplates embodiments where there are additional steps in the synthesis. In one such embodiment, the method further comprises c) reacting said first product with a diamine so as to generate a second product of the general formula:

Biotin-L-PR-AAL-AL wherein AL is a third linker comprising one or more —H$_2$C—NH— groups. It is contemplated that these structures can contain one or more stable isotopes. In one embodiment, said second linker is labeled with one or more stable isotopes. In another embodiment, said third linker is labeled with one or more stable isotopes.

In one embodiment of this second method, said compound is selected from the group consisting of valine, leucine, and isoleucine, wherein said amino acid structure is linked to said photocleavable group through an alpha-amino group and linked to said protein reactive group through an alpha-carboxyl group. In another embodiment, said compound is selected from the group consisting of valine, leucine, and isoleucine, wherein said amino acid structure is linked to said protein reactive group through an alpha-amino group and linked to said photocleavable group through an alpha-carboxyl group. In still another embodiment, said compound comprises lysine, wherein said amino acid structure is linked to said photocleavable group through an alpha-amino group and linked to said protein reactive group through an alpha-amino group. In yet another embodiment, said compound comprises lysine, wherein said amino acid structure is linked to said protein reactive group through an alpha-amino group and linked to said photocleavable group through an alpha-amino group.

In embodiments of this second method, said second linker can be of the general formula:

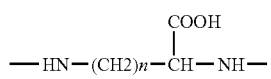

wherein n is a whole number between 1 and 10. In other embodiments, said second linker is of the general formula

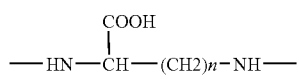

wherein n is a whole number between 1 and 10. In other embodiments, the AAL-AL portion is of the general formula:

wherein n is a whole number between 1 and 10.

In some embodiments, the bioreactive agent may have a chemical structure selected from molecules shown in FIGS. 12 (compound 8), 13 (compound 7), 14A (compound 4), 14B (compound 4), 14C (compound 4) and 14D (compound 4), as well as those represented by the formula:

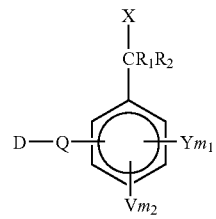

wherein X is selected from the group consisting of a halogen, N$_2$, CH$_2$-halogen, —N=C=O, —N=C=S, —S—S—R, NC$_2$H$_4$, —NC$_4$H$_2$O$_2$, —OH, —NHNH$_2$, —OP(OR3)N(R4)R5 and —OCO-G, wherein G is selected from the group consisting of a halogen, N$_3$, O-esters and N-amides; $R_1$, $R_2$, $R_3$, $R_4$ and $R_5$ are selected from the group consisting of hydrogen, alkyls, substituted alkyls, aryls and substituted aryls, —CF$_3$, —NO$_2$, —COOH and —COOR, and may be the same or different; A is a divalent functional group selected from the group consisting of —O—, —S— and —NR$_1$; Y comprises one or more polyatomic groups which may be the same or different; V comprises one or more optional monoatomic groups which may be the same or different; Q comprises an optional spacer group; m1 and m2 are integers from 0–5 and may be the same or different; and D comprises a detectable group which is distinct from R1–R5.

Another embodiment of the invention is directed to conjugates (a conjugate is a bioreactive agent of the present invention coupled to a substrate) comprising a bioreactive agent photocleavably coupled to a substrate wherein said agent comprises a detectable group bonded to a photoreactive group, wherein said conjugate can be selectively cleaved with electromagnetic radiation to release said substrate. Suitable substrates which can be coupled to the bioreactive agent include proteins, peptides, amino acids, amino acid analogs, nucleic acids, nucleosides, nucleotides, lipids, vesicles, detergent micells, cells, virus particles, fatty acids, saccharides, polysaccharides, inorganic molecules, metals, and derivatives and combinations thereof. Substrates may be pharmaceutical agents such as cytokines, immune system modulators, agents of the hematopoietic system, chemotherapeutic agents, radio-isotopes, antigens, anti-neoplastic agents, recombinant proteins, enzymes, PCR products, receptors, hormones, vaccines, haptens, toxins, antibiotics, nascent proteins, cells, synthetic pharmaceuticals and derivatives and combinations thereof.

In other embodiments, conjugates may have a chemical structure selected as shown in FIGS. 12 (compound 8), 13 (compound 7), 14A (compound 4), 14B (compound 4), 14C (compound 4) and 14D (compound 4), as well as from the group consisting of:

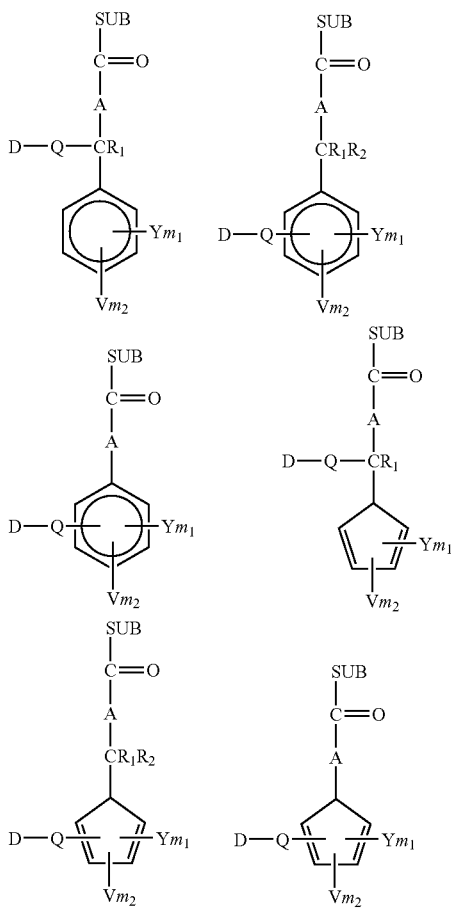

wherein SUB comprises a substrate; $R_1$ and $R_2$ are selected from the group consisting of hydrogen, alkyls, substituted alkyls, aryls, substituted aryls, —$CF_3$, —$NO_2$, —COOH and —COOR, and may be the same or different; A is a divalent functional group selected from the group consisting of —O—, —S— and —$NR_1$; Y comprises one or more polyatomic groups which may be the same or different; V comprises one or more optional monoatomic groups which may be the same or different; Q comprises an optional spacer group; m1 and m2 are integers between 1–5 which can be the same or different; and D comprises a detectable group which is distinct from $R_1$ and $R_2$.

Another embodiment of the invention is directed to pharmaceutical compositions comprising the conjugate plus a pharmaceutically acceptable carrier such as water, an oil, a lipid, a saccharide, a polysaccharide, glycerol, a collagen or a combination thereof. Pharmaceuticals may be used in the prophylaxis and treatments of diseases and disorders in humans and other mammals.

The present invention also contemplates using the synthesized compounds of the present invention in reactions designed to provide information about proteins or mixtures of proteins (polypeptides). In one embodiment, the present invention contemplates a method, comprising: a) providing i) a mixture comprising proteins, ii) a solid support, and iii) a photocleavable compound of a general formula selected from the group consisting of:

A-L-PR-AL-PRG wherein A is an affinity moiety that binds to a capture reagent; L is a first linker that is not labeled with stable isotopes; PR is a photocleavable group, AL is a second linker comprising one or more —$H_2C$—NH— groups, wherein said second linker is labeled with one or more stable isotopes; and PRG is a protein reactive group that reacts with functional groups on proteins (or polypeptides, peptides, etc.);

A-L-PR-AAL-PRG wherein A is an affinity moiety that binds to a capture reagent; L is a first linker that is not labeled with stable isotopes; PR is a photocleavable group, AAL is a second linker comprising one or more amino groups and carboxyl groups (and in a preferred embodiment, said second linker comprises a structure derived from an amino acid), said second linker labeled with one or more stable isotopes; and PRG is a protein reactive group that reacts with functional groups on proteins (or polypeptides, peptides, etc.);

A-L-PR-AAL-AL-PRG wherein A is an affinity moiety that binds to a capture reagent; L is a first linker that is not labeled with stable isotopes; PR is a photocleavable group; AAL is a second linker comprising one or more amino groups and carboxyl groups (and in a preferred embodiment, said second linker comprises a structure derived from an amino acid), said second linker labeled with one or more stable isotopes; AL is a third linker comprising one or more —$H_2C$—NH— groups; and PRG is a protein reactive group that reacts with functional groups on proteins (or polypeptides, peptides, etc.); and

A-L-PR-AL-AAL-PRG wherein A is an affinity moiety that binds to a capture reagent; L is a first linker that is not labeled with stable isotopes; PR is a photocleavable group; AL is a second linker comprising one or more —$H_2C$—NH— groups; AAL is third linker comprising one or more amino groups and carboxyl groups (and in a preferred embodiment, said second linker comprises a structure derived from an amino acid), said structure labeled with one or more stable isotopes; and PRG is a protein reactive group that reacts with functional groups on proteins (or polypeptides, peptides, etc.); b) contacting said mixture (or portion thereof) with said photocleavable compound under conditions such that a population of protein-photocleavable compound conjugates is created; c) subjecting at least a portion of said population to proteolysis so as to create a plurality of peptide-photocleavable compound conjugates; d) capturing at least a portion of said plurality of peptide-photocleavable compound conjugates on said solid support to create immobilized conjugates; and e) exposing said immobilized conjugates to electromagnetic radiation under conditions such that at least a portion of said immobilized conjugates is released from said solid support so as to create released peptides. Of course, other steps may be added to the method. For example, in one embodiment, the method further comprises f) analyzing said released peptides using mass spectrometry. It is not intended that the present invention (in any embodiments) be limited to only one type of isotope. In a preferred embodiment, said stable isotopes are selected from the $^2H$, $^{13}C$, and $^{15}N$.

The present invention contemplates a number of embodiments directed to methods for isolating targets from a heterologous mixture. Briefly, a conjugate is created by coupling a bioreactive agent to a substrate by a covalent bond which is selectively cleavable with electromagnetic radiation wherein the bioreactive agent is comprised of a photoreactive group. In other embodiments, the conjugate also comprises a detectable group. The conjugate is contacted to the heterologous mixture to couple substrate to one or more targets. The coupled conjugate is separated from the mixture and treated with electromagnetic radiation to release the substrate, and the targets isolated. This method can be used to isolate targets such as immune system modulators, cytokines, agents of the hematopoietic system, proteins, hormones, gene products, antigens, cells, toxins, bacteria, membrane vesicles, virus particles, and combinations thereof from heterologous mixtures such as biological samples, proteinaceous compositions, nucleic acids, biomass, immortalized cell cultures, primary cell cultures, vesicles, animal models, mammals, cellular and cell membrane extracts, cells in vivo and combinations thereof.

Another embodiment of the invention is directed to target molecules isolated by the above methods which may be used in pharmaceutical compositions or other compositions and mixtures for industrial applications.

Another embodiment of the invention is directed to methods for isolating targets from a heterologous mixture. A conjugate is created comprising a bioreactive agent coupled to a substrate by a covalent bond which is selectively cleavable with electromagnetic radiation, wherein said bioreactive agent is comprised of a photoreactive group and the substrate is a precursor of the target photoreactive group. In other embodiments, the conjugate also comprises a detectable group. The conjugate is contacted with the heterologous mixture to incorporate substrate into targets. The incorporated conjugate is separated from the mixture, treated with electromagnetic radiation to release the substrate, and the targets isolated. This method is useful for the detection and isolation of nascent proteins, nucleic acids and other biological substances.

Another embodiment of the invention is directed to methods for isolating targets from a heterologous mixture. A conjugate is created which is comprised of a bioreactive agent coupled to a receptor by a covalent bond which is selectively cleavable with electromagnetic radiation, wherein said bioreactive agent is comprised of a photoreactive group. In other embodiments, the conjugate also comprises a detectable group. The conjugate is contacted with the heterologous mixture to couple receptor to targets and the coupled receptor-targets separated from the mixture. The separated conjugate is treated with electromagnetic radiation to release the receptor and the targets isolated.

Another embodiment of the invention is directed to methods for isolating target cells from a heterologous mixture. A conjugate is created comprising a bioreactive agent coupled to a cell receptor by a covalent bond which is selectively cleavable with electromagnetic radiation, wherein the bioreactive agent is comprised of a photoreactive group. In other embodiments, the conjugate also comprises a detectable group. The conjugate is contacted with the heterologous mixture to couple receptor to target cells. The coupled conjugate is separated from the mixture and treated with electromagnetic radiation to release the substrate. Target cells are then easily isolated such as by automation.

Another embodiment of the invention is directed to methods for determining an in vivo half-life of a pharmaceutical in a patient. A conjugate is formed by coupling the pharmaceutical to a bioreactive agent with a covalent bond that can be selectively cleaved with electromagnetic radiation, wherein said bioreactive agent comprises a photoreactive group. In other embodiments, the conjugate also comprises a detectable group. The conjugate is administered to the patient and at least two or more biological samples are removed from the patient at various times after administration of the conjugate. The samples are treated with electromagnetic radiation to release the pharmaceutical from the bioreactive agent and the amount of the bioreactive agent in the biological samples determined. The in vivo half-life of the pharmaceutical can be determined.

Another embodiment of the invention is directed to methods for the controlled release of a substrate into a medium. A conjugate comprised of a bioreactive agent coupled to the substrate by a covalent bond which can be selectively cleaved with electromagnetic radiation is created wherein the bioreactive agent is comprised of photoreactive group. In other embodiments, the conjugate also comprises a detectable group. The conjugate is bound to a surface of an article which is placed into the medium. The surface of the article is exposed to a measured amount of electromagnetic radiation for the controlled release of the substrate into the medium.

Another embodiment of the invention is directed to methods for detecting a target molecule in a heterologous mixture. A conjugate is formed by coupling a substrate to a bioreactive agent with a covalent bond that is selectively cleavable with electromagnetic radiation, wherein the bioreactive agent is comprised of a photoreactive group. In other embodiments, the conjugate also comprises a detectable group. The conjugate is contacted with the heterologous mixture to couple substrate to one or more target molecules. Uncoupled conjugates are removed and the coupled conjugates are treated with electromagnetic radiation to release the detectable group. The released detectable group can now be easily detected.

Another embodiment of the invention is directed to methods for detecting a target molecule in a heterologous mixture. A conjugate, comprising a substrate coupled to a bioreactive agent, is formed and contacted with a heterologous mixture to couple a conjugate to one or more target molecules. Uncoupled conjugates are removed and the coupled conjugates are treated with electromagnetic radiation to release substrate. Released substrate is detected and can be further isolated.

Another embodiment of the invention is directed to methods for treating a disorder by the controlled release of a therapeutic agent at a selected site. A conjugate is formed by bonding a bioreactive agent to the therapeutic agent with a bond that is selectively cleavable with electromagnetic radiation, wherein the bioreactive agent is comprised of a directable group bonded to a photoreactive group wherein the directable group has an affinity for the selected site. The conjugate is administered to a patient having the disorder. The selected site is subjected to a measured amount of electromagnetic radiation for the controlled release of the therapeutic agent to treat the disorder.

Another embodiment of the invention is directed to kits for detecting a disorder in biological samples containing conjugates comprised of a bioreactive agent (of any of the formulas set forth above) covalently bonded to a diagnostic agent having an affinity for an indicator of the disorder in the biological sample, wherein the covalent bond is selectively cleavable with electromagnetic radiation.

Another embodiment of the invention is directed to kits comprising a bioreactive agent (of any of the formulas above) along with buffers that are useful for washing after the compound is attached to the capture reagent.

Other embodiments and advantages of the invention are set forth, in part, in the description which follows and, in part, will be clear from this description or may be learned from the practice of the invention.

In one embodiment, the present invention contemplates that the AAL portion of the PC-ICAT reagents of the present invention are derived from any amino acid. In a preferred embodiment, it is contemplated that the AAL be derived from any amino acid that is commercially available in (or can be produced as) light (not labeled) and heavy (stable isotope labeled) forms. Thus, while all of the formulas have been described (see above) in the form of a isotoped labeled compound, the unlabeled forms are also contemplated. This permits the use of compounds that are substantially chemically identical, but isotopically distinguishable. Linker groups with stable isotopes function as detectable groups. This allows for the comparison of two populations, e.g., one treated with the heavy reagent and the other treated with the light non-labeled reagent. Additionally, a method for the production of molecules comprising deuterium atoms is given in U.S. Patent Application No. 2002/0119490 A1 and references therein, all of which are incorporated herein by reference. For example, one or more hydrogens in the linker can be substituted with deuterium to generate isotopically heavy reagents.

The present invention also contemplates that the intermediates of the various synthesis schemes are useful. In one embodiment, the present invention contemplates a composition comprising a compound selected from a group consisting of PC-Biotin-NHS ester (compound 8, FIG. 12), water soluble PC-Biotin-NHS ester (compound 7, FIG. 13), a water soluble PC-Biotin-lysine-maleimide conjugate (compound 4, FIG. 14A), a water soluble PC-Biotin-valine-maleimide conjugate (compound 4, FIG. 14B) and, a water soluble PC-Biotin-leucine-maleimide conjugate (compound 4, FIG. 14C).

Moreover, while some the methods described (see above) have been set forth in the context of particular techniques, the present invention contemplates embodiments wherein the isolated targets are characterized by means other than mass spectrometry (e.g. by standard sequencing, by electrophoresis, etc.).

An embodiment of the present invention contemplates a composition comprising at least one of the compounds of the present invention, wherein said compound is photocleavably coupled to a target molecule. In another embodiment, the present invention contemplates that the electromagnetic radiation used to release the substrate is selected from the group consisting of X-rays, ultraviolet radiation, visible light, infrared light, microwaves, radio waves and combinations thereof.

Another embodiment of the invention is directed to methods wherein said compositions are used as isotope-coded affinity tags (ICAT). Is this embodiment, the compositions of the present invention bind to the substrate (e.g., proteins or protein fragments). The bound fragments are then isolated by the binding of the affinity group to a capture reagent (CR) which may or may not be immobilized (e.g., to a solid support). For example, in one embodiment, the present invention contemplates affinity chromatography, wherein the capture reagent is immobilized to the chromatography matrix. In this way, the bound fragments are isolated. The proteins or protein fragments are then released from the binding material by electromagnetic radiation. The released protein or protein fragments are then analyzed with, for example, mass spectrometry.

In further embodiments, this invention contemplates analytical bioagents and mass spectrometry-based methods using these reagents for the rapid and quantitative analysis of proteins or protein function in mixtures of proteins, wherein the bioagent comprises a photoreactive group (i.e., a photocleavable group). The analytical method can be used, for example, for qualitative and, particularly, for quantitative analysis of global protein expression profiles in cells and tissues, i.e., the quantitative analysis of proteomes. The method can also be employed to screen for and identify proteins whose expression level in cells, tissue or biological fluids is altered by a stimulus (e.g., administration of a drug or contact with a potentially toxic material), by a change in environment (e.g., nutrient level, temperature, passage of time) or by a change in condition or cell state (e.g., disease state, state of differentiation, malignancy, site-directed mutation, gene knockouts, etc.) of the cell, tissue or organism from which the sample originated. The proteins identified in such a screen can function as markers for the changed state. For example, comparisons of protein expression profiles of normal and malignant cells can result in the identification of proteins whose presence or absence is characteristic and diagnostic of the malignancy.

In one embodiment, the methods herein can be employed to screen for changes in the expression or state of enzymatic activity of specific proteins. These changes may be induced by a variety of chemicals, including pharmaceutical agonists or antagonists, or potentially harmful or toxic materials. The knowledge of such changes may be useful for diagnosing enzyme-based diseases and for investigating complex regulatory networks in cells.

The methods herein can also be used to implement a variety of clinical and diagnostic analyses to detect the presence, absence, deficiency or excess of a given protein or protein function in a biological fluid (e.g., blood), or in cells or tissue. The method is particularly useful in the analysis of mixtures of proteins.

In other embodiment, the invention contemplates one or more affinity groups or labels coupled (e.g., through one or more linkers) to the protein reactive groups. The affinity labels allow, for example, for the selective isolation of peptide fragments or the products of reaction with a given protein (e.g., products of enzymatic reaction) from complex mixtures. The affinity group(s) may also function as detectable groups. The isolated peptide fragments or reaction products are characteristic of the presence of a protein or the presence of a protein function, e.g., an enzymatic activity, respectively, in those mixtures. Isolated peptides or reaction products are characterized by mass spectrometric (MS) techniques. In particular, the sequence of isolated peptides can be determined using tandem MS (MS/MS) techniques, and by application of sequence database searching techniques, the protein from which the sequenced peptide originated can be identified. The reagents also provide for differential isotopic labeling of the isolated peptides or reaction products which facilitates quantitative determination by mass spectrometry of the relative amounts of proteins in different samples. Also, the use of differentially isotopically-labeled reagents as internal standards facilitates quantitative determination of the absolute amounts of one or more proteins or reaction products present in the sample.

One or more of the $CH_2$, groups of the linker can be optionally substituted with small (C1–C6) alkyl, alkenyl, or alkoxy groups, an aryl group or can be substituted with functional groups that promote ionization, such as acidic or basic groups or groups carrying permanent positive or negative charge. One or more single bonds connecting CH, groups in the linker can be replaced with a double or a triple bond.

In a preferred embodiment, the linker contains groups that can be cleaved to remove the affinity tag. If a cleavable linker group is employed, it is typically cleaved after affinity tagged peptides, substrates or reaction products have been isolated using the affinity label together with the CR. In this case, any isotopic labeling in the linker prefer-ably remains bound to the protein, peptide, substrate or reaction product. In a more preferred embodiment, the cleavable linker group is a photocleavable group of the present invention.

Linker groups include, for example, among others: ethers, poly-ethers, ether diamines, polyether diamines, diamines, amides, polyamides, polythioethers, disulfides, silyl ethers, alkyl or alkenyl chains (straight chain or branched and portions of which may be cyclic), aryl, diaryl or alkylaryl groups. Aryl groups in linkers can contain one or more heteroatoms (e.g., N, O or S atoms).

In one embodiment, the invention provides a mass spectrometric method for identification and quantitation of one or more proteins in a complex mixture which employs affinity labeled reagents (of any of the formulas provided above) in which the PRG is a group that selectively reacts with certain groups that are typically found in peptides (e.g., sulfhydryl, amino, carboxy, homoserine lactone groups). One or more affinity labeled reagents with different PRG groups are introduced into a mixture containing proteins or fragments thereof and the reagents react with certain proteins to tag them with the affinity label. In some embodiments, it may be necessary to pretreat the protein mixture to reduce disulfide bonds or otherwise facilitate affinity labeling. Preferably, after reaction with the affinity labeled reagents, proteins in the complex mixture are cleaved, e.g., enzymatically, into a number of peptides. In some embodiments, this digestion step may not be necessary, if the proteins are relatively small. Preferably, peptides that remain tagged with the affinity label are isolated by an affinity isolation method, e.g., affinity chromatography, via their selective binding to the CR. In some embodiments, isolated peptides are released from the CR by displacement of A or cleavage of the linker, and released materials are analyzed by liquid chromatography/mass spectrometry (LC/MS). In some embodiments, the sequence of one or more tagged peptides is then determined by MS/MS techniques. Typically, at least one peptide sequence derived from a protein will be characteristic of that protein and be indicative of its presence in the mixture. Thus, the sequences of the peptides typically provide sufficient information to identify one or more proteins present in a mixture.

In another embodiment of the present invention (see, FIGS. 10 and 11), quantitative relative amounts of proteins in one or more different samples containing protein mixtures (e.g., biological fluids, cell or tissue lysates, etc.) can be determined using chemically identical, affinity tagged and differentially isotopically labeled reagents to affinity tag and differentially isotopically label proteins in the different samples. In this method, each sample to be compared is treated with a different isotopically labeled reagent to tag certain proteins therein with the affinity label. In one embodiment, the treated samples are then combined, preferably in equal amounts, and the proteins in the combined sample are enzymatically digested, if necessary, to generate peptides. Some of the peptides are affinity tagged and in addition tagged peptides originating from different samples are differentially isotopically labeled. As described above, affinity labeled peptides are isolated, released from the capture reagent and analyzed by LC/MS (liquid chromatography/mass spectrometry). Peptides characteristic of their protein origin are sequenced using MS/MS (tandem mass spectrometry) techniques allowing identification of proteins in the samples. The relative amounts of a given protein in each sample is determined by comparing relative abundance of the ions generated from any differentially labeled peptides originating from that protein. The method can be used to assess relative amounts of known proteins in different samples. Further, since the method does not require any prior knowledge of the type of proteins that may be present in the samples, it can be used to identify proteins which are present at different levels in the samples examined. More specifically, in one embodiment, the method can be applied to screen for and identify proteins which exhibit differential expression in cells, tissue or biological fluids. It is also possible to determine the absolute amounts of specific proteins in a complex mixture. In this case, a known amount of internal standard, one for each specific protein in the mixture to be quantified, is added to the sample to be analyzed. The internal standard is an affinity tagged peptide that is identical in chemical structure to the affinity tagged peptide to be quantified except that the internal standard is differentially isotopically labeled, either in the peptide or in the affinity tag portion, to distinguish it from the affinity tagged peptide to be quantified. The internal standard can be provided in the sample to be analyzed in other ways. For example, a specific protein or set of proteins can be chemically tagged with an isotopically-labeled affinity tagging reagent. A known amount of this material can be added to the sample to be analyzed. Alternatively, a specific protein or set of proteins may be labeled with heavy atom isotopes and then derivatized with an affinity tagging reagent.

In this regard, a preferred embodiment of the present invention is shown in FIG. 10. Protein mixtures obtained from 2 different cellular states (for example stimulated and unstimulated cell) are separately labeled with Bioreactive Agents; in this case Photocleavable ICAT (PC-ICAT) reagents. One of the protein mixtures is labeled with the version of the reagent that does not carry stable isotope labels while the other is labeled with a version that comprises stable isotope labels. After the labeling, the mixtures are combined, digested and the resulting PC-ICAT labeled peptides captured on an affinity support. After exposure to electromagnetic radiation (for example near-UV light) the modified peptides are released and analyzed using mass spectrometry. The intergrated intensities of peaks that are generated by light and heavy modifications are then used to determine parent protein abundance in the sample.

FIG. 11 shows a more detailed structure of certain embodiments of the Photocleavable ICAT (PC-ICAT) conjugates of the present invention. They comprise the affinity tag, photocleavable linker, variable mass linker and the peptide to which they are linked during the reaction. Upon photorelease and mass spectrometry analysis they generate a set of peaks that are separated by the mass difference in the composition of the light and heavy Variable Mass Linkers (VML).

Also, in another embodiment, it is possible to quantify the levels of specific proteins in multiple samples in a single analysis (multiplexing). In this case, affinity tagging reagents used to derivatize proteins present in different affinity tagged peptides from different samples can be selectively quantified by mass spectrometry.

In this embodiment of the invention, the method provides for quantitative measurement of specific proteins in biological fluids, cells or tissues and can be applied to determine global protein expression profiles in different cells and tissues. The same general strategy can be broadened to achieve the proteome-wide, qualitative and quantitative analysis of the state of modification of proteins, by employing affinity reagents with differing specificity for reaction with proteins. The method and reagents of this invention can be used to identify low abundance proteins in complex mixtures and can be used to selectively analyze specific groups or classes of proteins such as membrane or cell surface proteins, or proteins contained within organelles, sub-cellular fractions, or biochemical fractions such as immunoprecipitates. Further, these methods can be applied to analyze differences in expressed proteins in different cell states. For example, in certain embodiments, the methods and reagents herein can be employed in diagnostic assays for the detection of the presence or the absence of one or more proteins indicative of a disease state, such as cancer.

In another embodiment, the invention provides a MS method for detection of the presence or absence of a protein function, e.g., an enzyme activity, in a sample. The method can also be employed to detect a deficiency or excess (over normal levels) of protein function in a sample. Samples that can be analyzed include various biological fluids and materials, including tissue and cells. In this case, the PRG of the affinity labeled reagent is a substrate for the enzyme of interest. Affinity labeled substrates are provided for each enzyme of interest and are introduced into a sample where they react to generate affinity labeled products, if the enzyme of interest is present in the sample. Products or unreacted substrate that are tagged with the affinity label are isolated by an affinity isolation method, e.g., affinity chromatography, via their selective binding to the CR. The isolated tagged substrates and products are analyzed by mass spectrometry. Affinity labeled products include those in which the substrate is entirely cleaved from the linker or in which the substrate is modified by reaction with a protein of interest. Detection of the affinity-labeled product indicates the protein function is present in the sample. Detection of little or no affinity labeled product indicates deficiency or absence, respectively, of the protein function in the sample.

In yet another embodiment, the amount of selected protein, e.g., measured in terms of enzyme activity, present in a sample can be measured by introducing a known amount of an internal standard which is an isotopically labeled analog of the expected product of the enzymatic reaction of the reagent substrate. The internal standard is substantially chemically identical to the expected enzymatic reaction product, but is isotopically distinguishable therefrom. The level of protein function (e.g., enzymatic activity) in a given sample can be compared with activity levels in other samples or controls (either negative or positive controls). The procedure therefore can detect the presence, absence, deficiency or excess of a protein function in a sample. The method is capable of quantifying the velocity of an enzymatic reaction since it enables the amount of product formed over a known time period to be measured. This method can be multiplexed, by simultaneous use of a plurality of affinity labeled substrates selective for different protein functions and if quantitation is desired by inclusion of the corresponding internal standards for expected products, to analyze for a plurality of protein functions in a single sample.

Importantly, the compounds of the present invention can be used in methods other than traditional ICAT. For example, one embodiment of the present invention is directed towards detection of enzymatically modified proteins or polypeptides which may be part of a heterogeneous mixture including a library of proteins and/or polypeptides.

A variety of enzymes act selectively on protein or polypeptide substrates to produce modifications which introduce groups which can interact with the compositions of this invention to form conjugates. Examples include but are not limited to kinases (phosphorylases) and phosphatases which introduce and remove phosphate moieties on tyrosine, serine and threonine residues; acetylases and deacetylases which add and remove acetyl groups from residues such as lysine; and methylases and demethylases which introduce and remove methyl groups from chemical groups. A variety of additional enzymes which exhibit substrate specificity are well known and are involved in post-translation modification of proteins including but not limited to enzymes involved in the addition or removal of chemical moieties to proteins such as sugars (e.g. oligosacharides) to form glycoproteins and the 15 carbon farnesyl group or the 20 carbon geranylgeranyl group known as prenylation.

It is well known that these enzymes play an important role in regulation of cellular process, although in the case of many enzymes the details are not yet elucidated including the enzyme specificity for different substrates. For example, several studies have revealed that acetylation of histones is an important step in controlling transcription. See Grunstein, M. "Histone acetylation in chromatin structure and transcription." *Nature* 389, 349–352 (1997). In addition to histones, a variety of other proteins have been identified as substrates for acetylases and include DNA-binding proteins (transcription factors), non-nuclear proteins (tubulin) and proteins that shuttle from the nucleus to the cytoplasm, such as members of the importin-alpha-family. See Kouzarides, T. "Acetylation: a regulatory modification to rival phosphorylation," *Embo J* 19, 1176–1179 (2000). The specificity of acetylases for specific lysines in a protein is highly selective and depends on recognition of a consensus sequence. For example, it has been suggested that the sequence GK may be part of a recognition motif and the recent crystal structure of the acetylase GCN5 led to identification of GKXXP as a possible motif. However, in general, recognition motifs are unknown for most acteylases and even less is known about deacetylases. Such information is helpful in understanding the role of acetylases/deacetylases in cellular process and in particular in identifying proteins as potential drug targets.

An additional example of a deacetylase whose substrate specificity is not completely known is the SIR2 (silent information regulator 2) gene family. See Onyango, P. et al, "SIRT3, a human SIR2 homologue, is an NAD-dependent deacetylase localized to mitochondria." *Proc Natl Acad Sci USA* 99, 13653–13658 (2002) and Shore, D. "The Sir2 protein family: A novel deacetylase for gene silencing and more," Proc Natl Acad Sci USA 97, 14030–14032 (2000).

SIR2 in related proteins have been found to play a key role in yeast including gene silencing, DNA repair, cell-cycle progression, and chromosome fidelity in meiosis and aging. Studies have shown that SIR2 is NADP-dependent and that Sir2-like enzymes perform a novel reaction in which NAD cleavage and deacetylation are tightly coupled. Furthermore, it has been proposed that there exists a link between caloric restriction in yeast and increased lifespan which is modulated by the SIR2 and NPT1-dependent pathways. See Guarente, L., "Sir2 links chromatin silencing, metabolism, and aging," *Genes Dev* 14, 1021–1026 (2000) and Lin, S. J. et al, "Requirement of NAD and SIR2 for life-span extension by calorie restriction in *Saccharomyces cerevisiae."* Science 289, 2126–2128 (2000).

The compositions of the present invention including photoreactive bioagents can be used advantageously to identify the substrate specificity of a wide range of enzymes. One embodiment of the invention is directed to bioreactive agents comprising a detectable group bonded to a photoreactive group wherein the photoreactive group contains at least one group capable of covalently bonding to a substrate which has been enzymatically modified from the unmodified substrate to form a conjugate that can be selectively photocleaved to release said substrate. Detectable groups should have a selectively detectable physical property such as fluorescence, absorption or an ability to specifically bind to a coupling agent such as avidin or streptavidin, antibodies, antigens or binding proteins. In one embodiment, the bioreactive agent comprises PC-biotin-NHS or PC-biotin-lysine NHS (FIGS., 12, 13 and 14E) the synthesis of which are described. In one embodiment, the bioreactive agent does not comprise a detectable group. In a preferred embodiment, the detectable group is a differentially isotopically labeled reagent. It is contemplated that the detectable group is bound to the bioreactive reagent or a portion of the bioreactive agents of the present invention are altered or function as a detectable group. The photoreactive group should be capable of forming one or more covalent bonds with a chemical group of a substrate or other reagents comprising the bioreactive agent. Those covalent bonds may be photocleaved with electromagnetic radiation releasing the substrate or the substrate and a portion of the bioreactive reagent, depending on the arrangement of the various groups of the bioreactive reagent. In this regard, the present invention contemplates a bioreactive agent of the general formula:

A-L-PR-AAL-PRG wherein (A) is an affinity label (which may also function as, or be bound to, a detectable group), (L) is a linker group (which may also function as, or be bound to, a detectable group), (PR) is a photoreactive group, (AAL) is an amino acid linker group and (PRG) is the protein reactive group. Examples of these agents are given in FIGS. 12, 13 and 14A–F (the present invention is not limited to the examples shown in the specification or in the Figures). Other phoreactive bioagents (of any of the above-described formulas) that are useful are described herein.

In one embodiment of the invention it is contemplated that at least a portion of a heterogeneous mixture of molecules (which includes but is not limited to a cell lysate or library of polypeptides, proteins or nucleic acids) is treated with a specific enzyme such as a deacetylase, as part of one embodiment of a method designed to determine which molecules are enzymatically modified by said enzyme and therefore serve as substrates for the enzyme. After enzyme modification, the mixture is contacted with the bioreactive agent. In the case of proteins or polypeptides, a protein reactive group (PRG) is chosen for the bioreactive agent such that it will react with a chemical group which is formed on the substrate after modification by the enzyme. For the purpose of determining enzyme substrate specificity for other biomolecules including but not limited to nucleic acids, carbohydrates and lipids, a variety of reactive groups have been described in this invention.

One exemplary embodiment of a method of determining substrate specificity for a deacetylase provides a bioreactive reagent containing an affinity group which is detectable by specifically binding to a coupling agent, a photoreactive group and a protein reactive group which reacts with amine groups and comprises the following steps:

1) Preparing a library of synthetic polypeptides (peptides) which comprises a sequence comprising an acetylated lysine residue. In order to reduce complexity of analysis, in some cases additional lysines in the sequence are not allowed or limited to a small number such as one or two. Furthermore, in order to eliminate possible reactivity, the N-terminal amino group in some cases is blocked with a group (e.g. a protecting group) which does not function as a substrate for deacetylases. Examples include Fmoc or T-boc;

2) Treating at least a portion of the library of peptides with the enzyme so as to create a treated portion. For example, a portion of the library is treated with the deacetylase under conditions designed to remove the acetyl group from the acetylated lysines, so as to create a population of polypeptides comprising lysines with free amino groups;

3) Derivatization of said free amino groups with an affinity tag. Free amine groups are derivatized with an amine-reactive probe. Examples include PC-biotin-NHS or PC-biotin-lysine-NHS (FIGS. 12, 13 and 14E), the synthesis of which are described;

4) Removal of excess affinity tagged reagent. Excess reagent is removed in a variety of ways, depending on the format chosen. For example, in one embodiment, free reagent is removed (e.g. substantially removed) by dialysis. Alternatively, the reagent is adsorbed, for example, by adding an excess of amine-containing beads to the reaction mixture after protein or polypeptide amine groups are completely derivatized. Beads are added to the solution to achieve about a 5-fold molar excess of amine groups over the reagent added and incubated for 30 min at RT. After the reaction the beads are be removed by centrifugation;

5) Polypeptide digestion with a protease. This step may be omitted in some cases such as a library of small polypeptides (e.g. polypeptides less than 20 amino acids in length). In the case of larger polypeptides or proteins, the sample mixture is digested with a protease, typically with trypsin. Alternative proteases are also compatible with the procedure as in fact are chemical fragmentation procedures (for example, CNBr cleavage). In cases in which the preceding steps were performed in the presence of high concentrations of denaturing solubilizing agents the sample mixture is diluted until the denaturant concentration is compatible with the activity of the proteases used. This step may be omitted in the analysis of small proteins;

6) Affinity isolation of the affinity tagged peptides by interaction with a capture reagent. The biotinylated peptides are immobilized on beads coated with avidin or streptavidin (Pierce, Rockford, Ill.). The beads are extensively washed. The last washing solvent can include 10% methanol to remove residual SDS. Immobilized polypeptides are eluted from avidin-agarose, by resuspending in ammonium acetate buffer and irradiating with near UV light for 10–15 minutes. Alternatively, the biotinylated peptides are captured on monomeric avidin agarose support and eluted with 0.2% formic acid (pH=2). After chemical elution, the PC-Biotin portion is removed by irradiation with near UV light for 10–15 minutes and analyzed;

8) Analysis of the isolated peptides by μLC-MS or CE-MS/MS with data dependent fragmentation. Methods and instrument control protocols well-known in the art and described, for example, in Ducret, et al., 1998; Figeys and Aebersold, 1998; Figeys, et al., 1996; or Haynes, et al., 1998 are used. Alternatively, reverse phase LC separation, fraction collection and analysis by MALDI-MS can be used.

In this last step, both the quantity and sequence identity of the peptides which originate from portions of the polypeptides or proteins that are specifically modified by the enzyme (or the polypeptides in the library that are modified by the enzyme) can be determined by automated multistage MS. This is achieved by the operation of the mass spectrometer in a dual mode in which it alternates in successive scans between measuring the relative quantities of peptides eluting from the capillary column and recording the sequence information of selected peptides. Peptide sequence information is automatically generated by selecting peptide ions of a particular mass-to-charge (m/z) ratio for collision-induced dissociation (CID) in the mass spectrometer operating in the MS/MS mode. (Link, A. J., et al., 1997; Gygi, S. P., et al. 1999). The resulting CID spectra are then automatically correlated with sequence databases to identify the protein from which the sequenced peptide originated. Combination of the results generated by MS and MS/MS analyses of affinity tagged and differentially labeled peptide samples therefore determines the relative quantities as well as the sequence identities of the components of protein or polypeptide mixtures in a single, automated operation.

In another exemplary embodiment of a method of determining substrate specificity for a deacetylase provides a bioreactive reagent containing an affinity group which is detectable by specifically bind to a coupling agent, a photoreactive group, a linker group which can be isotopically labeled and a protein reactive group which reacts with amine groups and comprises the following steps:

1) Preparing a library of synthetic polypeptides (peptides) which contain a sequence comprising an acetylated lysine residue. In order to reduce complexity of analysis, in some cases additional lysines in the sequence are not allowed or limited to a small number such as one or two. Furthermore, in order to eliminate possible reactivity, the N-terminal amino group in some cases is blocked with a group (e.g. a protecting group) which does not have substrate specificity for deacetylases. Examples include Fmoc or T-boc;

2) Treating at least a portion (e.g. first sample) of the library of peptides with the enzyme. The library of polypeptides (or portion thereof) is then treated with the deacetylase under conditions designed to partially remove or completely remove the acetyl group from the acetylated lysines, so as to create a treated portion or treated sample. In some cases, different samples (e.g. first and second samples) are created by using different conditions for deacetylation ranging from non-addition of the enzyme to conditions that allow the enzymatic reaction to go to completion;

3) Derivatization of free amino group on peptides in said treated sample with an affinity tag. Free amine groups are derivatized with the an amine-reactive probe such as PC-Biotin-biotinylating reagent, for example PC-biotin-NHS or PC-biotin-lysine-NHS (FIGS. 12, 13 and 14E) the synthesis of which are described. The reagent is prepared in different isotopically labeled forms by substitution of linker atoms with stable isotopes and each sample is derivatized with a different isotopically labeled form of the reagent. For the quantitative, comparative analysis of two samples, one sample each (termed reference sample and test sample) are derivatized with the isotopically light and the isotopically heavy form of the reagent, respectively. For the comparative analysis of several samples, one sample is designated a reference to which the other samples are related. Typically, the reference sample is labeled with the isotopically heavy reagent and the experimental or test samples are labeled with the isotopically light form of the reagent, although this choice of reagents is arbitrary (and could be reversed). For example, one sample which is isotopically labeled with a heavy reagent may not have been treated with the enzyme whereas the second sample which has been treated with the enzyme is labeled with the isotopically light form of the reagent;

4) Combination of labeled samples. After completion of the affinity tagging reaction defined aliquots of the samples labeled with the isotopically different reagents (e.g., heavy and light reagents) are combined and all the subsequent steps are performed on the pooled samples. Combination of the differentially labeled samples at this early stage of the procedure eliminates variability due to subsequent reactions and manipulations. Preferably equal amounts of each sample are combined (in order to simplify the analysis);

5) Removal of excess affinity tagged reagent. Excess reagent is removed by a variety of approaches. For example, in one embodiment of the method, excess reagent is removed (e.g. substantially removed) by dialysis. Alternatively, the reagent is adsorbed, for example, by adding an excess of amine-containing beads to the reaction mixture after protein or polypeptide amine groups are completely (or at least substantially) derivatized. Beads are added to the solution to achieve about a 5-fold molar excess of amine groups over the reagent added and incubated for 30 min at RT. After the reaction the beads are be removed by centrifugation;

6) Polypeptide digestion with a protease. This step may be omitted in some cases such as a library of small polypeptides. In the case of large polypeptides or proteins, the sample mixture is digested with a protease, typically with trypsin. Alternative proteases are also compatible with the procedure as in fact are chemical fragmentation procedures (for example, CNBr cleavage). In cases in which the preceding steps were performed in the presence of high concentrations of denaturing solubilizing agents the sample mixture is diluted until the denaturant concentration is compatible with the activity of the proteases used. This step may be omitted in the analysis of small proteins;

7) Affinity isolation of the affinity tagged peptides by interaction with a capture reagent. The biotinylated peptides are immobilized on beads coated with avidin or streptavidin (Pierce, Rockford, Ill.). The beads are extensively washed. The last washing solvent includes 10% methanol to remove residual SDS. PC-ICAT modified peptides are eluted from avidin-agarose, by resuspending in ammonium acetate buffer and irradiating with near UV light for 10–15 minutes. Alternatively, the PC-ICAT modified peptides are captured on monomeric avidin agarose support and eluted with 0.2% formic acid (pH=2). After chemical elution, the PC-Biotin portion is removed by irradiation with near UV light for 10–15 minutes and analyzed.

8) Analysis of the isolated, derivatized peptides by μLC-MS or CE-MS/MS with data dependent fragmentation. Methods and instrument control protocols well-known in the art and described, for example, in Ducret, et al., 1998; Figeys and Aebersold, 1998; Figeys, et al., 1996; or Haynes, et al., 1998 are used. Alternatively, reverse phase LC separation, fraction collection and analysis by MALDI-MS can be used.

In this last step, both the quantity and sequence identity of the peptides which originate from portions of the polypeptides or proteins that are specifically modified by the enzyme or the polypeptides in the library that are modified by the enzyme can be determined by automated multistage MS. This is achieved by the operation of the mass spectrometer in a dual mode in which it alternates in successive scans between measuring the relative quantities of peptides eluting from the capillary column and recording the sequence information of selected peptides. Peptides are quantified by measuring in the MS mode the relative signal intensities for pairs of peptide ions of identical sequence that are tagged with the isotopically light or heavy forms of the reagent, respectively, and which therefore differ in mass by the mass differential encoded within the affinity tagged reagent. Peptide sequence information is automatically generated by selecting peptide ions of a particular mass-to-charge (m/z) ratio for collision-induced dissociation (CID) in the mass spectrometer operating in the MS/MS mode. (Link, A. J., et al., 1997; Gygi, S. P., et al. 1999). The resulting CID spectra are then automatically correlated with sequence databases to identify the protein from which the sequenced peptide originated. Combination of the results generated by MS and MS/MS analyses of affinity tagged and differentially labeled peptide samples therefore determines the relative quantities as well as the sequence identities of the components of protein or polypeptide mixtures in a single, automated operation.

It will be recognized by those skilled in the art that the examples described above can be applied with minor modification to identify substrates of particular enzymes inside a heterogeneous mixture consisting of a library of proteins or even a mixture of molecules consisting of a cellular lysate or tissue homogenate. In particular, the similar steps can be used to identify target proteins in a heterogenous mixture which are selectively modified by particular enzyme including but not limited to kinases (phosphoryrlases), phosphatases, acetylases, deacetylases, methylases and demethylases. For example, the effect of a particular deacetylase on a cell lysate will be to remove acetyl groups from a subset of proteins that are acetylated. By following the steps described above including the differential treatment of samples with the modifying enzyme, the sequence of tryptic fragments can be elucidated which are part of proteins that are selectively deacetylated by the-particular deacetylase.

In one embodiment, the present invention contemplates a method, comprising: a) providing i) a mixture comprising polypeptides, ii) a solid support, and iii) a photo-cleavable compound (of any of the general formulas described above with or without isotope labels); b) contacting at least a portion of said mixture with said photocleavable compounds under conditions such that a population of polypeptide-photocleavable compound conjugates are created; c) capturing at least a portion of said polypeptide-photocleavable compound conjugates (or fragments thereof) on said support to create immobilized conjugates; and d) exposing said immobilized conjugates to electromagnetic radiation under conditions such that at least a portion of said immobilized conjugates is released from said solid support so as to create released peptides. In one embodiment, the present invention contemplates that the method further comprises f) analyzing said released peptides using mass spectrometery. Again, it is not intended that the present invention be limited to particular stable isotopes. In one embodiment, said photocleavable compound comprises one or more stable isotopes selected from $^2$H, $^{13}$C, and $^{15}$N.

In yet another embodiment, the present invention contemplates a method of analyzing enzyme substrate specificity comprising: a) providing i) an enzyme, ii) a population comprising biomolecules, a portion of which can serve as substrates for the enzyme, iii) a solid support, and iv) a photocleavable compound (of any of the general formulas described above with or without isotope labels); b) contacting said population with said enzyme so as to create a treated population; c) contacting said treated population with said photocleavable compounds under conditions such that biomolecule-photocleavable compound conjugates are created; d) capturing at least a portion of said biomolecule-photocleavable compound conjugates on said support to create immobilized conjugates; and e) exposing said immobilized conjugates to electromagnetic radiation under conditions such that at least a portion of said immobilized conjugates is released from said solid support so as to create released biomolecules. In one embodiment, the method further comprises f) analyzing said released biomolecules using mass spectrometery. Again, a variety of isotopes can be used. In one embodiment, said photocleavable compound comprises one or more stable isotopes selected from $^2$H, $^{13}$C, and $^{15}$N.

DESCRIPTION OF FIGURES

FIG. 9 shows the four basic steps in the isolation of pure substrate using PCB.

FIG. 10 shows a diagram of protein quantitation procedure compatible with the Photocleavable Bioreactive Agents with Variable Mass Linkers of the present invention.

FIG. 14E shows examples of PC-ICAT reagents designs with various reactive groups utilizing lysine as a linker. It should be noted in this figure that the designation PC-Biotin is not intended to show a specific order of these parts of the molecule. In fact, the specific order of these constituents is Biotin-PC.

FIG. 20 shows masses calculated and observed from PC-Biotin-lysine-maleimide (α-Maleimidopropyloxy-, ε-PC-Biotin-Lys(U-$^{12}$C$_6$,$^{14}$N$_2$)—OH (light) reagent reaction mixtures with peptide analogs in solution and upon affinity capture and photorelease from streptavidin-agarose. The most intense peaks are in boldface, the mass tagged peaks after photocleavage are underlined boldface.

FIG. 25 shows theoretical and MALDI-MS—determined ratios for the light (Lys(U-$^{12}$C$_6$,$^{14}$N$_2$)) and heavy (Lys(U-$^{13}$C$_6$,$^{15}$N$_2$)) PC-ICAT ((α-Maleimidopropyloxy-, ε-PC-Biotin-Lys-OH) modified peptides, SV40 and HIV gp120 analog.

DEFINITIONS

Figure 1:
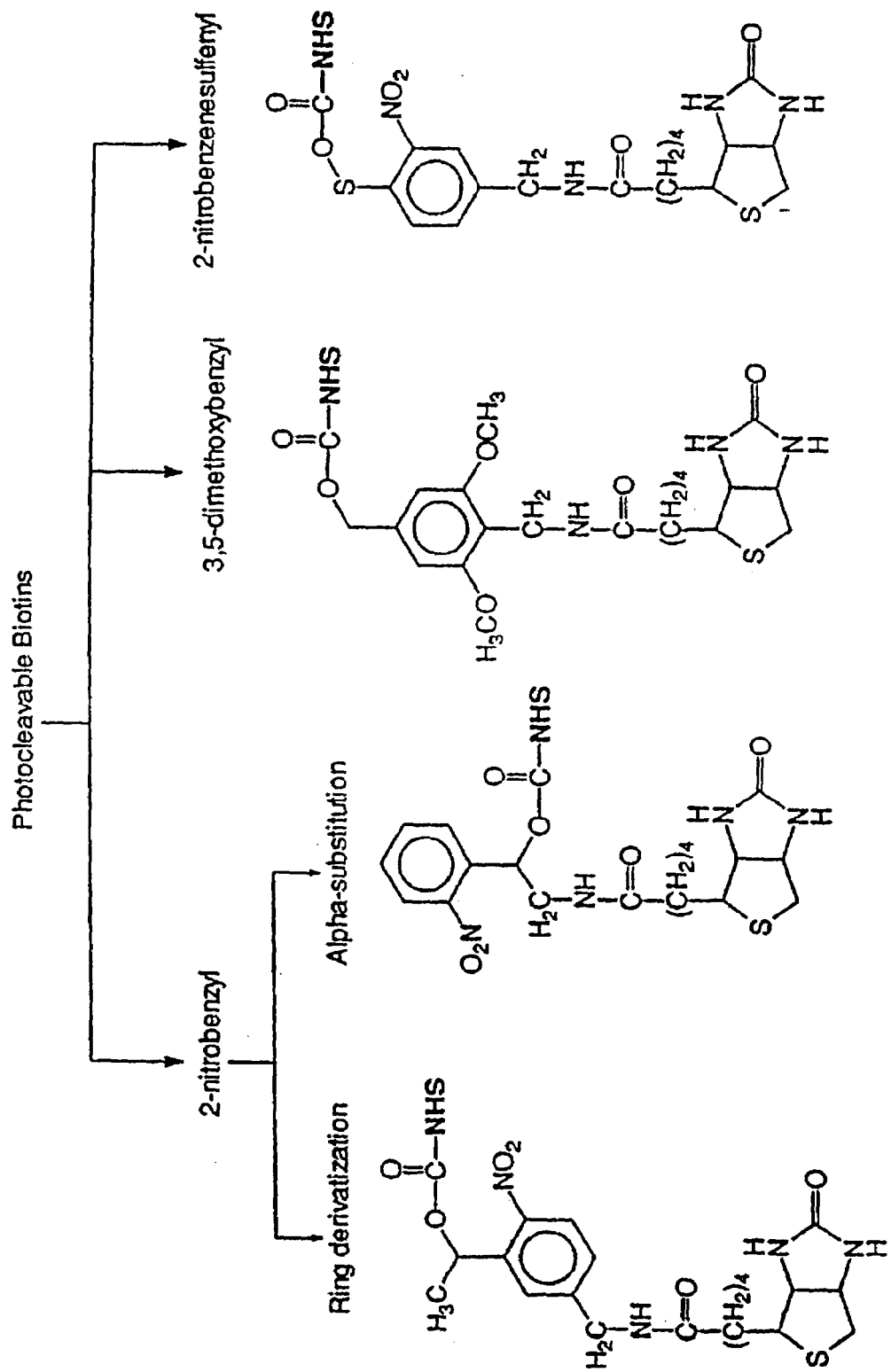
FIG. 1 shows embodiments of photocleavable biotins with various photoreactive groups.

In order to aid in the understanding of this document, the following definitions are provided.

"Bioreagent" shall be defined as a synthetic (e.g., a synthetically produced pharmaceutical) or naturally occurring (e.g., a vitamin, enzyme or the like) compound that functions or has the potential to function in a biological organism or interact with biomolecules. The bioreactive agents of the present invention are bioreagents.

"Proteome" shall be defined as the protein complement expressed by a genome. While the genome is static, the proteome continually changes in response to external and internal events. That is, a proteome is defined as the total possible complement of proteins coded by the nucleic acid of an organism (i.e., as coded by the organisms genome).

"Spliceome" shall be defined as the RNA splicing regulation that is cell type-specific in such a way that a cellular situation can be characterized by its repertoire of spliced events. In other words, it is the total complement of splice events for a cell that leads to the total complement of RNA possible including all splice variants of the RNA.

"Capture reagent" shall be defined as a reagent that binds to as affinity group or affinity label. The capture reagent can be used, for example, isolating the compounds of the present invention when the compounds of the present invention are coupled to a substrate.

"Affinity groups" (or "moieties") shall be defined as a portion of a molecule or compound that binds to a reagent or capture reagent. For example, biotin is an affinity label that binds selectively to the capture reagents avidin and strepavidin. Affinity groups may also function as detectable groups.

"Linker group" or "linker" shall be defined as a molecule or molecules that link chemical groups or functional groups together. In some embodiments, the linker acts as a spacer for two or more functional groups within the molecule or compound. A linker may contain acidic or basic groups, e.g., COOH, $SO_3H$, primary, secondary or tertiary amino groups, nitrogen-heterocycles, ethers or combinations of these groups. The linker may also contain groups containing a permanent charge, e.g., phosphonium groups, quaternary groups, sulfonium groups, chelated metal ions, tetralky or tetraryl borate or stable carboniums. In a preferred embodiment, the linker can be isotopically labeled.

"Protein reactive group" shall be defined as a portion of a molecule or compound that binds to certain proteins, protein fragments or protein functional groups. Any selectively reactive protein reactive group should react with a functional group of interest that is present in at least a portion of the proteins in a sample. For example, the reactive site of an enzyme is a protein reactive group as is the epitope binding site of an antibody. These and other protein reactive groups may be incorporated into the bioreactive agents of the present invention.

"Photoreactive group" shall be defined as a portion of a molecule that is cleavable upon exposure to electromagnetic radiation. The photoreactive group is independent of any linker present in the molecule but can serve as a linker.

"Differentially labeled" shall be defined as labeling where zero, one or more of the sites capable of being labeled are labeled. For example, in one embodiment of the present invention, the linker group may have zero or one or more deuterium ions attached. In one embodiment of the present invention, the linker group of a first portion of a compound has eight deuterium ions attached and the linker group of a second portion of the compound has zero deuterium ions attached. The present invention is not limited as to the type of label used or to the number of available label sites or as to the number of available label sites actually labeled. In a preferred embodiment, the number of labeled sites is less than 20; in a more preferred embodiment, the number of label sites is less than 10. In some embodiments, the number of sites is one.

"Selectively reacts" and binds selectively shall be defined as a reaction, wherein the reaction is limited by a characteristic or characteristics of one or more of the groups involved (i.e., the reactive group or the substrate). For example, the protein reactive group of the present invention has to ability to selectively react with the substrate.

"Mixture" shall be defined as a material of variable composition that contains two or more substances.

"Heterologous mixture" shall be defined as a mixture wherein that is derived from substances from two or more sources. For example, a mixture of cell extracts from two or more types of cells would be a heterologous mixture.

"Substrate" shall be defined as a molecule or compound that is capable of binding (e.g., covalently) in a reaction with another molecule or compound. "Target" shall be defined to be synonymous with substrate.

"Reaction" shall be defined as a chemical or biochemical event, wherein one or more types of molecules or compounds interact such that there is a change or transformation in which a substance decomposes, combines with other substances, or interchanges constituents with other substances.

"Target molecule" shall be defined as a molecule or compound upon which a compound of the present invention reacts, selectively reacts, couples or binds.

"Coupled conjugate" shall be defined as a compound that is made up of one or more smaller compounds. For example, in one embodiment of the present invention, a coupled conjugate comprises a bioreactive agent bound to a substrate.

"Covalent bond" shall be defined as the bonds in compounds that result from the sharing of one or more pairs of electrons.

"Detectable group" shall be defined as a molecule that can be quantitatively or qualitatively detected by techniques known to those in the art. The bioreactive agent of the present invention need not comprise a detectable group. The detectable group may consist of a molecule added to the bioreactive agent or a subgroup of the bioreactive agent may also function as a detectable group. For example, the linker group may comprise deuterium ions or the affinity group may comprise biotin.

A "stable isotope" is "stable" in it shows relatively low tendency to undergo radioactive decomposition (e.g. a half-life of greater than 100,000 years). Preferred stable isotopes of the present invention are $^2H$, $^{13}C$, $^{15}N$.

DESCRIPTION OF THE INVENTION AND SPECIFIC EMBODIMENTS

As embodied and broadly described herein, the present invention is directed to agents and conjugates used in the detection and isolation of targets such as chemicals, macromolecules, cells and any identifiable substance from a mixture, e.g., proteins and protein fragments. In one embodiment, agents comprise a protein reactive group (PRG) group bound to a photoreactive (PR) group and conjugates comprise agents which are coupled to substrates via the PRG by one or more covalent bonds which, by the presence of the photoreactive group, are selectively cleavable with electromagnetic radiation. The invention is also directed to methods for the isolation and detection of targets using these agents and conjugates, to kits which utilize these methods for the detection of diseases and disorders in patients, and to methods for the detection and isolation of nearly any substance from a heterologous mixture. In another embodiment, the invention also comprises a detectable group. The detectable group may comprise the PRG (for example, the PRG may comprise isotopically detective constituents) or may be bound (e.g., covalently) to the PRG or other parts of the agent.

The present invention contemplates, in certain embodiments, an agent of the general formula A-L-PR-SL-PRG or L-A-PR-SL-PRG, wherein (A) is an affinity label (which may also function as or be bound to a detectable group), (L) is a first linker group that is not isotopically labeled, (PR) is a photoreactive group, (SL) is a second linker comprising one or more stable isotopes, and (PRG) is the protein reactive group. Examples of these agents are given in FIGS. 12, 13 and 14A–F (the examples in FIGS. 12, 13 and 14A–F are exemplary and do not limit the invention in any way).

1. The Detection and Isolation of Biological Substances

There are many methods currently available for the detection and isolation of a desired substance or target, e.g., proteins and protein fragments, from a complex mixture. Most of these methods require the specific labeling of the substance or target to be detected, detection of that label and subsequent removal of label from target. Although straightforward, current detection and isolation methodologies possess a number of problems. For example, it is often difficult to specifically attach target with label. Affinity of label for target may be low, suitable points of attachment may not be available on specific substances and the label and the target may simply be chemically or physically incompatible. In addition, label may hinder or completely destroy the functional activity of the target thereby frustrating the purpose of isolation. Isolated targets can be unavoidably contaminated or inactivated due to the presence of a toxic or damaging label. A typical example of this sort of problem is the isolation of cells bound with biotin after selection by coupling to streptavidin. The powerful affinity of biotin for streptavidin makes the isolation procedure relatively straightforward and specific, however, the isolated cells are often dead and dying due to the toxic effects of the coupling agents or the harsh isolation procedures. This is also true when attempting to isolate active proteins from biological samples and other complex mixtures for later use. The presence of label may denature or render the protein product inactive or simply unacceptable for in vivo use under current FDA standards and guidelines. Removal of the agent sometimes overcomes these problems, however, methods to separate and remove label from target are generally rather harsh, take a significant amount of time, effort and expense, and, for the most part, result in fairly low yields of the final product. Viability and functional activity of the target is often severely impaired and is often destroyed.

The present invention overcomes these problems by providing bioreactive agents which can detect and isolate targets. In one embodiment, agents of the present invention (as set forth in any of the formulas above) can be covalently coupled to a variety of target substrates, e.g., target proteins and protein fragments. A covalent bond between agent and substrate can be created from a wide variety of chemical groups including amines, hydroxyls, imidazoles, aldehydes, carboxylic acids, esters and thiols. Bioreactive agent/substrate combinations are referred to herein as conjugates. Through the presence of the detectable group, if present, conjugates can be quickly and accurately detected and target isolated. Further, these conjugates are selectively cleavable which provides unique advantages in isolation procedures. Substrate can be separated from agent quickly and efficiently. New attachment and separation procedures do not need to be developed for every new target to be isolated. Following isolation, it is a relatively simple matter to treat the conjugate with electromagnetic radiation (e.g., light of the appropriate wavelength or other appropriate source of electromagnetic radiation) and release the substrate. In one embodiment, the released substrate is preferably functionally active and structurally unaltered. Nevertheless, minor chemical alterations in the structure may occur depending on the point of attachment. It is generally preferred that such alterations not effect functional activity. However, when functional activity does not need to be preserved, such changes are of no considerations and may even be useful to identify and distinguish targets isolated by methods of the invention. After isolation, the targets can be analyzed by, for example mass spectrometry (MS).

Targets, as referred to herein, are those substances being identified, characterized or isolated using the agents, conjugates and methods of the invention. Substrates, as referred to herein, are those substances which are covalently attached to the bioreactive agent.

2. Cleavage via the Photoreactive Group

One embodiment of the present invention is directed to the cleavage of the target from the remainder of the conjugate via the photocleavable group. Cleavage, as referred to herein, is by photocleavage or a cleavage event triggered by the application of radiation to the conjugate. The radiation applied may comprise one or more wavelengths from the electromagnetic spectrum including x-rays (about 0.1 nm to about 10.0 nm; or about $10^{18}$ to about $10^{16}$ Hz), ultraviolet (UV) rays (about 10.0 nm to about 380 nm; or about $8 \times 10^{16}$ to about $10^{15}$ Hz), visible light (about 380 nm to about 750 nm; or about $8 \times 10^{14}$ to about $4 \times 10^{14}$ Hz), infrared light (about 750 nm to about 0.1 cm; or about $4 \times 10^{14}$ to about $5 \times 10^{11}$ Hz), microwaves (about 0.1 cm to about 100 cm; or about $10^{8}$ to about $5 \times 10^{11}$ Hz), and radio waves (about 100 cm to about $10^4$ m; or about $10^4$ to about $10^8$ Hz). Multiple forms of radiation may also be applied simultaneously, in combination or coordinated in a step-wise fashion. Radiation exposure may be constant over a period of seconds, minutes or hours or varied with pulses at predetermined intervals.

Typically, the radiation source is placed at a specified distance from the conjugate to be irradiated. For example, that distance may be empirically determined or calculated from the energy loss produced between the source and the target and the amount of energy emitted by the source. The conjugate may be in solution or attached to a solid support which may be a type of glass, ceramic, polymer or semiconductor surfaces. Typical solid supports are nitrocellulose membranes, agarose beads, magnetic beads coated with streptavidin, semiconductor surfaces and resins. Preferably, the radiation applied is UV, visible or IR radiation of the wavelength between about 200 nm to about 1,000 nm, more preferably between about 260 nm to about 600 nm, and more preferably between about 300 nm to about 500 nm. Radiation is administered continuously or as pulses for hours, minutes or seconds, and preferably for the shortest amount of time possible to minimize any risk of damage to the substrate and for convenience. Radiation may be administered for less than about one hour, preferably less for than about 30 minutes, more preferably for less than about ten minutes, and still more preferably for less than about one minute. Visible, UV and IR radiation are also preferred as all three of these forms of radiation can be conveniently and inexpensively generated from commercially available sources.

The power density or intensity of light per area necessary to selectively cleave the covalent bond is very small which makes the photocleavable process practical. Maximization of efficiency also minimizes exposure time necessary to achieve selective cleavage and provide a minimum of undesirable background effects.

3. Alternate Methods of Detection

Although the preferred embodiment for a method of detection and analysis is via mass spectrometry, the present invention also contemplates alternate methods of detection. In some embodiments, one part of the bioreactive agent is the detectable group. The detectable group is a chemical group, structure or compound that possesses a specifically identifiable physical property which can be distinguished from the physical properties of other chemicals present in the heterologous mixture. Fluorescence, phosphorescence and luminescence including electroluminescence, chemiluminescence and bioluminescence are all detectable physical properties not found in most substances, but known to occur or to be inducible in others. For example, reactive derivatives of dansyl, coumarins, rhodamine and fluorescein are all inherently fluorescent when excited with light of a specific wavelength and can be specifically bound or attached to other substances. Coumarin has a high fluorescent quantum yield, higher than even a dansyl group, and facilitates detection where very low levels of target that are being sought. Coumarin is structurally similar to tryptophan, which can be useful in for example in the translation of nascent proteins with non-native amino acids. It may also be useful to combine certain detectable groups to facilitate detection or isolation. Preferably the detectable group is a fluorescent compound and the preferred fluorescent compounds are listed in Table 1, all of which are commercially available (Sigma Chemical; St. Louis, Mo.).

TABLE 1

Fluorescent Labeling Compounds 4-acetamido-4'-isothiocyanatostilbene-2-2'-disulfonic acid
7-amino-4-methylcoumarin (AMC)
7-amino-4-trifluoromethylcoumarin
N-(4-anilino-1-naphthyl) maleimide
4',6-diamidino-2-phenylindole (DAPI)
5-(4,6-dichlorotriazin-2-yl) aminofluorescein (DTAF)
4,4'-dilsothiocyanatostilbene-2,2'-disulfonic acid
tetramethylrhodamine isothiocyanate (TRITC)
quinolizino fluorescein isothiocyanate (QFITC)
dansyl chloride        eosin isothiocyanate
erythrosin B           fluorescamine
fluorescein            fluorescein derivatives
4-methylumbelliferone  o-phthaldialdehyde
rhodamine B            rhodamine B derivatives
rhodamine 6G           rhodamine 123
sulforhodamine B       sulforhodamine 101
sulforhodamine 101 acid chloride
BODIPY (4,4-difluoro-5,7-dimethyl-4-bora-3a,4a-diaza-s-indacene) derivatives (Molecular Probes)
ALEXA dyes (Molecular Probes). OREGON GREEN dyes (Molecular Probes)
JOE (6-carboxy-4',5'-dichloro-2',7'-dimethoxyfluorescein)
HEX (6-carboxy-2',4,4',5',7,7'-hexachlorofluorescein)
TET (6-carboxy-2',4,7,7'-tetrachlorofluorescein)
Cyanine dyes (Amersham Pharmacia Biosciences)

Luminescence can also be induced in certain chemicals referred to as luciferins. Energetic molecules such as ATP supply chemical energy for catalytic activities of luciferase enzymes causing the luciferins to emit light. Reagents for both the bacterial luciferase system (*Vibrio harveyi* or *V. fischeri*) and the firefly luciferase system (*Photinus pyralis*) are available from a variety of commercial sources (e.g., Chem. Co; St. Louis, Mo.).

Preferably, the luminescent agent has a high quantum yield of fluorescence at a wavelength of excitation different from that used to perform the photocleavage. Upon excitation at such wavelengths, the agent is detectable at low concentrations either visually or using conventional luminescence detectors and fluorescence spectrometers. Electroluminescence, produced by agents such as ruthenium chelates and their derivatives, or agents that possess nitroxide groups and similar derivatives are preferred when extreme sensitivity is desired (J. DiCesare, et al., BioTechniques 15:152–59, 1993). These agents are detectable at the fentomolar ranges and below.

Application of an electric field will also induce a detectable response in certain chemicals due to a net electric charge which induces the substance to migrate in an electric field. Magnetism may also be a detectable property if a magnetized substance such as iron or another magnetized metal is or is associated with the detectable group.

Other forms of detectable physical properties include an identifiable electrical polarizability, electron spin resonance and Raman scattering. Agents may also undergo a chemical, biochemical, enzymatic, electrochemical or photochemical reaction such as a color change in response to external electromagnetic fields or the introduction of other substances. Such electromagnetic fields and substances may be a catalyst or another reactant molecule that allows for detection of the bioreactive agent or transforms the agent into a detectable group.

All of these labeling agents can be specifically detected using the appropriate detector or detection system such as a spectrometer or electrophoretic or chromatographic systems. At times, it may be preferable to have a visually discernable detection system such as one that will trigger a photoelectric cell or one that can be detected and recorded manually. Spectrometers including absorption and fluorescence spectrometers are very sensitive detectors of specific energy of absorptions or emissions from many detectable groups. Detection and sorting of target may be automated as in the case of fluorescence activated cell sorters (FACS) which detect and isolate cells that possess a fluorescent label. Targets may be detected and sorted manually as can be done quite simply with magnetized conjugates using a magnet.

Additional physical properties which can be easily and accurately detected include chromaticism (e.g., violet=about 400–430 nm, blue=about 450–500 nm, green=about 550 nm, yellow=about 600 nm, orange=about 650 nm, red=about 700–750 nm), electromagnetic absorbance, enzyme activity or the ability to specifically bind with a coupling agent. Useful coupling agents include biotin, avidin, streptavidin, nucleic acids, nucleic acid and lipid binding proteins, haptens, antibodies, receptors, carbohydrates, immunogenic molecules, and derivatives and combinations thereof. The detectable group may have a combination of these properties allowing its selection from a wide variety of background materials. Some examples of the chemical structures of photocleavable agents of the invention are depicted in FIGS. 12, 13 and 14A–F.

4. Biotin and Biotin Derivatives as Affinity Groups

Another embodiment of an affinity group is biotin or biotin derivatives. Biotin-containing bioreactive agents may be photocleavable and are referred to herein as photocleavable biotins or PCBs. The binding between the egg-white protein avidin, a tetrameric protein found in avian eggs with the water soluble vitamin, biotin, is one of the strongest interactions known in biology having an association constant ($K_a$) of about $10^{15}$ $M^{-1}$, exceeding that of antibody-antigen interactions (M. Wilchek and E. A. Bayer, Methods Enzymol. 184, 1990). The bacterial counterpart to avidin is streptavidin, found in *Streptomyces avidinii*, which is slightly more specific for biotin than avidin. This strong interaction, along with the ability to covalently link biotin to a variety of substrates including proteins, nucleic acids, lipids, and receptor ligands such as neuropeptides and hormones, has resulted in a vast array of uses for these coupling agents all of which can be improved or enhanced with the use of PCB.

A wide variety of biotinyl groups can be used to form a PCB molecule. Biotin ($C_{10}H_{16}N_2O_3S$) has a molecular weight of 244.31 daltons and is comprised of a ring linked to an alkyl chain terminated by a carboxyl group. Numerous modifications can be made to the biotin group which involve changes in the ring, spacer arm and terminating group, all of which still exhibit a high affinity for streptavidin, avidin and their derivatives. Examples of photocleavable biotins that can be designed based on various photoreactive groups are depicted in FIG. 1.

The detection and isolation of chemical, biochemical and biological materials using the interaction between biotin and streptavidin is normally based on the immobilization of avidin or streptavidin to a surface (e.g., membranes, gels, filters, microtiter wells, magnetic beads). To that surface is applied a solution containing biotin coupled to targets which then bind to the streptavidin-coated surface. Biotin-containing target molecules can be isolated and non-biotinylated components washed away. Alternatively, biotinylated target molecules can be separated from a heterogeneous mixture using streptavidin-containing affinity columns. Biotinylated macromolecules including nucleic acids (DNA or RNA), proteins and protein-containing complexes, and even cells whose surface has been biotinylated or bound to a biotinylated antibody can be detected and isolated with these techniques.

As stated, biotin can be coupled to a wide variety of molecules including proteins, carbohydrates and nucleic acids. The availability of biotin derivatives has expanded this range even further. For example, biotin derivatives have been prepared with functionalities which are reactive towards amines, phenols, imidazoles, aldehydes, carboxylic acids and thiols. Biotin can also be incorporated into proteins, DNA and RNA by first attaching the biotin to building blocks of macromolecules such as amino acid or nucleotides which can be directly attached to these molecules or incorporated during their synthesis by chemical or enzymatic means.

5. Photoreactive Groups

One component of the bioreactive agent is the photoreactive group (PR). The photoreactive group is a chemical group capable of forming one or more covalent bonds with a substrate which can be cleaved with electromagnetic radiation (in some embodiments, photocleavable biotin (PCB) may function as a PR group). These bonds may be formed with a chemical group on the substrate such as, for example, an amine, phenol, imidazole, aldehyde, carboxylic acid or thiol. The photoreactive agent is a substituted aromatic ring containing at least one polyatomic group and, optionally, one or more monoatomic groups. The aromatic ring is preferably a five or six-membered ring. The substitutions comprise the polyatomic and optional monoatomic groups. The polyatomic group imparts electron channeling properties to attract or repel electrons to certain locations within the chemical structure, thereby creating or establishing the conditions to create the selectively cleavable covalent bonds. Some monoatomic groups such as halides can adjust the frequency or wavelength of the electromagnetic radiation which will induce cleavage. As such, monoatomic groups fine tune the cleavage event to sensitize conjugates to predetermined frequencies or intensities of radiation.

a. Photocleavable Biotin (PCB)

In some embodiments, the PR is photocleavable biotin (PCB). Unlike conventional biotins, photocleavable biotins enable one to release or elute the bound substrate from the immobilized avidin, streptavidin or their derivatives in a completely unmodified form. In some embodiments, PCBs may be the PR (photoreactive) portion in the general formulas A-PR-L-PRG and A-L-PR-PRG.

Photocleavable biotins are an important improvement over existing biotins for a number of reasons. Biotinylation of the target material can impede its subsequent use or characterization. Biotinylation of a protein can alter its activity, electrophoretic mobility, ability to bind a substrate, antigenicity, ability to reconstitute into a native form and ability to form multi-subunit complexes. In contrast, using photocleavable biotin, once the biotin is photocleaved from the protein or protein/binding complex, all the native properties and function will be restored to its native form for further use and characterization. Listed in Table 2 are some of the substrates to which a photocleavable agent such as PCB can be linked.

TABLE 2

Chemical linkage of Photocleavable Biotins with different molecules

| Molecule or Assemblage | Functional Group on the Molecule | Reactive group on the PCB | Resulting linkage and reaction conditions |
|---|---|---|---|
| Amino acids, proteins, enzymes or antibodies | Amino group or R—NH2 | NHS-ester | Amide linkage |
| Amino acids, proteins, enzymes or antibodies | R—OH | chloroformate carboxylic acid | Ester linkage |
| Amino acids, proteins, enzymes or antibodies | R—COOH | Reaction with parent alcohol (DCC coupling) | Ester linkage |
| Nucleotides, RNA or DNA molecules | Aromatic amines | chloroformate | Amides |
| Carbohydrates RNA for ribonucleotides | Sugar hydroxy R—OH | chloroformate | Ester linkage |
| Nucleotide phosphoramidites | Phosphate groups | diazoethane | Phosphate ester |
| Lipids/ Phosphatidyl serine | R—NH2 | Chloroformate NHS-ester | amide |
| Carbohydrates | Sugar hydroxyl | Chloroformate | Ester linkage |

There are a number of chemical groups available in bioreactive agents and conjugates of the invention. For example, an NHS-ester functionality introduced in PCB is highly reactive and can selectively react with aliphatic amino groups that are present in proteins. Another example is a phosphoramidite group which is highly reactive and can selectively react with hydroxyl groups of nucleic acids. In cases where chemical groups like carboxyl (—COOH) or phosphate groups need modification, a precursor of PCB in the form of the parent alcohol can be used to form appropriate ester-type linkages. These derivatives can be chemically linked to a variety of macromolecules and molecular components including amino acids, nucleotides, proteins and polypeptides, nucleic acids (DNA, RNA, PNA [peptide nucleic acid]), lipids, hormones and molecules which function as ligands for receptors.

The application of biotin-avidin technology for the detection and isolation of chemical and biological materials has also been broadened by the use of binding molecules which are first biotinylated and then allowed to selectively interact with the target molecule to be isolated. Isolation of the target molecule or cell is facilitated by the binding of the biotinylated binding-complex to the streptavidin-containing column or streptavidin-coated magnetic beads. Binding molecules include antibodies which selectively bind to specific antigens, DNA probes which selectively bind to specific DNA sequences and ligands which selectively bind to specific receptors. This approach has been used to isolate a wide variety of macromolecules and cells (Tables 2 and 3). However, such isolation methods require that the biotinylated target be released from the bound streptavidin. Disruption of this bond typically requires non-physiological conditions such as low pH and high concentration of guanidinium-HCl which is usually damaging for the target molecule or cell. Even after disruption of the streptavidin-biotin interaction, the target or binding molecule remains partially or completely biotinylated which can interfere with later uses. Further, elution conditions are non-physiological and can also be disruptive to the target molecule or cell. In contrast, using photocleavable biotins substrate can be quickly and easily cleaved from biotin with little to no effect on substrate conformation or activity.

The use of PCB in any of the usual detection and purification procedures, including those discussed above, represents a significant savings of time, energy and ultimately cost. In addition, a variety of derivatives of avidin and streptavidin are commercially available which have been modified through chemical or genetic means. These same derivatives can be used with PCB. One example is ImmunoPure NeutrAvidin sold commercially (Pierce Chemical; Rockford, Ill.). This protein is a modified avidin derivative which has been deglycosylated and does not contain the RYD domain that serves as a universal recognition sequence for many cell receptors. Non-specific adsorption to other proteins and cell surfaces is greatly reduced.

Figure 2:
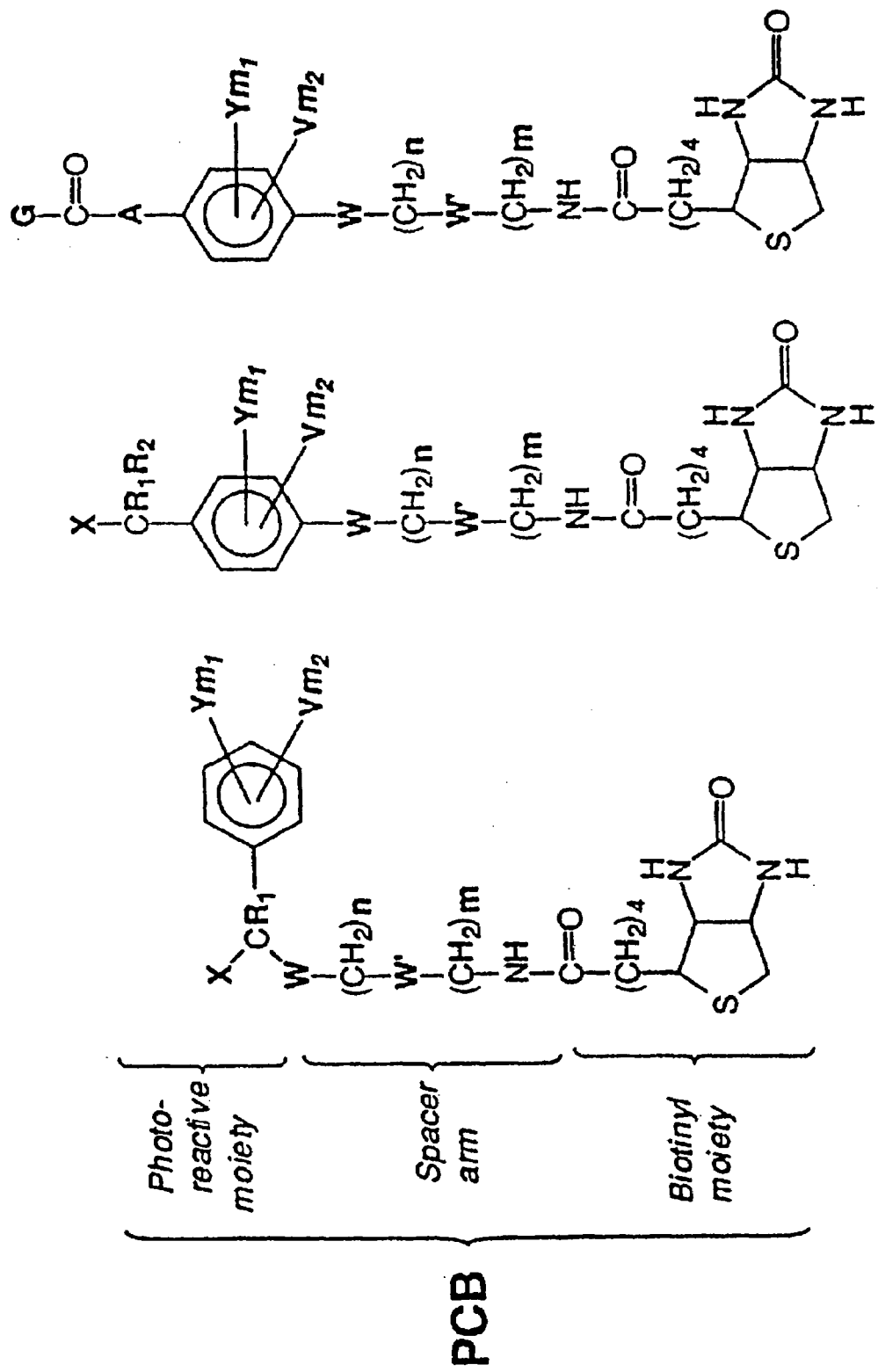
FIG. 2 shows a schematic representation of one embodiment of photocleavable biotin.

In one embodiment, the major molecular elements of a photocleavable biotin (PCB) are a photoreactive group and a biotinyl group which constitutes the detectable group (FIG. 2). The photoreactive group and the biotinyl group are linked together with a spacer arm to form the PCB molecule. The photoreactive group contains a five or six membered ring derivatized with functionalities represented by X, Y and A-C(O)-G, wherein X allows linkage of PCB to the biomolecular substrate. In the preferred embodiment, Y represents a substitution pattern on a phenyl ring containing one or more substituents such as nitro or alkoxy groups. The functionality W represents the group that allows linkage of the cross-linker group to the photoreactive group. The purpose of the spacer arm is to increase the access of the biotin group for effective interaction with streptavidin, and thus, increase the binding efficiency. Typically these can be constructed using either long alkyl chains or using multiple repeat units of caproyl groups linked via amide linkages.

Choice of photoreactive group, spacer arm and the biotinyl group depends on the target substrate including amino acids, proteins and fragments thereof, antibodies, nucleotides, DNA or RNA, lipids, carbohydrates and cells to which the photocleavable biotin is to be attached. It also depends on the exact conditions for photocleavage and the desired interaction between the biotinyl group and streptavidin, avidin or their derivatives. Some of the various choices for the photoreactive group and linker arms for PCB are shown in FIG. 1.

b. 2-Nitrobenzyl Derivatives

Figure 3:
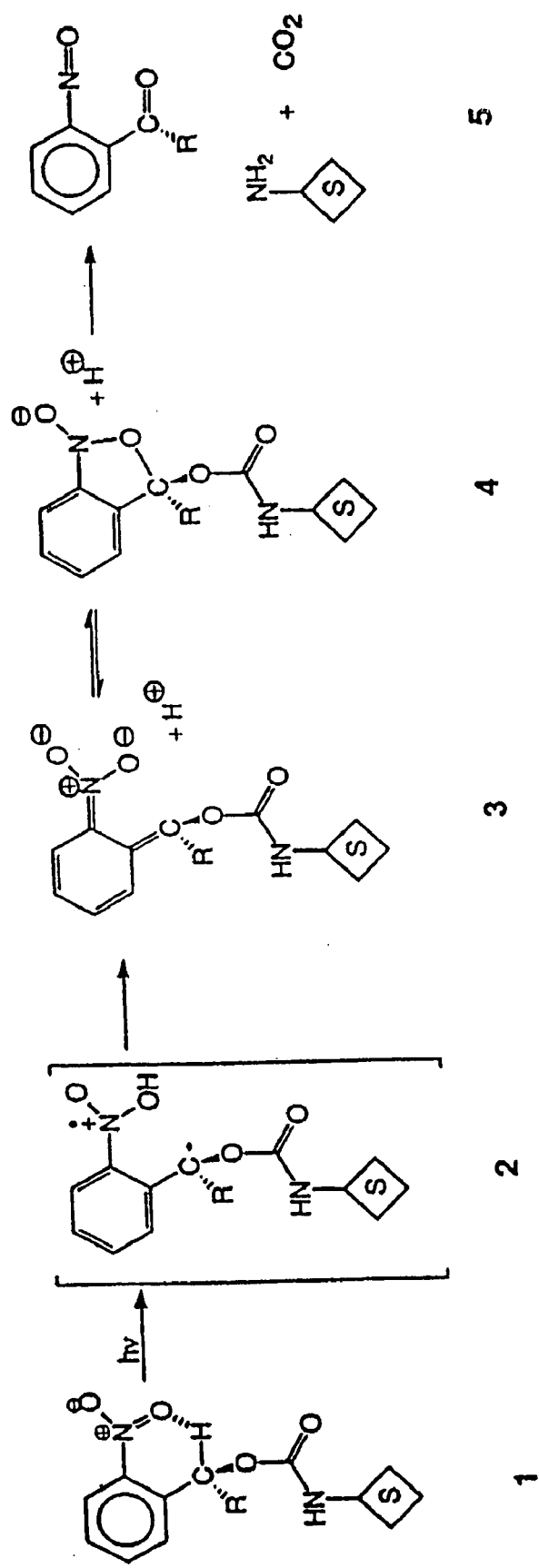
FIG. 3 shows a mechanism of photocleavage in 2-nitrobenzyl-based systems.

One class of photoreactive groups are 2-nitrobenzyl derivatives. In their ground state, 2-nitrobenzyl-based agents and conjugates have an intramolecular hydrogen bond between benzylic hydrogen and the ortho nitro group (—CH . . . $O_2N$) (B. Brzezinski, et al., J. Chem. Soc. Perkin. Trans. 2:2257–2261, 1992). Upon illumination with wavelengths of greater than 300 nm, these chemical compounds transition to an excited state. Proton transfer reaction from benzylic carbon to the oxygen in nitro group takes place which is followed by electron rearrangement (FIG. 3). This reaction results in the formation of a transient species called an aci-nitro ion which is in a rapid equilibrium with a cyclic form. In the cyclic intermediate, electron rearrangement and oxygen transfer from nitrogen to benzylic carbon takes place resulting in the formation of 2-nitroso derivatives and release of a substrate which is a good leaving group (J. A. McCray, et al., Annu. Rev. Biophys. Chem. 18:239–70, 1989).

Figure 4:
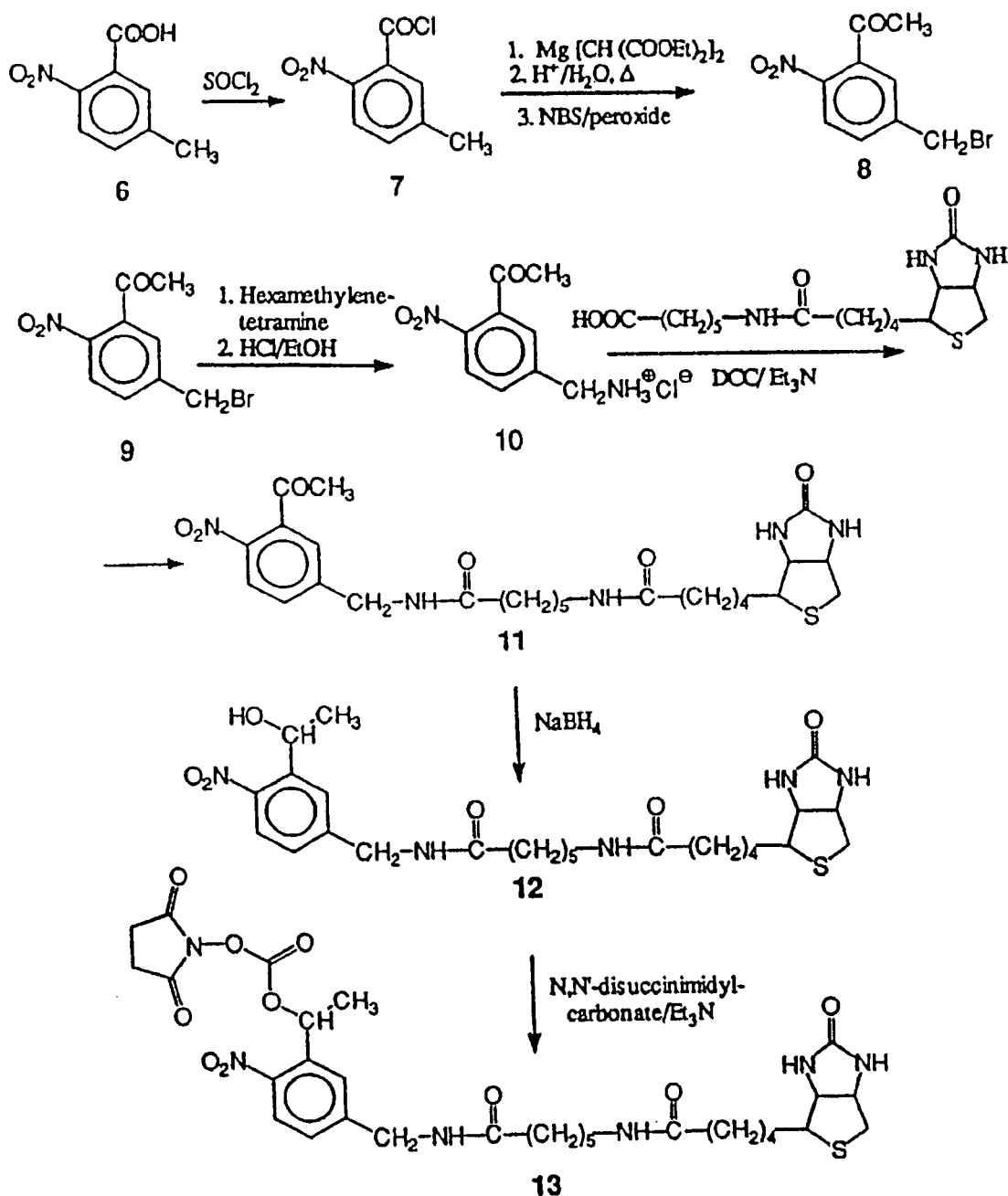
FIG. 4 shows one embodiment of a method of synthesis of photocleavable biotin.

Chemical synthesis of PCB NHS-ester involves three principal steps: (1) generation of the photoreactive group, for example, 5-methyl-2-nitroacetophenone; (2) generation of a suitable amino group and attachment to biotin containing spacer; (3) generation of hydroxyl groups and derivatization as N-hydroxysuccinimidyl carbonate (NHS-ester). These steps are schematically represented in FIG. 4.

Bioreactive agents can also be synthesized based on other photoreactive groups. Chemical syntheses of two other classes of photocleavable groups 3,5-5-dimethoxybenzyl and 2-nitrobenzenesulfenyl (FIG. 1) can be carried out using similar synthesis strategies. These 2-nitrobenzyl groups all contain a benzylic carbon-hydrogen bond ortho to a nitro group, which is necessary for their photolability. In the developments of these photoreactive groups as protecting groups, difficulties were encountered as the subsequent reactions of these carbonyl compounds resulted in formation of coupled azo compounds, which act as internal light filters (V. N. R. Pillai, Synthesis 1, 1980). These complications were overcome in the present invention with the use of alpha-substituted, o-nitrobenzyl compounds 6. Bioreactive Agent/Substrate Conjugates Another embodiment of the invention is directed to photocleavable conjugates comprising bioreactive agents photocleavably coupled to substrates. Conjugates have the property that they can be selectively cleaved with electromagnetic radiation to release the substrate. Substrates are those chemicals, macromolecules, cells and other substances which are or can be used as targets of the bioreactive agent. Substrates that are selectively cleaved from conjugates may be modified by photocleavage, but still retain functionally activity, or may be released from the conjugate completely unmodified by photocleavage. Substrates may be coupled with agents, uncoupled and recoupled to new agents at will.

In some embodiments, additional types of coupling agents include antibodies, antibody fragments and antigens. Antibodies have the advantage that they can bind to their respective antigen with great specificity. Substrates which are antigens can be detected by their ability to specifically bind to available antibodies or to antibodies which can be easily created. Useful antibodies or antibody fragments may be monoclonal or polyclonal and are preferable of the class IgG, but may also be IgM, IgA, IgD or IgE. Other preferred detectable groups include nucleic acids. Short sequences of RNA or DNA or oligonucleotides, preferably less than about thirty nucleotides in length and as short as four to ten nucleotides, can be detected by their ability to specifically hybridize with a complementary nucleic acid and detected directly or indirectly using PCR which greatly amplifies a specific sequence that is subsequently detected. In a similar fashion, binding proteins and receptor-ligand combinations are also useful as detectable labels.

Useful substrates are any chemical, macromolecule or cell that can be attached to a bioreactive agent. Examples of useful substrates include proteins, peptides, amino acids, amino acid analogs, nucleic acids, nucleosides, nucleotides, lipids, vesicles, detergent micells, cells, virus particles, fatty acids, saccharides, polysaccharides, inorganic molecules and metals. Substrates may also comprise derivatives and combinations of these substances such as fusion proteins, protein-carbohydrate complexes and organo-metallic compounds. Substrates may also be pharmaceutical agents such as cytokines, immune system modulators, agents of the hematopoietic system, recombinant proteins, chemotherapeutic agents, radio-isotopes, antigens, anti-neoplastic agents, enzymes, PCR products, receptors, hormones, vaccines, haptens, toxins, antibiotics, nascent proteins, synthetic pharmaceuticals and derivatives and combinations thereof.

Figure 5:
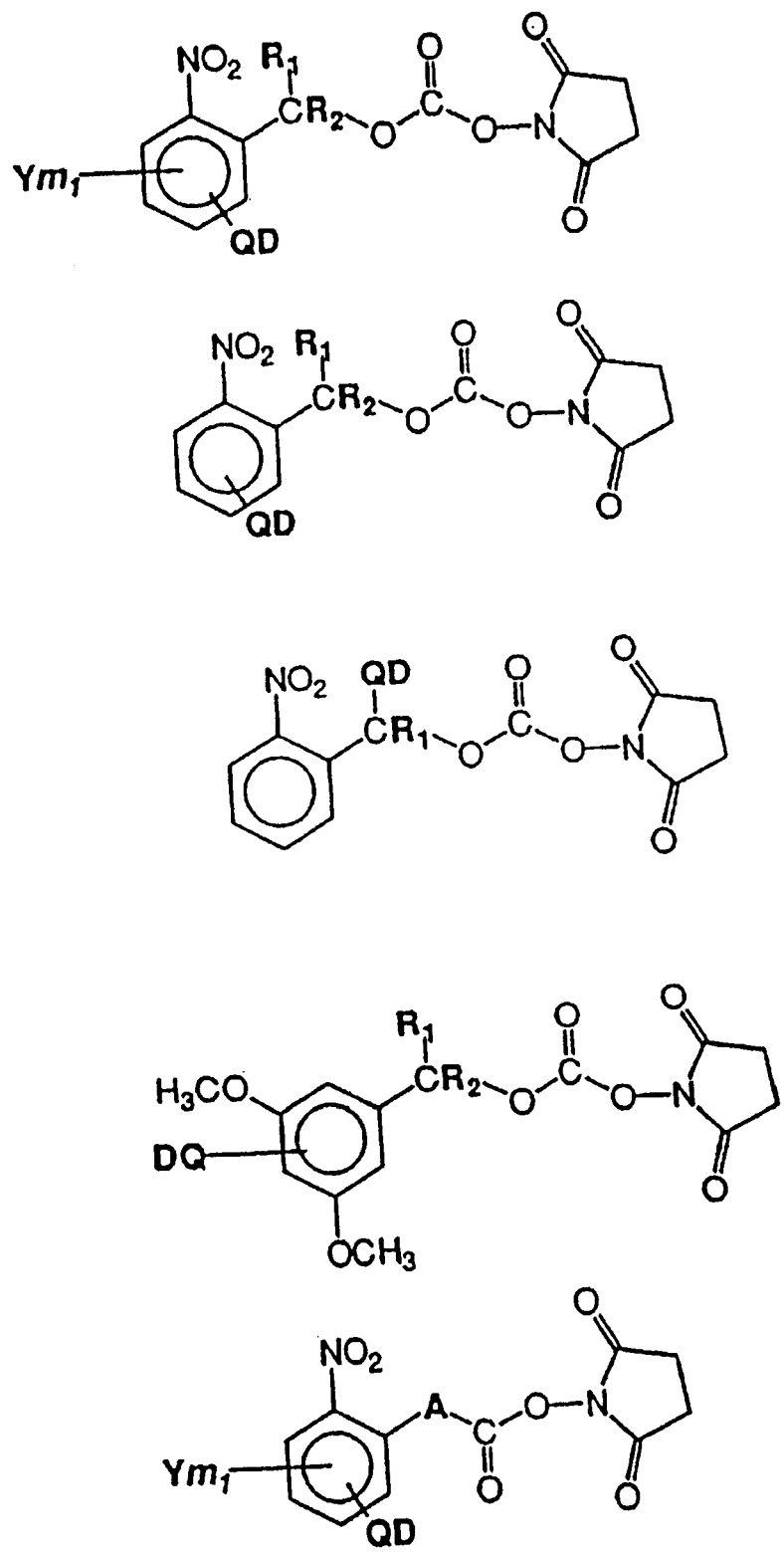
FIG. 5 shows various embodiments of photocleavable reagents.
Figure 6:
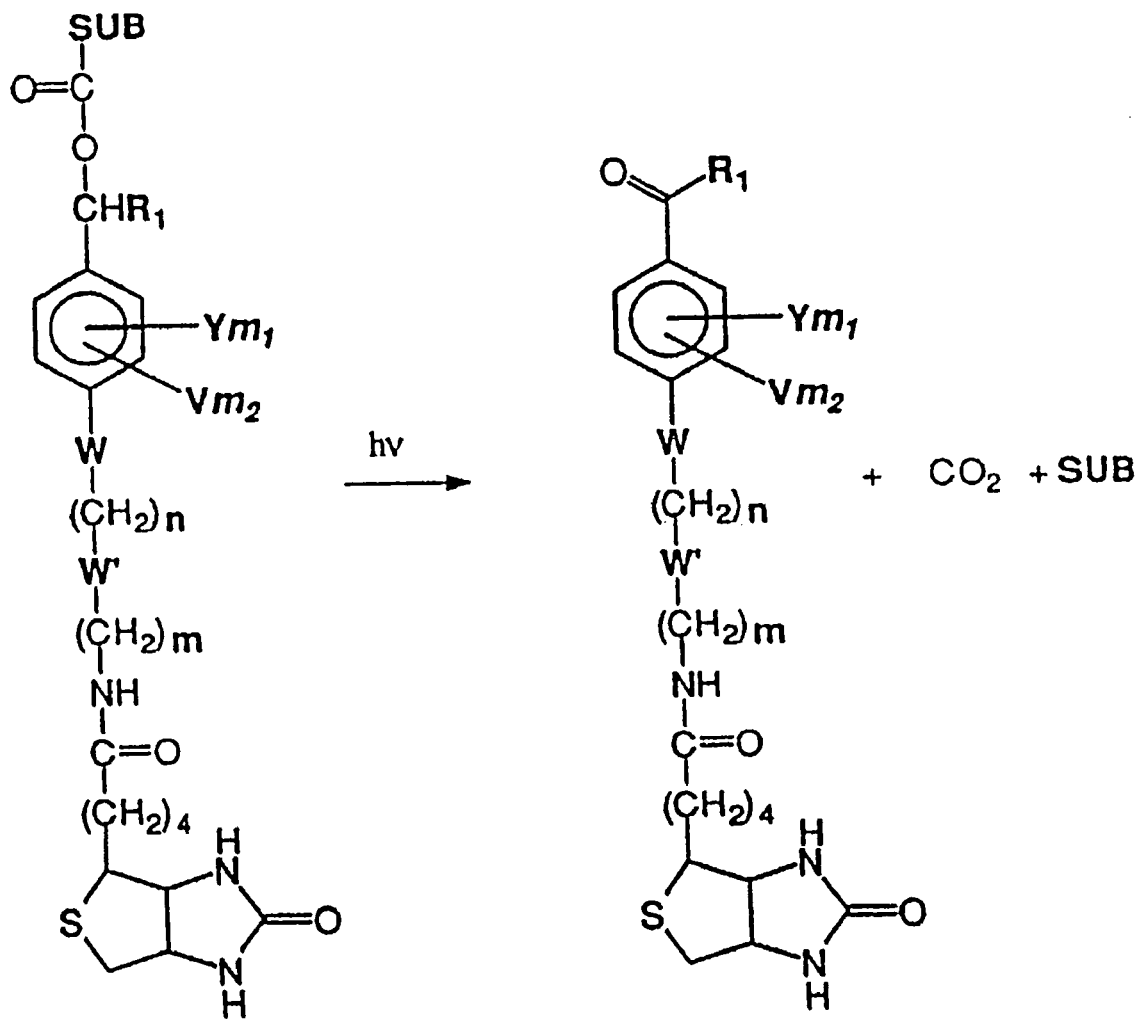
FIG. 6 schematically shows the photolysis of one embodiment of a PC-biotin.
Figure 7:
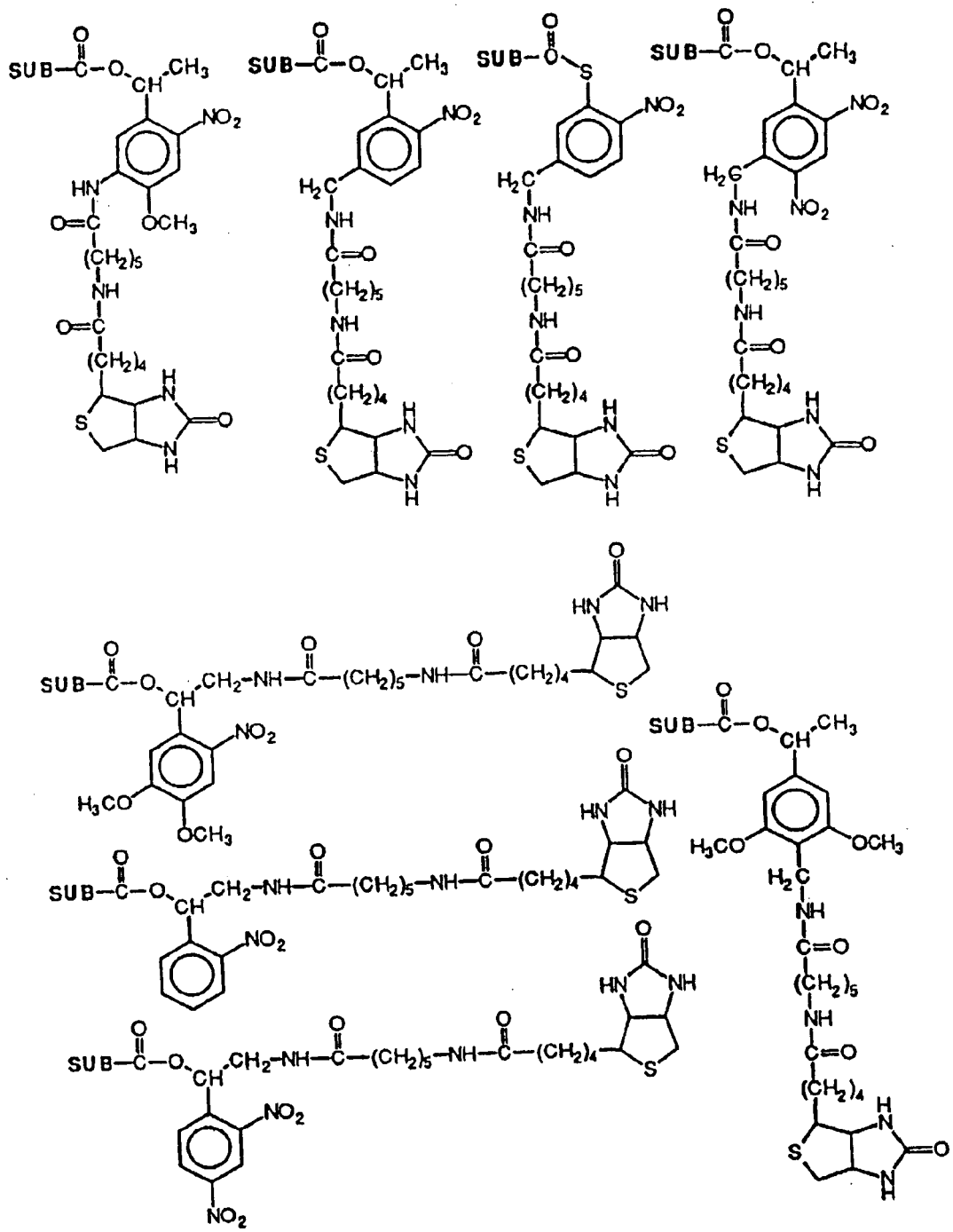
FIG. 7 shows embodiments of PC-Biotin conjugates.

Photocleavage of conjugates of the invention should preferably not damage released substrate or impair substrate activity. Examples of photocleavable agents are shown in FIG. 5. An example of Photocleavage is illustrated in FIG. 6. Example of PCB photoclevable conjugates are shown in FIG. 7. Proteins, nucleic acids and other protective groups used in peptide and nucleic acid chemistry are known to be stable to most wavelengths of radiation above 300 nm. PCB carbamates, for example, undergo photolysis upon illumination with long-wave UV light (320–400 nm), resulting in release of the unaltered substrate and carbon dioxide. The yield and exposure time necessary for release of substrate photo-release are strongly dependent on the structure of photoreactive group. In the case of unsubstituted 2-nitrobenzyl PCB derivatives the yield of photolysis and recovery of the substrate are significantly decreased by the formation of side products which act as internal light filters and are capable of reacting with amino groups of the substrate. In this case, illumination times vary from about 1 minute to about 24 hours, preferably less than 4 hours, more preferably less than two hours, and even more preferably less than one hour, and yields are between about 1% to about 95% (V. N. R. Pillai, Synthesis 1, 1980). In the case of alpha-substituted 2-nitrobenzyl derivatives (methyl, phenyl), there is a considerable increase in rate of photo-removal as well as yield of the released substrate (J. E. Baldwin, et al., Tetrahedron 46:6879, 1990; J. Nargeot, et al., Proc. Natl. Acad. Sci. U.S.A. 80:2395, 1983).

The choice of a particular bioreactive agent depends on which molecular groups of the substrate are to be derivatized. For example, reaction of photocleavable biotin NHS-ester with a protein results in formation of a covalent bond with primary amino groups such as at the epsilon-position of lysine residues or the alpha-NH2 group at the N-terminal of a protein. Normally, a number of lysine residues are exposed on the surface of a protein and available for such reaction. Alternatively, several other photocleavable biotins can be used which react with hydroxyl groups (—OH) present in tyrosine, threonine and serine residues, carboxyl groups (—COOH) present in aspartate and glutamate residues, and sulfhydryl groups (—SH) present in cysteine residues (Table 2). Thus, a wide variety of groups are available which are likely to be on the surface of a target protein.

Attachment of photocleavable biotin to molecules which bind proteins such as receptor ligands, hormones, antibodies, nucleic acids, and proteins that bind glycoproteins can also be accomplished because of the wide variety of reactive groups available for photocleavable biotins. For example, photocleavable biotin can be conveniently linked to antibodies which are directed against a particular protein. Alternatively, photocleavable biotins can be linked to DNA and RNA or to a variety of small molecules including receptor ligands and hormones. The importance of biotinylation of binding-complexes for isolation of proteins such as membrane receptors and splicesomes has already been demonstrated using conventional biotins or non-photocleavable biotins.

7. Detectable Groups and Uses Thereof

In some embodiments, the present invention contemplates that the bioreactive agents of the present invention comprise detectable groups. The choice of the detectable group depends on the substrate, its environment and the desired method of detection and isolation. For example, a substrate present in low concentrations may require a sensitive method of detection such as fluorescent spectroscopy thereby requiring a fluorescent group such as coumarin. The wavelength of fluorescent emission can be selected by the choice of detectable group so as not to interfere with any natural fluorophores which may be present in the mixture. In cases where rapid isolation of the substrate is desired, choice of the detectable group may be determined by the availability of a suitable coupling agent. For example, an antigen which serves as the detectable group may be used if a suitable antibody is available. Since the detectable group, the reactive group and the photoreactive groups are chemically separate in the bioreactive agent, the properties of each can be adjusted to meet the multiple requirements for detection and isolation of a particular substrate. Affinity label groups, linker groups, photoreactive groups (i.e., photocleavable groups) and protein reactive groups may function as or be modified to function as detectable groups. Additionally, detectable groups may be added (e.g., via covalent bonds) to any of the aforementioned groups. A preferred detectable group is a linker group wherein the linker group has been modified to comprise isotopic modifications, for example, the substitution of hydrogen ion with deuterium ions.

Conjugates of the invention may be attached to a solid support via the detectable group (e.g. via a biotin-avidin interaction), the substrate or any other chemical group of the structure. The solid support may comprise constructs of glass, ceramic, plastic, metal or a combination of these substances. Useful structures and constructs include plastic structures such as microtiter plate wells or the surface of sticks, paddles, beads or microbeads, alloy and inorganic surfaces such as semiconductors, two and three dimensional hybridization and binding chips, and magnetic beads, chromatography matrix materials and combinations of these materials 8. Exemplary Uses of Conjugates of the Present Invention Another embodiment of the invention is directed to conjugates which are pharmaceutical compositions. Compositions must be safe and nontoxic and can be administered to patients such as humans and other mammals. Composition may be mixed with a pharmaceutically acceptable carrier such as water, oils, lipids, saccharides, polysaccharides, glycerols, collagens and combinations thereof and administered to patients.

Pharmaceutical compositions with photo-releasable substrates are useful, for example, for delivery of pharmaceutical agents which have short half-lives. Such agents cannot be administered through current means without being subject to inactivation before having an effect. Pharmaceutical agents in the form of conjugates, covalently bound to bioreactive agents, are more stable than isolated agents. After general administration of the composition to the patient, the site to be treated is exposed to appropriate radiation releasing substrate which produces an immediate positive response in a patient. Uncoupling from the bioreactive agent at the point of maximal biological effect is an advantage unavailable using current administration or stabilization procedures. In an analogous fashion, other areas of the patients body may be protected from the biological effect of the pharmaceutical agent. Consequently, using these conjugates, site-directed and site-specific delivery of a pharmaceutical agent is possible.

Another embodiment of the invention is directed to a method for isolating targets from a heterologous mixture. Bioreactive agents are contacted with the mixture to react with target forming the conjugate. Alternatively, conjugates can be contacted with the heterologous mixture to couple substrate within the conjugate to one or more targets. Conjugates can be separated from the mixture by any currently available techniques (e.g., Table 3).

TABLE 3

Affinity Techniques Using Avidin

| Material | Method of Separation |
| --- | --- |
| Magnetic beads coated with Streptavidin | Magnetic separation |
| Beads coated with Streptavidin | Washing (e.g., centrifugation) and elution |
| Biotinylated Antibodies | Immunoprecipitation |
| Cross-linked-bisacrylamide/azolactone copolymers with avidin | Column Chromatography |
| Agarose coated with Streptavidin | Column Chromatography |

Procedures such as chemical or physical separation of components of the mixture, electrophoresis, electroelution, sedimentation, centrifugation, filtration, magnetic separation, chemical extraction, affinity separation methods such as affinity chromatography or another chromatographic procedure such as ion-exchange, gradient separation, HPLC or FPLC, and combinations of these techniques are well-known and allow for a rapid isolation with a high efficiency of recovery (e.g., M. Wilchek, et al., Methods Enzymol. 184, 1990; M. Wilchek, et al., Anal. Biochem. 171:1, 1988). After separation or isolation, targets can be easily quantitated using available methods such as optical absorbance or transmission (e.g., nucleic acid, proteins, lipids) or the Bradford (M. Bradford, Anal. Biochem. 72:248, 1976) or Lowry (O. Lowry, et al., J. Biol. Chem. 193:265, 1951) assays (e.g., proteins), both of which are commercially available. After separation, are treated with electromagnetic radiation to release substrate. The substrate targets can than be separated from the released bioreactive agent, if desired, to obtain substantially or completely pure targets.

Targets (i.e., substrates) which can be detected and isolated in a highly purified form by this method include nearly any chemical, molecule or macromolecule including immune system modulators, agents of the hematopoietic system, cytokines, proteins, hormones, gene products, antigens, cells including fetal and stem cells, toxins, bacteria, membrane vesicles, virus particles, and combinations thereof. Detection and isolation are determined by the ability of the bioreactive agent to bind substrate. For example, nucleic acids can be base-paired to complementary nucleic acids, to nucleic acid binding proteins or to chemical groups which react specifically with chemical groups found on nucleic acids. Proteins can be bound with monoclonal or polyclonal antibodies or antibody fragments specific to those proteins, or chemical groups which react specifically with chemical groups found on the proteins of interest. Substrates may be, for example, precursors of targets such as one or more of the naturally or non-naturally occurring amino acids wherein the target is a nascent protein, or one or more ribonucleotides, deoxyribonucleotide or primers when the target is a nucleic acid. Precursor can be incorporated into target molecules by, for example, in vivo or in vitro replication, transcription or translation. Target may be a protein or protein-containing complex, nucleic acid, gene sequence or PCR product. Substrates may also be receptors which bind to or otherwise associate with ligands specific for the receptor molecules. Receptors which can be isolated include cytokines wherein the target is a cytokine receptor and antigens wherein the target is an antibody. Preferred conjugates for the detection and isolation of a target from a heterologous mixture are photocleavable biotins linked to antibodies (polyclonal, monoclonal, fragments), photocleavable coumarins linked to antibodies, photocleavable dansyls linked to lipids and derivatives and modifications thereof.

The heterologous mixture which contains target may be a biological sample, any proteinaceous composition such as a cellular or cell-free extract, nucleic acid containing compositions, a biomass containing, for example, vegetative or microbial material, a cell culture of primary or immortalized cells, lipid vesicles or even animals. Animals may be used to detect targets which may be present in the body or parts of the body or, alternatively, to collect and isolate targets such as macromolecules or cells from animal models. Substrate can also be proteins, peptides, amino acids, amino acid analogs, nucleosides, nucleotides, lipids, vesicles, detergent micells, fatty acids, saccharides, polysaccharides, inorganic molecules, metals and derivatives and combinations thereof.

In an application of this method, the substrate may be an integral component of the target such as a nucleotide in the detection and isolation of nascent nucleic acids or an amino acid in the detection and isolation of nascent proteins. Substrate is incorporated into target by chemical or enzymatic techniques and detected and isolated by the presence of the detectable group. Briefly, conjugates are contacted with reagents in a heterologous mixture such as, for example, in a replication, transcription, translation or coupled transcription/translation system. Substrates are incorporated into targets through the action of components in the system such as enzymes, precursor molecules and other reagents of the system. Conjugate coupled targets are separated from the mixture and treated with electromagnetic radiation to release the target which is then isolated.

Conjugates can be contacted with a heterologous mixture by incubation as in, for example, the enzymatic incorporation of a macromolecular precursor into a nascent macromolecule which may be either in vivo or in vitro. Nucleic acid polymerases will incorporate precursor nucleotides or nucleic acid primers into nucleic acids. In vitro incubations in cell-free reaction mixture are typically performed at a temperature of between about 4° C. to about 45° C., preferably at between about 12° C. to about 37° C., and more preferably at about room temperature (RT). Incubation of conjugates into nascent macromolecules may be complete in about 5 minutes, about 15 minutes, or about one hour depending on the incubation conditions, or may require two, three or more hours to complete. When the heterologous mixture is an animal or an animal model, in vivo incubations are generally performed at body temperature and may require hours or days for conjugates to distribute to areas of the animals body which may be remote from the site of introduction, for conjugates to react with targets and for conjugates coupled with targets to be collected.

One of the preferred embodiments of the invention relates to the detection or isolation of protein using an affinity group. In one application of this embodiment, the affinity group is reacted with a protein or other molecule through the formation of covalent bonds with specific chemicals groups of the protein forming a conjugate. The protein may be either the target to be isolated or detected or a probe for the target protein such as an antibody. The target protein can then be isolated using affinity methodology.

Figure 8:
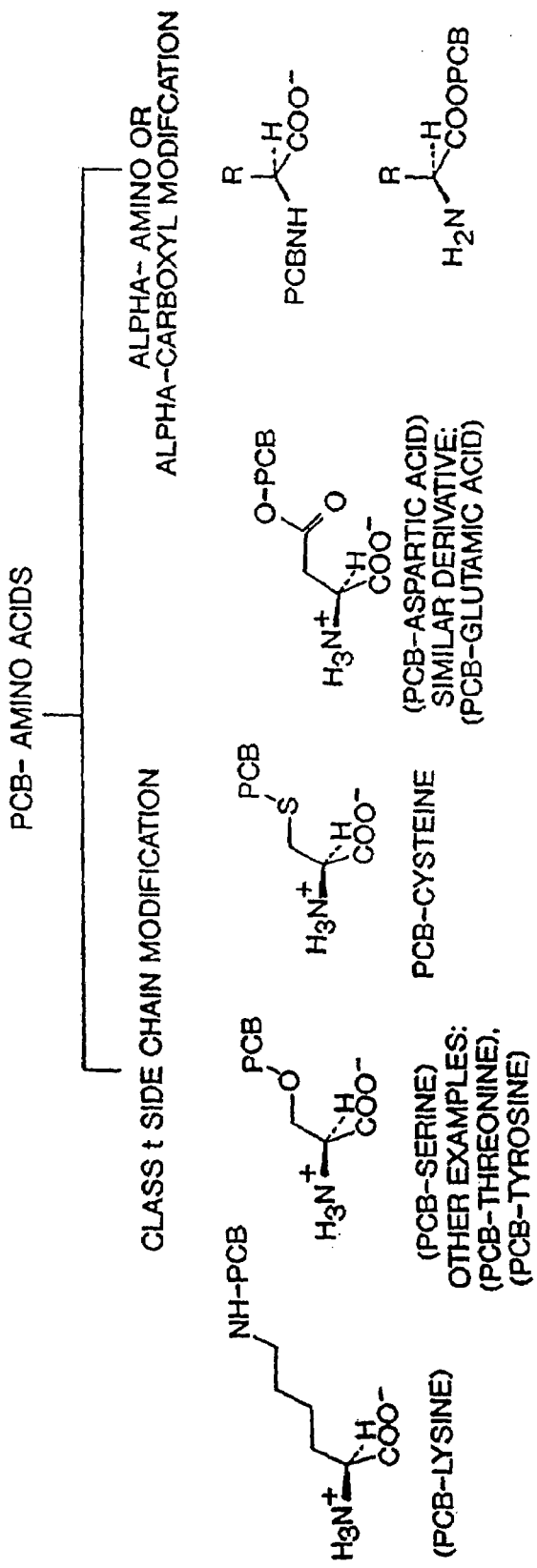
FIG. 8 shows possible amino acid linkages of PCB.

The affinity group is attached to an amino acid using, for example, the side-chain groups such as an amino group (lysine), aliphatic and phenolic hydroxyl groups (serine, threonine and tyrosine), sulfhydryl group (cysteines) and carboxylate group (aspartic and glutamic acids) (FIG. 8). Synthesis can be achieved by direct condensations with appropriately protected parent amino acids. For example, lysine side chain amino group can be modified by modification of the epsilon-amino group.

After attachment of the affinity group on to a protein, protein fragment, protein-complex or other amino acid-containing target, the target is isolated using a simple four step procedure (FIG. 9). First, a bioreactive agent is synthesized. Second, a substrate is coupled to the bioreactive agent forming a conjugate. Third, the conjugate is separated from other materials in the mixture through the selective interaction of, for example, the photocleavable biotin with avidin, streptavidin or their derivatives. Captured substrates may be immobilized on a solid support such as magnetic beads, affinity column packing materials or filters which facilitates removal of contaminants. Finally, affinity group is detached from the substrate by illumination of a wavelength which causes the photoreactive group linkage to be broken. Substrates are dissolved or suspended in solution at a desired concentration. In those situations wherein conjugate coupled targets are not attached to solid supports, release of substrates can be followed by another magnetic capture to remove magnetic particles now containing bound affinity group. Thus, a completely unaltered protein (i.e., substrate) is released in any solution chosen, in a purified form and at nearly any concentration desired.

In a preferred embodiment of the invention, the methodology, for isolation and detection of PCR products and translated proteins thereof, can be applied to diagnostic assays of a variety of diseases, the detection of mutations as well as to the identification of unique DNA sequences and translated proteins thereof. For example, serological assays such as Western blots and immunofluorescence and radioimmunoprecipitation assays provide a rapid and sensitive procedure to screen for the presence of antibodies to HIV-1. Further, in current PCR-based analysis, highly conserved regions of the viral genomes are targeted for amplification and involve hybridization using 32P-labeled oligomer probes in solution to one strand of an amplified product. These tests can be used only for the direct detection of the virus. A useful assay for the detection of HIV would detect not only active virus, but also the presence of latent virus which has not yet expressed its genome, but is still present in cells by detection of viral proteins and fragments thereof. This would allow determination of both latent and actively replicating virus. This would be particularly useful in newborns where maternal antibodies can interfere with serological tests.

Another embodiment of the invention is directed to substrates isolated by the above method which may be utilized in pharmaceutical compositions to treat or prevent diseases and disorders. Pharmaceutical compositions may comprise the isolated substrates plus a pharmaceutically acceptable carrier such as water, oils, lipids, saccharides, polysaccharides, glycerols, collagens or combinations of these components. The composition is administered to patients for the treatment or prevention of certain diseases and disorders and for the site-directed administration of pharmaceutical agents.

Another embodiment of the invention is directed to a method for determining, for example, an in vivo half-life of a protein-based pharmaceutical in a patient. Conjugates are formed by coupling the pharmaceutical to a bioreactive agent via a covalent bond that can be selectively cleaved with electromagnetic radiation. Conjugates are administered to the patient after which, two or more biological samples are removed. Samples are treated with electromagnetic radiation to release the pharmaceutical from the bioreactive agent, the amount of the bioreactive agent in the biological samples is determined, and the in vivo half-life of the pharmaceutical determined.

The pharmaceutical may be a composition comprising cytokines, immune system modulators, agents of the hematopoietic system chemotherapeutic agents, radio-isotopes, antigens, anti-neoplastic agents, recombinant proteins, enzymes, PCR products, nucleic acids, hormones, vaccines, haptens, toxins, antibiotics, nascent proteins, synthetic and recombinant pharmaceuticals, and derivatives and combinations of these components. Conjugates may be administered to patients by parenteral administration, sublingual administration, enteral administration, pulmonary absorption, topical application and combinations thereof animals which can be tested include mammals such as humans, cattle, pigs, sheep, dogs, cats, horses and rodents. Biological samples which are collected can be sample of peripheral blood, blood plasma, serum, cerebrospinal fluid, lymph, urine, stool, ophthalmic fluids, organs and bodily tissues.

Another embodiment of the invention is directed to the controlled release of a substrate into a medium. Conjugates comprised of a bioreactive agent coupled to the substrate by a covalent bond which can be selectively cleaved with electromagnetic radiation are created as described. These conjugates are bound to a surface of an article and placed into the medium. The surface of the article is exposed to a measured amount of electromagnetic radiation and the substrate released into the medium to carry out a beneficial effect. Alternatively, an article may be placed at a selected site and the conjugates, having an affinity for the article, are administered at a distal site. Conjugates then migrate to the selected site and perform an intended function. After completion of that function, radiation is applied and the substrate is released from the fixed bioreactive agents. Released substrate may be naturally eliminated from the patients system. This can be highly useful, for example, in radiation therapy for cancer patients.

Preferred are radiation wavelengths which can penetrate the medium. Depending on the amount and frequency of radiation exposure, release can be controlled and continued over a period of time. This method is useful for the controlled and site-directed administration of pharmaceutical compositions to a patient. In such cases, the medium in which the article is placed may be blood, lymph, interstitial fluid or a tissue. Controlled release may also be performed in tissue culture for administering a constant or periodic amount of a substrate to a cell culture fluid or balanced salt solution for uptake by the cells. Articles which may be coupled with substrate and placed within or adjacent to a patients body include articles comprising carbohydrates, lipids, proteins, polysaccharides, cellulose, metals including magnets, organic polymers and combinations thereof.

Alternatively, articles containing conjugates or bioreactive agents can be placed into the site of the disorder, such as a tumor. The pharmaceutical agent such as, for example, a radioactive agent is administered to the patient and becomes bound to the fixed conjugates or agents. Effects attributable to the pharmaceutical agent are localized. The article is exposed to a measured amount of electromagnetic radiation and the pharmaceutical agents released into the body and excreted. This method is preferred when only a short term exposure of the pharmaceutical agent is desired or to efficiently remove potentially harmful agents after they have had their desired effects.

Another embodiment of the invention is directed to a method for detecting a target molecule, e.g., a protein or protein fragment, in a heterologous mixture. Conjugates are formed by coupling a substrate to a bioreactive agent with a covalent bond that is selectively cleavable with electromagnetic radiation. For example, bioreactive agents are contacted with the heterologous mixture to couple to substrate(s). Uncoupled bioreactive agents are removed and the coupled conjugate are treated with electromagnetic radiation to release the substrate. In some embodiments, the presence of target molecules can be detected by detecting the presence of the detectable group, if present. Substrate macromolecules may be proteins and peptides and fragments thereof or conjugates comprising proteins, peptides and fragments thereof. Once coupled, substrate (macro)molecules can be isolated and the amount isolated quantitated by current any of the techniques available to those of ordinary skill in the art, for example, by mass spectrometry.

In another application of the invention, detection of pathogens such as microorganisms from biological material often requires their isolation and culturing. The more effective the isolation step, the more reliable and rapid the culturing step will be because of the elimination of other contaminants and the concentration of the target pathogen. While a variety of affinity techniques exists for separation of microorganisms such as magnetic beads conjugated to selective antibodies, the problem of release of the microorganisms in a viable form suitable for culturing and sensitive detection still remains. In contrast, the bioreactive agents of the present invention provide a non-damaging and rapid means for photochemical release of the microorganism in a viable form.

For example, this application of the invention provides the basis for development of rapid diagnostic assays for a variety of pathogens involved in human and animal disease that were previously not possible using conventional technology. Microorganisms could also be isolated from food, milk, soil and other materials for the purpose of depletion or detection using this approach.

Another embodiment of the invention is directed to methods for treating a disorder by the controlled release of a therapeutic agent at a selected site. Conjugates are formed by binding a bioreactive agent to a therapeutic agent with a bond that is selectively cleavable with electromagnetic radiation, wherein the bioreactive agent is comprised of a protein reactive group bonded to a photoreactive group. Conjugates are administered to a patient having the disorder and the selected site is subjected to a measured amount of electromagnetic radiation for the controlled release of the therapeutic agent to treat the disorder. Disorders which can be detected include infections, such as bacterial infections, viral infections and parasitic infections, neoplasias such as a tumor, and genetic disorders such as an overproduction or deficiency of an enzyme or other genetic product.

The therapeutic agents may be toxins, immune system modulators, hematopoietic agents, proteins, nucleic acids, substrate analogs, transcription and translation factors, antigens and combinations thereof. Protein reactive groups may be antibodies such as a monoclonal or polyclonal antibody or antibody fragment.

Another embodiment of the invention is directed to diagnostic kits for detecting or screening for diseases and disorders in patients. Kits contain a conjugate comprised of a bioreactive agent covalently bonded to a diagnostic agent having an affinity for an indicator of said disorder in a biological sample obtained from the patient. The indicator may be a presence or absence or an increased or decreased amount or level of a characteristic marker of the disorder such as an antigen or antibody, a cytokine, a specific cell type (e.g., B cells; cytotoxic, suppressor or helper T cells; macrophages; stem cells), a particular enzyme, nucleic acid or protein. Disorders which can be detected include infections, neoplasias and genetic disorders. Infections which can be detected include bacterial infections, viral infections and parasitic infections. Neoplasias which can be detected include tumors. Genetic disorders which can be detected include an overproduction or deficiency of an enzyme. Biological samples which can be added to the sample include samples of peripheral blood, blood plasma, serum, cerebrospinal fluid, lymph, urine, stool ophthalmic fluids, organs and bodily tissues. Such kits may also be used to detect or screen for the presence of fetal or stem cells in a biological sample which can be isolated and cultured or further analyzed.

Kits may also be used to detect the presence of multiple nucleic acids and/or proteins on, for example, an electroblot using a series of secondary probes linked to an affinity group. After each probe is introduced, the affinity group could be cleaved allowing the enzymatic assay complex to be removed thus providing for a new secondary probe to be introduced. Such an approach would be extremely useful as the basis of medical diagnostic assays, where multiple antigens or nucleic acid sequences needed to be probed rapidly and automatically.

The kit may also be a nucleic acid mutagenesis kit for use in molecular biological applications such as introducing or correcting mutations in DNA or RNA. The nucleic acid may be an oligonucleotide for use in PCR or cassette-type applications. Such oligonucleotides may be single-stranded or double-stranded and preferably contain one or more restriction enzyme recognition sequences internally and ligatable 5' and 3' ends which also contain part of a restriction enzyme recognition site. Alternatively, one or more ends may be blocked to facilitate directed coupling.

9. Quantitative Proteome Analysis

In one embodiment, the present invention contemplates that the present invention is used for quantitative proteome analysis. One exemplary embodiment of a method of quantitative proteome analysis comprises the following steps:

1) Reduction. Disulfide bonds of proteins in the sample and reference mixtures are reduced to free SH groups. Although any reducing agent may be used, the preferred reducing agent is tricarboethoxyphosphine (TCEP) which is used under standard conditions. Alternative reducing agents include tri-n-butylphosphine, mercaptoethylamine and dithiothreitol. If required, this reaction can be performed in the presence of solubilizing agents including high concentrations of urea and detergents to maintain protein solubility. The reference and sample protein mixtures to be compared are processed separately, applying identical reaction conditions;

2) Derivatization of SH groups with an affinity tag. Free SH groups are derivatized with the PC-Biotin-lysine-maleimide biotinylating reagent the synthesis of which is described below. The reagent is prepared in different isotopically labeled forms by substitution of linker atoms with stable isotopes and each sample is derivatized with a different isotopically labeled form of the reagent. Derivatization of SH groups is preferably performed under slightly basic conditions (pH 8.5) for 90 min at room temperature (RT). For the quantitative, comparative analysis of two samples, one sample each (termed reference sample and sample) are derivatized with the isotopically light and the isotopically heavy form of the reagent, respectively. For the comparative analysis of several samples one sample is designated a reference to which the other samples are related to. Typically, the reference sample is labeled with the isotopically heavy reagent and the experimental samples are labeled with the isotopically light form of the reagent, although this choice of reagents is arbitrary. These reactions are also compatible with the presence of high concentrations of solubilizing agents;

3) Combination of labeled samples. After completion of the affinity tagging reaction defined aliquots of the samples labeled with the isotopically different reagents (e.g., heavy and light reagents) are combined and all the subsequent steps are performed on the pooled samples. Combination of the differentially labeled samples at this early stage of the procedure eliminates variability due to subsequent reactions and manipulations. Preferably equal amounts of each sample are combined;

4) Removal of excess affinity tagged reagent. Excess reagent is removed for example by dialysis. Alternatively, the excess of the reagent can be removed by ion exchange chromatography after protein digestion step. Alternatively, the reagent is adsorbed, for example, by adding an excess of SH-containing beads to the reaction mixture after protein SH groups are completely derivatized. Beads are added to the solution to achieve about a 5-fold molar excess of SH groups over the reagent added and incubated for 30 min at RT. After the reaction the beads are be removed by centrifugation;

5) Protein digestion. The proteins in the sample mixture are digested, typically with trypsin. Alternative proteases are also compatible with the procedure as in fact are chemical fragmentation procedures (for example, CNBr cleavage). In cases in which the preceding steps were performed in the presence of high concentrations of denaturing solubilizing agents the sample mixture is diluted until the denaturant concentration is compatible with the activity of the proteases used. This step may be omitted in the analysis of small proteins;

6) Affinity isolation of the affinity tagged peptides by interaction with a capture reagent. After digestion the pH of the peptide samples is lowered to 6.5 and the biotinylated peptides are immobilized on beads coated with avidin or streptavidin (Pierce, Rockford, Ill.). The beads are extensively washed. The last washing solvent includes 10% methanol to remove residual SDS. PC-ICAT modified peptides are eluted from avidin-agarose, by resuspending in ammonium acetate buffer and irradiating with near UV light for 10–15 minutes. Alternatively, the PC-ICAT modified peptides are captured on monomeric avidin agarose support and eluted with 0.2% formic acid (pH=2). After chemical elution, the PC-Biotin portion is removed by irradiation with near UV light for 10–15 minutes and analyzed.

7) Analysis of the isolated, derivatized peptides by mLC-MS or CE-MS/MS with data dependent fragmentation. Methods and instrument control protocols well-known in the art and described, for example, in Ducret, et al., 1998; Figeys and Aebersold, 1998; Figeys, et al., 1996; or Haynes, et al., 1998 are used. Alternatively, reverse phase LC separation, fraction collection and analysis by MALDI-MS can be used.

In this last step, both the quantity and sequence identity of the proteins from which the tagged peptides originated can be determined by automated multistage MS. This is achieved by the operation of the mass spectrometer in a dual mode in which it alternates in successive scans between measuring the relative quantities of peptides eluting from the capillary column and recording the sequence information of selected peptides. Peptides are quantified by measuring in the MS mode the relative signal intensities for pairs of peptide ions of identical sequence that are tagged with the isotopically light or heavy forms of the reagent, respectively, and which therefore differ in mass by the mass differential encoded within the affinity tagged reagent. Peptide sequence information is automatically generated by selecting peptide ions of a particular mass-to-charge (m/z) ratio for collision-induced dissociation (CID) in the mass spectrometer operating in the MS/MS mode. (Link, A. J., et al., 1997; Gygi, S. P., et al. 1999). The resulting CID spectra are then automatically correlated with sequence databases to identify the protein from which the sequenced peptide originated. Combination of the results generated by MS and MS/MS analyses of affinity tagged and differentially labeled peptide samples therefore determines the relative quantities as well as the sequence identities of the components of protein mixtures in a single, automated operation.

This method can also be practiced using other affinity tags and other protein reactive groups, including amino reactive groups, carboxyl reactive groups, or groups that react with homoserine lactones.

The approach employed herein for quantitative proteome analysis is based on two principles. First, a short sequence of contiguous amino acids from a protein (about, for example, 5–25 residues) contains sufficient information to uniquely identify that protein. Protein identification by MS/MS is accomplished by correlating the sequence information contained in the CID (collision-induced dissociation) mass spectrum with sequence databases, using sophisticated computer searching algorithms (Eng, J., et al., 1994; Mann, M., et al., 1994; Qin, J., et al., 1997; Clauser, K. R., et al., 1995). Second, pairs of identical peptides tagged with the light and heavy affinity tagged reagents, respectively (or in analysis of more than two samples, sets of identical tagged peptides in which each set member is differentially isotopically labeled), are chemically identical and therefore serve as mutual internal standards for accurate quantitation. The MS measurement readily differentiates between peptides originating from different samples, representing for example different cell states, because of the difference between isotopically distinct reagents attached to the peptides. The ratios between the intensities of the differing weight components of these pairs or sets of peaks provide an accurate measure of the relative abundance of the peptides (and hence the proteins) in the original cell pools because the MS intensity response to a given peptide is independent of the isotopic composition of the reagents (De Leenheer, A. P., et al.,1992). The use of isotopically labeled internal standards is standard practice in quantitative mass spectrometry and has been exploited to great advantage in, for example, the precise quantitation of drugs and metabolites in bodily fluids (De Leenheer, A. P., et al., 1992).

In another embodiment of the method utilizing compounds of the present invention, single cysteine containing model peptides, gp120 analog and SV40 analog, were modified with light and heavy PC-ICAT reagent and then mixed at various ratios. The mixtures were captured on neutravidin-agarose support, beads were washed extensively and the tagged peptide mixture released by exposing bead suspension to near UV irradiation for 10–15 minutes. The supernatants were analyzed by MALDI-MS (FIGS. 21–22) and peaks resulting from the light and heavy PC-ICAT reagent modification, separated by ~8 Da integrated (FIG. 25).

In another embodiment of the method utilizing compounds of the present invention, two mixtures consisting of the same six proteins at known, but different, concentrations were prepared and analyzed. The protein mixtures were labeled and combined. The isolated, tagged peptides were quantified and sequenced in a single combined μLC-MS and μLC-MS/MS experiment on an ES1 ion trap mass spectrometer. All six proteins were unambiguously identified and accurately quantified. Multiple tagged peptides were encountered for each protein. The differences between the observed and expected quantities for the six proteins ranged between 2 and 12%.

Figure 26A:
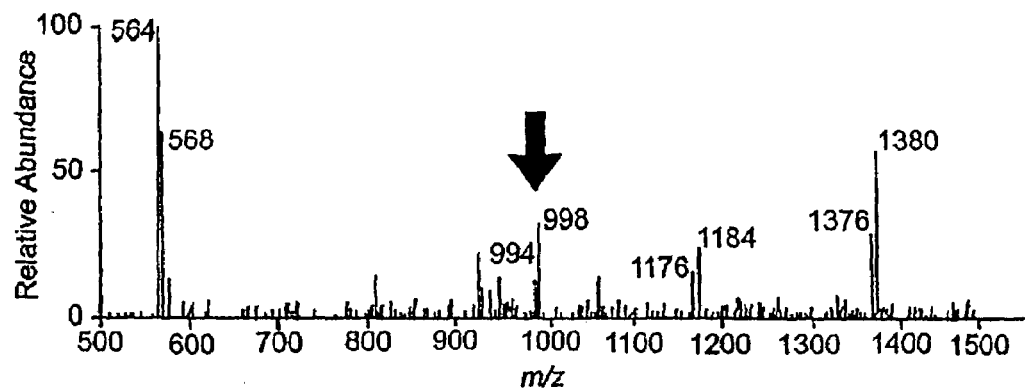
FIG. 26 shows (A) a single scan of the mass spectrometer operated in MS mode, (B) an expanded view of the mass spectrum around the ion pair with m/z ratios of 993.8 and 977.7, respectively and, (C) the reconstructed ion chromatograms for these two species.
Figure 26B:
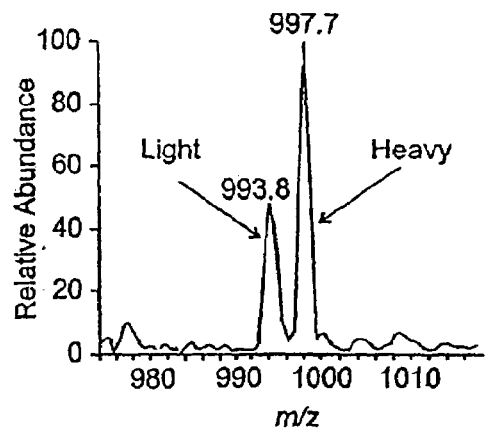
Figure 26C:
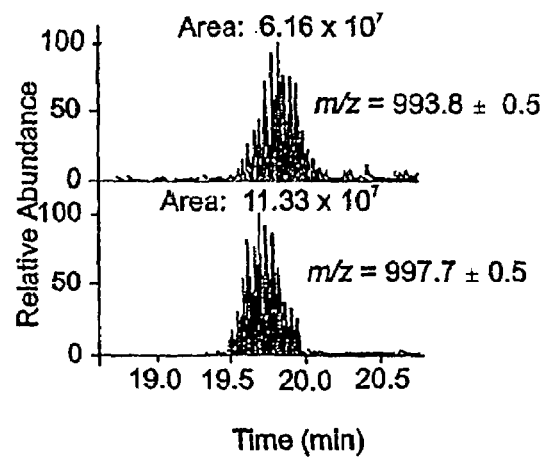
Figure 27A:
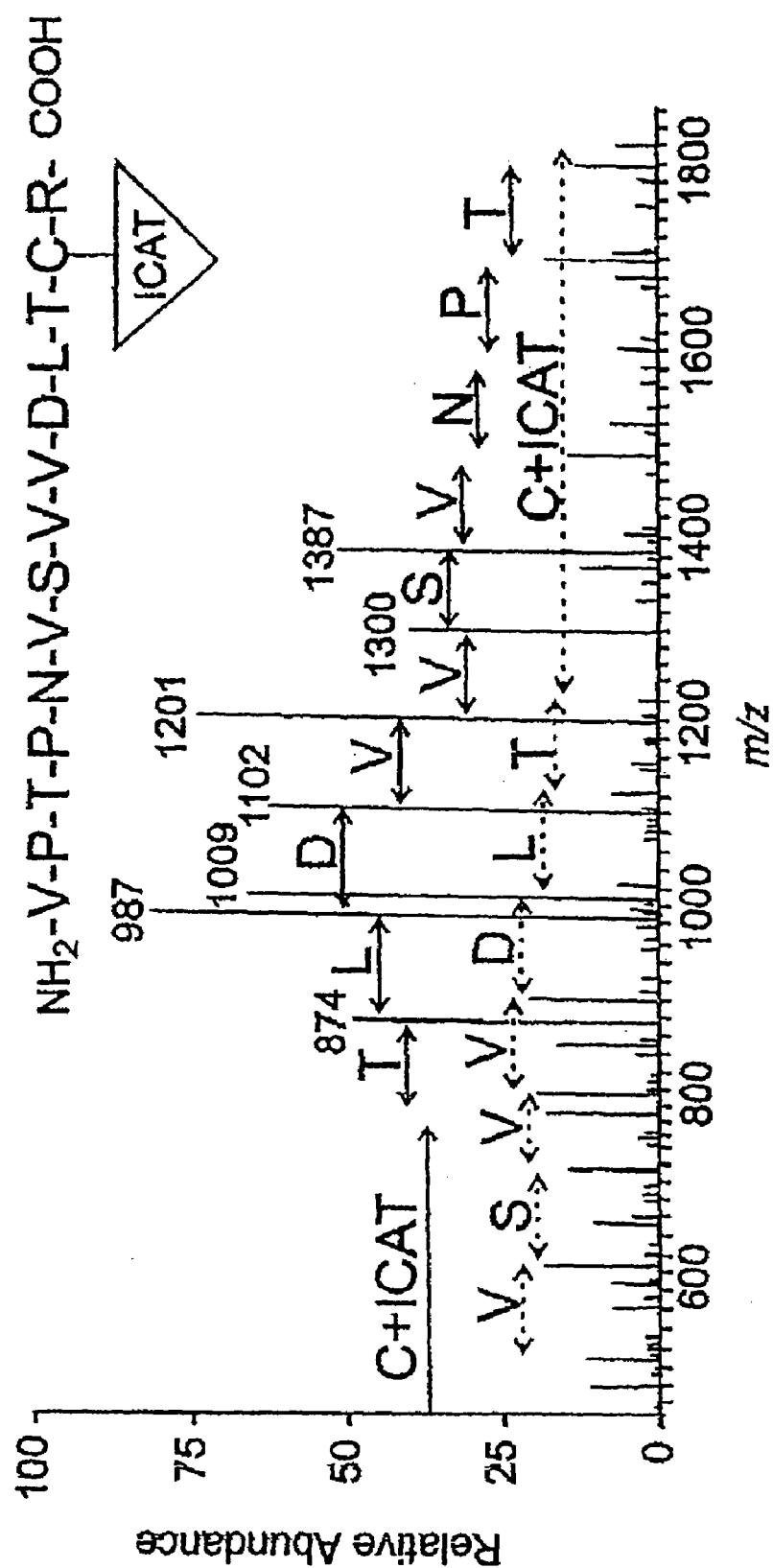
FIG. 27 shows (A) the CID spectrum recorded from the peptide ion with m/z=998 (marked with an arrow in FIG. 26A) and, (B) the database searching with this CID spectrum that identified the protein as glyceraldehyde-3-phosphate dehydrogenase.

The process is further illustrated for a single peptide pair in FIGS. 26A–C. A single scan of the mass spectrometer operated in MS mode is shown in FIG. 26A. Four pairs of peptide ions characterized by the mass differential encoded in the affinity tagged reagent are detected in this scan and indicated with their respective m/z values. The scan shown was acquired in 1.3 seconds. Over the course of the one-hour chromatographic elution gradient, more than 1200 such scans were automatically recorded. FIG. 26B shows an expanded view of the mass spectrum around the ion pair with m/z ratios of 993.8 and 977.7, respectively. Co-elution and a detected mass differential of four units potentially identifies the ions as a pair of doubly charged affinity tagged peptides of identical sequence (mass difference of eight and a charge state of two). FIG. 26C shows the reconstructed ion chromatograms for these two species. The relative quantities were determined by integrating the contour of the respective peaks. The ratio (light/heavy) was determined as 0.54. The peaks in the reconstructed ion chromatograms appear serrated because in every second scan the mass spectrometer switched between the MS and the MS/MS modes to collect sequence information (CID mass spectrum) of a selected peptide ion. These CID spectra were used to identify the protein from which the tagged peptides originated. FIG. 27A shows the CID spectrum recorded from the peptide ion with m/z=998 (marked with an arrow in FIG. 26A). Database searching with this CID spectrum identified the protein as glyceraldehyde-3-phosphate dehydrogenase (FIG. 27B) which was a member of the protein mixture.

Several beneficial features of the this method are apparent. First, at least two peptides were detected from each protein in the mixture. Therefore, both quantitation and protein identification can be redundant. Second, the identified peptides all contained at least one tagged cysteinyl residue. The presence of the relatively rare cysteinyl residue in a peptide adds an additional powerful constraint for database searching (Sechi, S,.et al., 1998). Third, tagging and selective enrichment of cysteine-containing peptides significantly reduced the complexity of the peptide mixture generated by the concurrent digestion of six proteins. For this protein mixture, the complexity was reduced from 293 potential tryptic peptides to 44 tryptic peptides containing at least one cysteinyl residue. Fourth, the peptide samples eluted from the avidin affinity column are directly compatible with analysis by μLC-MS/MS.

10. Quantitative Analysis of Protein Expression in Different Cell States

In another embodiment, the protein reactive affinity reagent strategy was applied to study differences in steady-state protein expression in the yeast, S. cerevisiae, in two non-glucose repressed states. Cells were harvested from yeast growing in log-phase utilizing either 2% galactose or 2% ethanol as the carbon source. One-hundred μg of soluble yeast protein from each cell state were labeled independently with the isotopically different affinity tagged reagents. The labeled samples were combined and subjected to analysis. One fiftieth (the equivalent of approximately 2 μg of protein from each cell state) of the sample was analyzed.

Glucose repression causes large numbers of proteins with metabolic functions significant to growth on other carbon sources to be minimally expressed (Ronne, H., 1995; Hodges, P. E., et al., 1999). Growth on galactose or ethanol with no glucose present results in the expression of glucose repressed genes. Each of these genes would have been minimally expressed in yeast grown on glucose. Genes specific to both growth on galactose (GALL, GALL 10) as well as growth on ethanol (ADH2, ACH1) were detected and quantitated.

The quantitative nature of the method is apparent in the ability to accurately measure small changes in relative protein levels. Evidence of the accuracy of the measurements can be seen by the excellent agreement found by examining ratios for proteins for which multiple peptides were quantified. For example, the five peptides found from PCK1 had a mean ratio ~95% confidence intervals of 1.57~0.15, and the percent error was ~10%. In addition, the observed changes fit the expected changes from the literature (Ronne, H., 1995; Hodges, P. E., et al., 1999). Finally, the observed changes are in agreement with the changes in staining intensity for these same proteins examined after two-dimensional gel electrophoresis.

The alcohol dehydrogenase family of isozymes in yeast facilitates growth on either hexose sugars (ADH1) and ethanol (ADH2). The gene ADH2 encodes an enzyme that is both glucose- and galactose-repressed and permits a yeast cell to grow entirely on ethanol by converting it into acetaldehyde which enters the TCA cycle. In the presence of sugar, ADH1 performs the reverse reaction converting acetaldehyde into ethanol. The regulation of these isozymes is key to carbon utilization in yeast (Ronne, H., 1995). The ability to accurately measure differences in gene expression across families of isozymes is sometimes difficult using cDNA array techniques because of cross hybridization (DeRisi, J. L., et al., 1997). The method succeeded in measuring gene expression for each isozyme even though ADH1 and ADH2 share 93% amino acid (88% nucleotide) sequence similarity. This was because the affinity tagged peptides from each isozyme differed by a single amino acid residue (valine to threonine) which shifted the retention time by more than 2 min and the mass by 2 daltons for the ADH2 peptides. ADH1 was expressed at approximately 2-fold high levels when galactose was the carbon source compared with ethanol. Ethanol-induction of ADH2 expression resulted in more than 200-fold increases compared with galactose-induction.

The results described above illustrate that the method of this invention provides quantitative analysis of protein mixtures and the identification of the protein components therein in a single, automated operation.

The method as applied using a sulfhydryl reactive reagent significantly reduces the complexity of the peptide mixtures because affinity tagged cysteine-containing peptides are selectively isolated. For example, a theoretical tryptic digest of the entire yeast proteome (6113 proteins) produces 344, 855 peptides, but only 30,619 of these peptides contain a cysteinyl residue. Thus, the complexity of the mixture is reduced, while protein quantitation and identification are still achieved. The chemical reaction in of the sulfhydryl reagent with protein can be performed in the presence of urea, sodium dodecyl sulfate (SDS), salts and other chemicals that do not contain a reactive thiol group. Therefore, proteins can be kept in solution with powerful stabilizing agents until they are enzymatically digested. The sensitivity of the μLC-MS/MS system is dependent of the sample quality. In particular, commonly used protein solubilizing agents are poorly compatible or incompatible with MS. Affinity purification of the tagged peptides completely eliminates contaminants incompatible with MS. The quantitation and identification of low abundance proteins by conventional methods requires large amounts (milligrams) of starting protein lysate and involves some type of enrichment for these low abundance proteins. Assays described above, start with about 100 pg (picogram) of protein and used no fractionation techniques. Of this, approximately 1/20 of the protein was analyzed in a single μLC-MS/MS experiment. This system has a limit of detection of 10–20 fmol (fentamol) per peptide (Gygi, S. P., et al., 1999). For this reason, in the assays described which employ μLC-MS/MS only abundant proteins are detected. However, the methods of this invention are compatible with any biochemical, immunological or cell biological fractionation methods that reduce the mixture complexity and enrich for proteins of low abundance while quantitation is maintained. This method can be redundant in both quantitation and identification if multiple cysteines are detected. There is a dynamic range associated with the ability of the method to quantitate differences in expression levels of affinity tagged peptides which is dependent on both the intensity of the peaks corresponding the peptide pair (or set) and the overall mixture complexity. In addition, this dynamic range will be different for each type of mass spectrometer used. The ion trap was employed in assays described herein because of its ability to collect impressive amounts of sequencing information (thousands of proteins can potentially be identified) in a data-dependent fashion even though it offers a more limited dynamic quantitation range. The dynamic range of the ion trap (based on signal-to-noise ratios) varied depending on the signal intensity of the peptide pair and complexity of the mixture, but differences of up to 100-fold were generally detectable and even larger differences could be determined for more abundant peptides. In addition, protein expression level changes of more than 100–200-fold still identify those proteins as major potential contributors to the phenotypic differences between the two original cell states. The method can be extended to include reactivity toward other functional groups. A small percentage of proteins (8% for S. cerevisiae) contain no cysteinyl residues and are therefore missed by analysis using reagents with sulfhydryl group specificity (i.e., thiol group specificity). Affinity tagged reagents with specificities toward functional groups other than sulfhydryl groups will also make cysteine-free proteins susceptible to analysis.

The methods of this invention can be applied to analysis of low abundance proteins and classes of proteins with particular physicochemical properties including poor solubility, large or small size and extreme p/values.

The prototypical application of the chemistry and method is the establishment of quantitative profiles of complex protein samples and ultimately total lysates of cells and tissues following the preferred method described above. In addition the reagents and methods of this invention have applications which go beyond the determination of protein expression profiles. Such applications include the following:

Application of amino-reactive or sulfhydryl-reactive, differentially isotopically labeled affinity tagged reagents for the quantitative analysis of proteins in immunoprecipitated complexes. In the preferred version of this technique protein complexes from cells representing different states (e.g., different states of activation, different disease states, different states of differentiation) are precipitated with a specific reagent, preferably an antibody. The proteins in the precipitated complex are then derivatized and analyzed as above.

Application of amino-reactive, differentially isotopically labeled affinity tagged reagents to determine the sites of induced protein phosphorylation. In a preferred version of this method purified proteins (e.g., immunoprecipitated from cells under different stimulatory conditions) are fragmented and derivatized as described above. Phosphopeptides are identified in the resulting peptide mixture by fragmentation in the ion source of the ESI-MS instrument and their relative abundances are determined by comparing the ion signal intensities of the experimental sample with the intensity of an included, isotopically labeled standard.

Amino-reactive, differentially isotopically labeled affinity tagged reagents are used to identify the N-terminal ion series in MS/MS spectra. In a preferred version of this application, the peptides to be analyzed are derivatized with a 50:50 mixture of an isotopically light and heavy reagent which is specific for amino groups. Fragmentation of the peptides by CID therefore produce two N-terminal ion series which differ in mass precisely by the mass differential of the reagent species used. This application dramatically reduces the difficulty in determining the amino acid sequence of the derivatized peptide.

11. Quantitative Analysis of Surface Proteins in Cells and Tissue

In another embodiment, the photocleavable reagents of this invention are used for the analysis of cell surface proteins. The cell exterior membrane and its associated proteins (cell surface proteins) participate in sensing external signals and responding to environmental cues. Changes in the abundance of cell surface proteins can reflect a specific cellular state or the ability of a cell to respond to its changing environment. Thus, the comprehensive, quantitative characterization of the protein components of the cell surface can identify marker proteins or constellations of marker proteins characteristic for a particular cellular state, or explain the molecular basis for cellular responses to external stimuli. Indeed, changes in expression of a number of cell surface receptors such as Her2/neu, erbB, IGFI receptor, and EGF receptor have been implicated in carcinogenesis and a current immunological therapeutic approach for breast cancer is based on the infusion of an antibody (Herceptin, Genentech, Palo Alto, Calif.) that specifically recognizes Her2/neu receptor.

Cell surface proteins are also experimentally accessible. Diagnostic assays for cell classification and preparative isolation of specific cells by methods such as cell sorting or panning are based on cell surface proteins. Thus, differential analysis of cell surface proteins between normal and diseased (e.g., cancer) cells can identify important diagnostic or therapeutic targets. While the importance of cell surface proteins for diagnosis and therapy of cancer has been recognized, membrane proteins have been difficult to analyze. Due to their generally poor solubility they tend to be under-represented in standard 2D gel electrophoresis patterns and attempts to adapt 2D electrophoresis conditions to the separation of membrane proteins have met limited success. The method of this invention can overcome the limitations inherent in the traditional techniques.

The analysis of membrane proteins is challenging because they generally are difficult to maintain in solution under conditions that are compatible with high sensitivity analytical instruments such as mass spectrometers. The application of the methods of the present invention to the analysis of membrane proteins is exemplified using human T cell lymphoma cell line Jurkat for membrane protein labeling and extraction and the well characterized human prostate epithelial cell line P69SV40T and two P69SV40T sublines which differ in IGF-1 receptor expression by factor of 10 to exemplify quantitative, differential analysis of membrane proteins.

Jurkat cells are an appropriate model system because the cells are easy to grow in large numbers and because the modulation of cell surface proteins in response to different stimuli and experimental conditions has been well characterized in T lymphocytes. Commercially available biotinylating reagents or more generally affinity tagging reagents are employed to derivatize lysine residues and the free N-termini. Water soluble biotinylating reagents such as Sulfo-NHS (hydroxy succinimide) biotin and analogs (Sulfosuccinimidyl-6-(biotinamido)-hexanoate; Pierce, Rockford, Ill.) which have been used extensively for labeling cell surface proteins can be employed. The reaction of NHS esters with primary amines is best at neutral pH values and above and is compatible with the presence of organic solvent such as DMSO (dimethylsufoxide) or DMF (dimethylfluoride). Biotinylation of cell surface proteins from the Jurkat cells is carried out in PBS buffer at pH 7.2. Cells ($1 \times 10^7$) are washed with PBS buffer to remove contaminating serum and other proteins from the culture medium. The cells are resuspended at $25 \times 10^6$ cell/ml and reacted with 0.5 mg/ml of Sulfo-NHS-Biotin (Pierce, Rockford, Ill.) for 30 min at RT. The labeled cells are washed twice with cold PBS to remove unreacted biotinylating reagent. Biotinylated cells are solubilized at $5 \times 10^7$ cells/ml in lysis buffer containing 1% Triton X-114. Triton X-114 has the property of phase-partitioning into detergent phase and aqueous phase at 30° C. Following the phase partitioning, detergent phase is removed from the aqueous phase by centrifugation at 300×g. Phase partitioning has previously been successfully used to enrich cell membrane. Also, this technique was found to enrich membrane proteins from Jurkat cell lysates. Triton phase is diluted 1:5 (v/v) using 50 mM ammonium bicarbonate buffer, pH 8.5, and high-purity, modified porcine-trypsin is added to digest the proteins at a concentration of 12.5 mg/ml for overnight at 37° C. Trypsin is neutralized by the addition of a cocktail of serine protease inhibitors and tryptic peptides are isolated by the avidin affinity chromatography techniques. Eluted peptides are separated, e.g., by µLC methods and identified by searching peptide sequence databases, using for example, the Sequest program.

The human prostate epithelial cell line P69SV40T which was immortalized with SV 40 T antigen has been well characterized. This cell line is immortal but not tumorigenic and expresses type 1 insulin like growth factor receptor (IGF-1 R) at $2 \times 10^4$ receptors per cell. A subline, called M12, was derived from P69SV40T by sequential passage in male athymic nude mice. This cell line is highly tumorigenic and metastatic and expresses $1.1 \times 10^3$ IGF-1 R per cell. The relative difference in the abundance of IGF-1R in the cell lines P69SV40T and M12 can be quantitatively determined using methods of this invention adapted for application to membrane proteins. Since the number of IGF-1R for these cell lines has already been determined, this well characterized system can provide a reference to validate the efficiency of the quantitative methods of this invention.

P69SV40T cells ($1 \times 10^7$) are biotinylated with an isotopically heavy biotin tagged amino reactive reagent and the M12 cells ($1 \times 10^7$) are biotinylated with a corresponding isotopically light amine reactive biotin tagged amino reactive reagent. IGF-1 R is then immunoprecipitated from the combined lysate of both cell lines using an antibody against human IGF-1 R and the total mass of immunoprecipitated proteins is digested with trypsin. Trypsin is then neutralized, e.g., by the addition of inhibitors and tagged peptides are purified by biotin-avidin affinity chromatography. The eluted peptides are analyzed by LC-MS and LC-MSN$^N$ for peptide quantitation and identification, respectively, as has been described above. Quantitation in this experiment is facilitated by the option to use selective ion monitoring in the MS. In this mode only the masses of tagged peptide ions expected to derive from IGF-1R need be monitored.

The described technique can be applied to compare the differences in relative abundance of cell surface proteins between parental prostate cell line (P69SV40T) and M12 cells to detect and identify those cell surface proteins whose expression level is different in the two cell lines and which may be characteristic of the different cell states. Using the methods described herein global, relative quantitation of the cell surface proteins in any two or more cell lines can be analyzed to detect and identify those cell surface proteins characteristic of the different cell states. Results can be independent confirmed using procedure such as 1D or 2D gels, if applicable, or quantitative western blotting to confirm quantitation results.

It is expected that the experimental variability of quantitation of cell surface proteins will be considerably better than the accuracy of quantitation achieved by currently available cDNA array technology. In addition to relative protein quantity and identity, the method can also be used to reveal the orientation of the protein in the membrane, based on the presumption that intact, alive cells will exclude the biotinylating reagent.

Alternative methods can be applied to enhance the selectivity for tagged peptides derived from cell surface proteins. For example, tagged cell surface proteins can be trypsinized directly on the intact cells to generate tagged peptides, purified and analyzed as discussed. In addition, traditional cell membrane preparations may be used as an initial step to enrich cell surface proteins. These methods can include gentle cell lysis with a Dounce homogenizer and series of density gradient centrifugations to isolate membrane proteins prior to proteolysis. This method can provide highly enriched preparations of cell surface proteins. Affinity tagged proteins may also be isolated by affinity chromatography prior to proteolysis as well as after proteolysis. This chromatography can be performed in the presence of surfactants such as TX-100, NP-40 or Tween-20 to maintain protein solubility. The sequential application of affinity chromatography steps (one for the intact protein and one for the tagged peptide fragments) provides a high degree of selectivity. These alternative methods are easily scalable for the detection of low abundance membrane proteins and the relative quantity of tagged peptides tagged is maintained through the selective enrichment steps.

Figure 11:
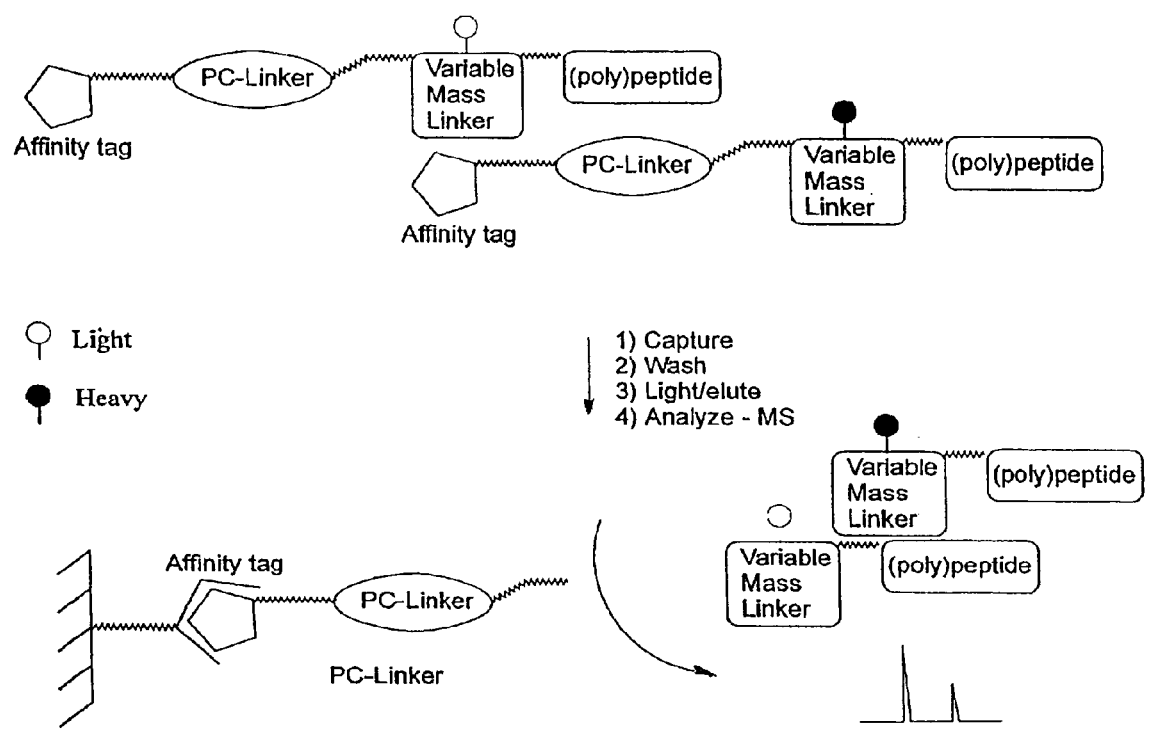
FIG. 11 shows another diagram of protein quantitation procedure using Photocleavable Bioreactive Agents with Variable Mass Linkers.

In the application of the methods of this invention to cell surface proteins, once the tagged proteins are fragmented, the tagged peptides behave no differently from the peptides generated from more soluble samples. FIGS. 10 and 11 show diagrammatically the isolation, quantification and characterization of selected samples utilizing the compounds of the present invention. Specifically, FIGS. 10 and 11 show a diagram of protein quantitation procedure using Photocleavable Bioreactive Agents with Variable Mass Linkers. A protein mixture obtained from two different cellular states is labeled with light and heavy versions of Photocleavable Bioreactive Agent. Then the mixtures were combined, proteins digested using, for example, trypsin and captured on an affinity support, for example, streptavidin. In the next step, the unbound proteolytic fragments were removed by washing the affinity support and bound fragments were photoreleased by irradiation. After the photocleavage, part of the reagent containing light or heavy variable mass linker remains on the peptide and serves as a mass tag. The mixture of photoreleased peptides was then analyzed using mass spectrometry and the relative abundance of peptides labeled with light and heavy reagent determined.

12. Notes on Immobilized Photocleavable ICAT Synthesis

Zhou, et al., (Nature Biotech. 19:512 (2002), described the synthesis of the immobilized photocleavable ICAT reagent based on the use of 4-[4-(Fmoc-amino)-2-methoxy-5-nitrophenoxy)butanoic acid. The use of the 2-nitrobenzyl group with electron-donating substituents is known to decrease the rate of the photocleavage reaction (Hasan, A., et al., Tetrahedron 53:4247–4264, 1997). This necessitated very long irradiation times to achieve the photocleavage (1 hr with 100 W electrical power light source). The linkers used in the present invention are known to exhibit very fast and efficient photocleavage (Milbum, T., et al., Biochemistry, 28(1):49–55, 1989; Walker, et al., J. Am. Chem. Soc., 110:7170–7177, 1988) with exposure times as short as 5 minutes and the source with electrical power of only 30 W giving nearly quantitative photocleavage (Olejnik, J., et. al., Nucleic Acids Res. 24(2):361–366, 1996). In addition, the linker design described by Zhou, et al., (Nature Biotech. 19:512, 2002) causes the peptide fragment to be released as primary amide. The linker of present invention generates primary amines, which are known to be photocleaved easier and, in addition, act as a "charge tag" for mass spectrometry applications.

Photocleavable linkers of other ICAT systems are limited to photocleavable linkers that contain a 1-(2-nitrophenyl)-ethyl group (see, for example, US 2002/0076739 A1 to Aebersold, et al.). Embodiments of the present invention do not comprise a linker that contains a 1-(2-nitrophenyl)-ethyl group. This is a significant improvement over the prior art. Photocleavable groups or photocleavable linkers comprising a 1-(2-nitrophenyl)-ethyl group are less responsive to light and, therefore, require higher levels of electromagnetic radiation than the photoreactive groups of the present invention. A preferred example of the linker molecule of the present invention is given in FIG. 14A, compound 4. Other examples are given in FIGS. 14B (compound 4), 14C (compound 4) and 14D (compound 4). The linker molecules of the present invention have advantages over the prior art that include: 1) they are less expensive to produce, 2) they are easier to manufacture and use (e.g., they are more soluble, see below), 3) they are less hazardous to use and 4) they give a clean spectrum as compared to the prior art compounds since sodium ions (Na+) are removed. In the present invention, after the high salt wash (used to elute and dislodge biotin from monomeric avidin), ammonium acetate is used to remove sodium ions. This step results in a cleaner mass spectrometry spectra. Additionally, the linker in the compounds of the present invention are ether-based, not peptide bonds. The peptide bonds of the prior art are not very water soluble. The ether-based bonds of the present invention are water soluble. The methods of the present invention are less hazardous to use because TFA is not used in the cleavage step. In the present invention, PC-ICAT is photocleaved by, for example, near U.V. light.

13. Reactivity of Thiol Groups

Reagents with reactivities towards thiols (cysteines) and also amino groups (N-terminal alpha amino group and epsilon amino groups on the lysine residues are contemplated.

In proteins, thiol groups (also called mercaptans or sulfhydryls) are present in cysteine residues. Thiols can also be generated by selectively reducing cysteine disulfides with reagents such as dithiothreitol (Gorman J J, Corino G L, Mitchell S J. Eur J Biochem 168, 169–179 (1987) or β-mercaptoethanol, each of which must then be removed by dialysis or gel filtration before reaction with the thiol-reactive probe (Jocelyn P C. Methods Enzymol 143, 246–256 (1987). Unfortunately, removal of DTT or b-mercaptoethanol is sometimes accompanied by air oxidation of the thiols back to the disulfides. Reformation of the disulfide bond can be avoided by using the reducing agent tris-(2-carboxyethyl)phosphine (Getz E B, Xiao M, Chakrabarty T, Cooke R, Selvin P R. Anal Biochem 273, 73–80 (1999), which usually does not need to be removed prior to thiol modification because it does not contain thiols. TCEP is generally impermeable to cell membranes and to the hydrophobic protein core, permitting its use for the selective reduction of disulfides that have aqueous exposure. The pH-insensitive and less polar phosphine derivative tris-(2-cyanoethyl)phosphine may yield greater reactivity with buried disulfides. Several reagents have also been developed for introducing thiols into proteins, nucleic acids and lipids, permitting the use of any of the fluorescent or chromophoric thiol-reactive reagents for their covalent modification. The thiol-reactive functional groups are primarily alkylating reagents, including iodoacetamides, maleimides, benzylic halides and bromomethylketones. Arylating Reagents such as NBD halides react with thiols or amines by a similar substitution of the aromatic halide. Reaction of any of these functional groups with thiols usually proceeds rapidly at or below room temperature in the physiological pH range (pH 6.5–8.0) to yield chemically stable thio ethers.

14. Iodoacetamides

A variety of PC-ICAT reagents that utilize "light" and "heavy" versions of lysine amino acid as a building block can be created. Some preferred embodiments include PC-ICAT reagents with reactivity towards free sulfhydryl groups of cysteines. These reagents comprise a maleimide reactive group (FIG. 14E, PC-ICAT#1) or an iodoacetamide reactive group (FIG. 14E, PC-ICAT#2). In addition, in some cases, for example, if a protein does not contain cysteine residues or if a differential filter needs to be applied then PC-ICAT reagent reactive towards free amino groups present in proteins are desirable. The structure of one such reagent is shown in FIG. 14E (PC-ICAT#3). Details of PC-ICAT idoacetamides, maleimides and amines follow.

Iodoacetamides readily react with all thiols, including those found in peptides, proteins and thiolated polynucleotides, to form thioethers; they are somewhat more reactive than bromoacetamides. However, when a proteins cysteine residues are blocked or absent, iodoacetamides can sometimes react with methionine residues (Musci G, Berliner L J. Biochemistry 25, 4887–4891, 1986; Chung D G, Lewis P N. Biochemistry 25, 5036–5042, 1986). They may also react with histidine (Jullien M, Garel J R. Biochemistry 20, 7021–7026, 1981) or tyrosine, but generally only if free thiols are absent. Although iodoacetamides can react with the free base form of amines, most aliphatic amines, except the a-amino group at a proteins N-terminus, are protonated and thus relatively unreactive below pH 8. In addition, iodoacetamides react with thiolated oligonucleotide primers, as well as with thiophosphates and thiouridine residues present in certain nucleic acids (Ansorge W, et al., *Nucleic Acids Res* 16, 2203–2206, 1988) but usually not with the common nucleotides.

Iodoacetamides are intrinsically unstable in light, especially in solution; reactions should therefore be carried out under subdued light. Adding cysteine, glutathione or mercaptosuccinic acid to the reaction mixture will quench the reaction of thiol-reactive probes, forming highly water-soluble adducts that are easily removed by dialysis or gel filtration. Although the thio ether bond formed when an iodoacetamide reacts with a protein thiol is very stable, during amino acid hydrolysis the bioconjugate loses its fluorophore to yield S-carboxymethylcysteine. An example is shown in FIG. 14E, #2.

15. Maleimides

Maleimides are excellent reagents for thiol-selective modification, quantitation and analysis. The reaction involves addition of the thiol across the double bond of the maleimide to yield a thioether. The applications of these fluorescent and chromophoric analogs of N-ethylmaleimide (NEM) strongly overlap those of iodoacetamides, although maleimides apparently do not react with methionine, histidine or tyrosine. Reaction of maleimides with amines usually requires a higher pH than reaction of maleimides with thiols. Hydrolysis of maleimides to a mixture of isomeric nonreactive maleamic acids can compete significantly with thiol modification, particularly above pH 8. An example is shown in FIG. 14E, #1.

16. Other Thiol-Reactive Reagents

A variety of other thiol-reactive probes is known. These include alkyl halides and arylating agents (NBD chloride, ABD fluoride) as well as symmetric disulfides which undergo a thiol-disulfide interchange reaction to yield a new asymmetric disulfide a reaction that is freely reversible and is thiol-specific. The covalent adducts from these thiol-reactive probes are, in general, more resistant to hydrolysis than those from iodoacetamides or maleimides, which are somewhat sensitive to hydrolysis at the amide linkage connecting the fluorophore to its reactive group A variety of bifunctional crosslinkers is available and can be used to prepare reagents and conjugates of the present invention. In particular the bifunctional crosslinkers reactive towards amino group on one end and having thiol-reactive group on the other end of the linker are useful. Table 4 below summarizes some of the linkers available from Pierce Chemical Co.

TABLE 4

Amines to Sulfhydryls Crosslinkers

| Acronym | Prod. Number | Chemical Name | Cleavable By | Water Soluble | Membrane Permeable |
|---|---|---|---|---|---|
| SMPT | 21558 | 4-Succinimidyloxycarbonyl-α-methyl-α-(2-pyridyldithio)toluene | Thiols | No | Yes |
| Sulfo-LC-SMPT | 21568 | Sulfosuccinimidyl 6-[α-methyl-α-(2-pyridyldithio) toluamido]hexanoate | Thiols | Yes | No |
| Sulfo-KMUS | 21111 | (N-[κ-Maleimidoundecanoyloxy])-sulfosuccinimide ester) | non | Yes | No |
| LC-SMCC | 22362 | Succiminidyl-4-(N-maleimidomethyl)cyclohexane-1-carboxy-(6-amidocaproate) | non | No | Yes |
| KMUA | 22211 | N-(κ-Maleimidoundecanoic acid) | non | No | nd |
| Sulfo-LC-SPDP | 21650 | Sulfosuccinimidyl 6-[3'(2-pyridyldithio)-propionamido] hexanoate | Thiols | Yes | No |
| LC-SPDP | 21651 | Succinimidyl 6-[3'-(2-pyridyldithio)-propionamido] hexanoate | Thiols | No | Yes |
| SMPB | 22416 | Succinimidyl 4-(P-Maleimidophenyl) Butyrate | non | No | Yes |
| Sulfo-SMPB | 22317 | Sulfosuccinimidyl 4-(P-Maleimidophenyl) Butyrate | non | Yes | No |
| SMPH | 22363 | SMPH, Succinimidyl-6[(β-maleimidopropionamido) hexanoate] | non | No | nd |
| Sulfo-SMCC | 22322 | Sulfosuccinimidyl 4-(N-maleimidomethyl)cyclohexane-1-carboxylate | non | Yes | No |
| SMCC | 22360 | Succinimidyl 4-(N-maleimidomethyl)cyclohexane-1-carboxylate | non | No | Yes |
| SIAB | 22329 | N-Succinimidyl(4-iodoacetyl)aminobenzoate | non | No | Yes |
| Sulfo-SIAB | 22327 | Sulfosuccinimidyl(4-iodoacetyl)aminobenzoate | non | Yes | No |
| Sulfo-GMBS | 22324 | N-[γ-Maleimidobutyryloxy]sulfosuccinimide ester | non | Yes | No |
| GMBS | 22309 | N-[γ-Maleimidobutyryloxy]-succinimide ester | non | No | Yes |
| MBS | 22311 | m-Maleimidobenzoyl-N-hydroxysuccinimide ester | non | No | Yes |
| Sulfo-MBS | 22312 | m-Maleimidobenzoyl-N-hydroxysulfosuccinimide ester | non | Yes | No |
| Sulfo- | 22307 | N-(ε-Maleimidocaproyloxy) | non | Yes | No |

TABLE 4-continued

Amines to Sulfhydryls Crosslinkers

| Acronym | Prod. Number | Chemical Name | Cleavable By | Water Soluble | Membrane Permeable |
|---|---|---|---|---|---|
| EMCS | | Sulfosuccinimide Ester | | | |
| EMCA | 22306 | N-e-Maleimidocaproic acid | non | Yes | No |
| EMCS | 22308 | N(ε-Maleimidscaproyloxy)Succinimide Ester | non | No | Yes |
| SVSB | 22358 | N-Succinimidyl-(4-Vinylsulfonyl)Benzoate | non | No | Yes |
| BMPS | 22298 | (N-[β-Maleimidopropyloxy]-succinimide ester) | non | No | nd |
| SPDP | 21857 | N-Succinimidyl 3-(2-pyridyldithio) propionate | Thiols | No | Yes |
| SBAP | 22339 | Succinimidyl 3-(Bromoacetamido)Propionate | non | No | Yes |
| BMPA | 22296 | N-Beta-Maleimidopropionic Acid | non | Yes | No |
| AMAS | 22295 | (N-[α-Maleimidoacetoxy]succinimide ester) | non | No | nd |
| SATP | 26100 | (N-Succinimidyl S-acetylthiopropionate) | non | No | Yes |
| SIA | 22349 | (N-Succinimidyl iodoacetate) | non | No | nd | nd = not determined

17. Reactivity of Amino Groups

Another embodiment of the present invention are reagents designed to react with amines. These can be found in the proteins at either the N-terminus (alpha-amino group) or as epsilon-amino groups on lysine residues.

The amine-reactive probes are mostly acylating reagents that form carboxamides, sulfonamides, ureas or thioureas upon reaction with amines. The kinetics of the reaction depends on the reactivity and concentration of both the acylating reagent and the amine. Of course, buffers that contain free amines such as Tris and glycine must be avoided when using any amine-reactive probe. Ammonium sulfate that has been used for protein precipitation must also be removed before performing dye conjugations. In addition, high concentrations of nucleophilic thiols should be avoided because they may react with the reagent to form an unstable intermediate that could consume the dye. The most significant factors affecting an amines reactivity are its class and its basicity. Virtually all proteins have lysine residues, and most have a free amine at the N-terminus. Aliphatic amines such as lysines epsilon amino group are moderately basic and reactive with most acylating reagents. However, the concentration of the free base form of aliphatic amines below pH 8 is very low; thus, the kinetics of acylation reactions of amines by isothiocyanates, succinimidyl esters and other reagents are strongly pH dependent. A pH of 8.5 to 9.5 is usually optimal for modifying lysine residues. In contrast, the α-amino group at a proteins N-terminus usually has a pKa of ~7, so it can sometimes be selectively modified by reaction at near neutral pH. Furthermore, although amine acylation should usually be carried out above pH 8.5, the acylation reagents tend to degrade in the presence of water, with the rate increasing as the pH increases. Protein modification by succinimidyl esters can typically be done at pH 8.5, whereas isothiocyanates usually require a pH >9 for optimal conjugations; this high pH may be a factor when working with base-sensitive proteins.

In aqueous solution, acylating reagents are virtually unreactive with the amide group of peptide bonds and the side chain amides of glutamine and asparagine residues, the guanidinium group of arginine, the imidazolium group of histidine and the nonbasic amines, such as adenosine or guanosine, found in nucleotides and nucleic acids. Isothiocyanates form thioureas upon reaction with amines. Although the thiourea product is reasonably stable, it has been reported that antibody conjugates prepared from fluorescent isothiocyanates deteriorate over time.

18. Succinimidyl Esters and Carboxylic Acids

Succinimidyl Esters are excellent reagents for amine modification because the amide bonds they form are as stable as peptide bonds. These reagents are generally stable during storage if well desiccated, and show good reactivity with aliphatic amines and very low reactivity with aromatic amines, alcohols, phenols (including tyrosine) and histidine. Succinimidyl esters will also react with thiols in organic solvents to form thioesters. If formed in a protein, a thioester may transfer the acyl group to a nearby amine. Succinimidyl ester hydrolysis can compete with conjugation, but this side reaction is usually slow below pH 9.

Some succinimidyl esters may not be compatible with a specific application because they can be quite insoluble in aqueous solution. To overcome this limitation, carboxylic acid derivatives of some of its fluorophores are available (Molecular Probes, Eugene, Oreg.), which can be converted into Sulfosuccinimidyl Esters or STP Esters. These sulfonated reagents have higher water solubility than simple succinimidyl esters and sometimes eliminate the need for organic solvents in the conjugation reaction. However, they are also more polar, which makes them less likely to react with buried amines in proteins or to penetrate cell membranes. Because of their combination of reactivity and polarity, sulfosuccinimidyl esters are not easily purified by chromatographic means. Sulfosuccinimidyl esters can generally be prepared in situ simply by dissolving the carboxylic acid dye in an amine-free buffer that contains N-hydroxysulfosuccinimide and 1-ethyl-3-(3-dimethylaminopropyl) carbodiimide (EDAC). Addition of NHSS to the buffer has been shown to enhance the yield of carbodiimide-mediated conjugations (Staros J V, Wright R W, Swingle D M., Anal Biochem 156, 220–222, 1986). STP esters are prepared in the same way from 4-sulfo-2,3,5,6-tetrafluorophenol (Gee K R, Archer E A, Kang H C., Tetrahedron Lett 40, 1471, 1999), and are more readily purified by chromatography than their sulfosuccinimidyl ester counterparts. The carboxylic acids may also be useful for preparing acid chlorides and anhydrides, which, unlike succinimidyl esters, can be used to modify aromatic amines and alcohols.

18. Sulfonyl Chlorides

Sulfonyl Chlorides including the dansyl, pyrene, Lissamine rhodamine B and Texas Red derivatives, are highly reactive. These reagents are quite unstable in water, especially at the higher pH required for reaction with aliphatic amines. For example, we have determined that dilute Texas Red sulfonyl chloride is totally hydrolyzed within 2–3 minutes in pH 8.3 aqueous solution at room temperature (Lefevre C, et al., Bioconjug Chem 7, 482–489, 1996). Protein modification by this reagent is best done at low temperature. Once conjugated, however, the sulfonamides that are formed are extremely stable; they even survive complete protein hydrolysis (for example, dansyl end-group analysis (Seiler N. Methods Biochem Anal 18, 259–337, 1970). Sulfonyl chlorides can also react with phenols (including tyrosine), aliphatic alcohols (including polysaccharides), thiols (such as cysteine) and imidazoles (such as histidine), but these reactions are not common in proteins or in aqueous solution.

20. Other Amine-Reactive Reagents

Aldehydes react with amines to form Schiff bases. Notable aldehyde-containing reagents include o-phthaldialdehyde (OPA), naphthalenedicarboxaldehyde (NDA) and the 3-acylquinolinecarboxaldehyde (ATTO-TAG) reagents devised by Novotny and collaborators (Liu J P, et al., Anal Chem 63, 408–412, 1991). All of these reagents are useful for the sensitive quantitation of amines in solution, as well as by HPLC and capillary electrophoresis. In addition, certain Arylating Reagents such as NBD chloride, NBD fluoride and dichlorotriazines react with both amines and thiols, forming bonds with amines that are particularly stable.

21. Introduction of Preferred Compositions into Proteins by Using Protein Translation As an alternative to introducing the compositions of the present invention by binding to the substrate (e.g., proteins or protein fragments) such compositions can be introduced by using cellular or cell-free protein synthesizing systems. In this case, misaminoacylated tRNAs which contain the composition are introduced into a cellular or cell-free protein synthesizing system, the translation system, where they function in protein synthesis to incorporate compositions such as photocleavable biotin linked covalently to a lysine residue in place of a native amino acid such as lysine in the growing peptide chain.

For example, a photocleavable biotin-amino acid conjugate can be introduced into a protein through a tRNA using this method such that the biotin serves as A, the photoreactive moiety as PR, the amino acid is the linker L and the protein reactive group (PRG) is a tRNA.

A-L-PR-PRG

Preferably the PC-Biotin moiety is conjugated via the (-amino group of the amino acid (in this case the protein labeling occurs at the N-terminus) or via side chain such as the (-amino group of lysine or the thiol group of cysteine (in this case the labeling occurs at any site of the protein).

Once incorporated into the protein such a composition can be used as an isotope coded affinity tag as described previously. The translation systems contemplated normally comprise macromolecules including RNA and enzymes, translation, initiation and elongation factors, and chemical reagents. RNA of the system is required in three molecular forms, ribosomal RNA (rRNA), messenger RNA (mRNA) and transfer RNA (tRNA). mRNA carries the genetic instructions for building a peptide encoded within its codon sequence. tRNAs contain specific anti-codons which decode the mRNA and individually carry amino acids into position along the growing peptide chain. Ribosomes, complexes of rRNA and protein, provide a dynamic structural framework on which the translation process, including translocation, can proceed. Within the cell, individualized aminoacyl tRNA synthetases bind specific amino acids to tRNA molecules carrying the matching anticodon creating aminoacylated or charged tRNAs by the process of aminoacylation. The process of translation including the aminoacylation or charging of a tRNA molecule is described in Molecular Cell Biology (J. Darnell, et al., editors, Scientific American Books, N.Y., N.Y. 1991), which is hereby specifically incorporated by reference. Aminoacylation may be natural or by artificial means utilizing native amino acids, non-native amino acid, amino acid analogs or derivatives, or other molecules such as detectable chemicals or coupling agents. The resulting misaminoacylated tRNA comprises a native amino acid coupled with a chemical moiety, non-native amino acid, amino acid derivative or analog, or other detectable chemicals. These misaminoacylated tRNAs incorporate their markers into the growing peptide chain during translation forming labeled nascent proteins which can be detected and isolated by the presence or absence of the marker.

Any proteins that can be expressed by translation in a cellular or cell-free translation system may be nascent proteins and consequently can isotope coded affinity tags can be incorporated by the methods of the invention. Examples of such proteins include enzymes such as proteolytic proteins, cytokines, hormones, immunogenic proteins, carbohydrate or lipid binding proteins, nucleic acid binding proteins, human proteins, viral proteins, bacterial proteins, parasitic proteins and fragments and combinations. These methods are well adapted for the detection of products of recombinant genes and gene fusion products because recombinant vectors carrying such genes generally carry strong promoters which transcribe mRNAs at fairly high levels. These mRNAs are easily translated in a translation system.

Translation systems may be cellular or cell-free, and may be prokaryotic or eukaryotic. Cellular translation systems include whole cell preparations such as permeabilized cells or cell cultures wherein a desired nucleic acid sequence can be transcribed to mRNA and the mRNA translated.

Cell-free translation systems are commercially available and many different types and systems are well-known. Examples of cell-free systems include prokaryotic lysates such as Escherichia coli lysates, and eukaryotic lysates such as wheat germ extracts, insect cell lysates, rabbit reticulocyte lysates, rabbit oocyte lysates and human cell lysates. Eukaryotic extracts or lysates may be preferred when the resulting protein is glycosylated, phosphorylated or otherwise modified because many such modifications are only possible in eukaryotic systems. Some of these extracts and lysates are available commercially (Promega; Madison, Wis.; Stratagene; La Jolla, Calif.; Amersham; Arlington Heights, Ill.; GIBCO/BRL; Grand Island, N.Y.). Membranous extracts, such as the canine pancreatic extracts containing microsomal membranes, are also available which are useful for translating secretory proteins. Mixtures of purified translation factors have also been used successfully to translate mRNA into protein as well as combinations of lysates or lysates supplemented with purified translation factors such as initiation factor-1(IF-1), IF-2, IF-3 (.alpha. or .beta.), elongation factor T (EF-Tu), or termination factors.

Cell-free systems may also be coupled transcription/translation systems wherein DNA is introduced to the system, transcribed into mRNA and the mRNA translated as described in Current Protocols in Molecular Biology (F. M.

Ausubel, et al., editors, Wiley Interscience, 1993), which is hereby specifically incorporated by reference. RNA transcribed in eukaryotic transcription system may be in the form of heteronuclear RNA (hnRNA) or 5'-end caps (7-methyl guanosine) and 3'-end polyA tailed mature mRNA, which can be an advantage in certain translation systems. For example, capped mRNAs are translated with high efficiency in the reticulocyte lysate system. tRNA molecules chosen for misaminoacylation with marker do not necessarily possess any special properties other than the ability to function in the protein synthesis system. Due to the universality of the protein translation system in living systems, a large number of tRNAs can be used with both cellular and cell-free reaction mixtures. Specific tRNA molecules which recognize unique codons, such as nonsense or amber codons (UAG), are not required.

Site-directed incorporation of the nonnative analogs into the protein during translation is also not required. Incorporation of markers can occur anywhere in the polypeptide and can also occur at multiple locations. This eliminates the need for prior information about the genetic sequence of the translated MRNA or the need for modifying this genetic sequence.

In some cases, it may be desirable to preserve the functional properties of the nascent protein. A subset of tRNAs which will incorporate markers at sites which do not interfere with protein function or structure can be chosen. Amino acids at the amino or carboxyl terminus of a polypeptide do not alter significantly the function or structure. tRNA molecules which recognize the universal codon for the initiation of protein translation (AUG), when misaminoacylated with marker, will place marker at the amino terminus. Prokaryotic protein synthesizing systems utilize initiator tRNA$^{fMet}$ molecules and eukaryotic systems initiator tRNA$^{Met}$ molecules. In either system, the initiator tRNA molecules are aminoacylated with markers which may be non-native amino acids or amino acid analogs or derivatives that possess marker, reporter or affinity properties. The resulting nascent proteins will be exclusively labeled at their amino terminus, although markers placed internally do not necessarily destroy structural or functional aspects of a protein. For example, a tRNA$^{Lys}$ may be misaminoacylated with the amino acid derivative dansyl-lysine which does not interfere with protein function or structure. In addition, using limiting amounts of misaminoacylated tRNAs, it is possible to detect and isolate nascent proteins having only a very small fraction labeled with marker which can be very useful for isolating proteins when the effects of large quantities of marker would be detrimental or are unknown. tRNAs molecules used for aminoacylation are commercially available from a number of sources and can be prepared using well-known methods from sources including *Escherichia coli*, yeast, calf liver and wheat germ cells (Sigma Chemical; St. Louis, Mo.; Promega; Madison, Wis.; Boehringer Mannheim Biochemicals; Indianapolis, Ind.). Their isolation and purification mainly involves cell-lysis, phenol extraction followed by chromatography on DEAE-cellulose. Amino-acid specific tRNA, for example tRNA$^{fMet}$, can be isolated by expression from cloned genes and overexpressed in host cells and separated from total tRNA by techniques such as preparative polyacrylamide gel electrophoresis followed by band excision and elution in high yield and purity (Seong and RajBhandary, Proc. Natl. Acad. Sci. USA 84:334–338, 1987). Run-off transcription allows for the production of any specific tRNA in high purity, but its applications can be limited due to lack of post-transcriptional modifications (Bruce and Uhlenbeck, Biochemistry 21:3921, 1982).

Misaminoacylated tRNAs are introduced into the cellular- or cell-free protein synthesis system. In the cell-free protein synthesis system, the reaction mixture contains all the cellular components necessary to support protein synthesis including ribosomes, tRNA, rRNA, spermidine and physiological ions such as magnesium and potassium at appropriate concentrations and an appropriate pH. Reaction mixtures can be normally derived from a number of different sources including wheat germ, *E. coli* (S-30), red blood cells (reticulocyte lysate,) and oocytes, and once created can be stored as aliquots at about +4.degree. C. to 70° C. The method of preparing such reaction mixtures is described by J. M. Pratt (Transcription and Translation, B. D. Hames and S. J. Higgins, Editors, p. 209, IRL Press, Oxford, 1984) which is hereby incorporated by reference. Many different translation systems are commercially available from a number of manufacturers.

The misaminoacylated tRNA is added directly to the reaction mixture as a solution of predetermined volume and concentration. This can be done directly prior to storing the reaction mixture at −70° C. in which case the entire mixture is thawed prior to initiation of protein synthesis or prior to the initiation of protein synthesis. Efficient incorporation of markers into nascent proteins is sensitive to the final pH and magnesium ion concentration. Reaction mixtures are normally about pH 6.8 and contain a magnesium ion concentration of about 3 mM. These conditions impart stability to the base-labile aminoacyl linkage of the misaminoacylated tRNA. Aminoacylated tRNAs are available in sufficient quantities from the translation extract. Misaminoacylated tRNAs charged with markers are added at between about 1.0 μg/ml to about 1.0 mg/ml, preferably at between about 10 .μg/ml to about 500 .mu.g/ml, and more preferably at about 150 .μg/ml.

Initiation of protein synthesis occurs upon addition of a quantity of mRNA or DNA to the reaction mixture containing the misaminoacylated tRNAs. mRNA molecules may be prepared or obtained from recombinant sources, or purified from other cells by procedure such as poly-dT chromatography. One method of assuring that the proper ratio of the reaction mixture components is to use predetermined volumes that are stored in convenient containers such as vials or standard microcentrifuge tubes. For example, DNA and/ or mRNA coding for the nascent proteins and the misaminoacylated tRNA solution are premixed in proper amounts and stored separately in tubes. Tubes are mixed when needed to initiate protein synthesis.

Translations in cell-free systems generally require incubation of the ingredients for a period of time. Incubation times range from about 5 minutes to many hours, but is preferably between about thirty minutes to about five hours and more preferably between about one to about three hours. Incubation may also be performed in a continuous manner whereby reagents are flowed into the system and nascent proteins removed or left to accumulate using a continuous flow system (A. S. Spirin et al., Sci. 242:1162–64, 1988). This process may be desirable for large scale production of nascent proteins. Incubation times vary significantly with the volume of the translation mix and the temperature of the incubation. Incubation temperatures can be between about 4° C. to about 60° C., and are preferably between about 15° C. to about 50° C., and more preferably between about 25° C. to about 45° C. and even more preferably at about 25° C. or about 37° C. Certain markers may be sensitive to temperature fluctuations and in such cases, it is preferable to conduct those incubations in the non-sensitive ranges. Translation mixes will typically comprise buffers such as Tris-HCl, Hepes or another suitable buffering agent to maintain the pH of the solution between about 6 to 8, and preferably at about 7. Again, certain markers may be pH sensitive and in such cases, it is preferable to conduct incubations outside of the sensitive ranges for the marker. Translation efficiency may not be optimal, but marker utility will be enhanced. Other reagents which may be in the translation system include dithiothreitol (DTT) or 2-mercaptoethanol as reducing agents, RNasin to inhibit RNA breakdown, and nucleoside triphosphates or creatine phosphate and creatine kinase to provide chemical energy for the translation process.

In cellular protein synthesis, it is necessary to introduce misaminoacylated tRNAs or markers into intact cells, cell organelles, cell envelopes and other discrete volumes bounded by an intact biological membrane, which contain a protein synthesizing system. This can be accomplished through a variety of methods that have been previously established such as sealing the tRNA solution into liposomes or vesicles which have the characteristic that they can be induced to fuse with cells. Fusion introduces the liposome or vesicle interior solution containing the tRNA into the cell. Alternatively, some cells will actively incorporate liposomes into their interior cytoplasm through phagocytosis. The tRNA solution could also be introduced through the process of cationic detergent mediated lipofection (Felgner, et al., Proc. Natl. Acad. Sci. USA 84:7413–17, 1987), or injected into large cells such as oocytes. Injection may be through direct perfusion with micropipettes or through the method of electroporation.

Alternatively, cells can be permeabilized by incubation for a short period of time in a solution containing low concentrations of detergents in a hypotonic media. Contemplated detergents include Nonidet-P 40 (NP40), Triton X-100 (TX-100) or deoxycholate at concentrations of about 0.01 µM to 1.0 mM, preferably between about 0.1 µM to about 0.01 mM, and more preferably about 1 µM. Permeabilized cells allow marker to pass through cellular membranes unaltered and be incorporated into nascent proteins by host cell enzymes. Such systems can be formed from intact cells in culture such as bacterial cells, primary cells, immortalized cell lines, human cells or mixed cell populations. These cells may, for example, be transfected with an appropriate vector containing the gene of interest, under the control of a strong and possibly regulated promoter. Messages are expressed from these vectors and subsequently translated within cells. Intact misaminoacylated tRNA molecules, already charged with a non-radioactive marker could be introduced to cells and incorporated into translated product.

The misaminoacylated tRNA can be formed by natural aminoacylation using cellular enzymes or misaminoacylation such as chemical misaminoacylation. One type of chemical misaminoacylation involves truncation of the tRNA molecule to permit attachment of the marker or marker precursor. For example, successive treatments with periodate plus lysine, pH 8.0, and alkaline phosphatase removes 3-terminal residues of any tRNA molecule generating tRNA-OH-3' with a mononucleotide or dinucleotide deletion from the 3'-terminus (Neu and Heppel, J. Biol. Chem. 239:2927–34, 1964). Alternatively, tRNA molecules may be genetically manipulated to delete specific portions of the tRNA gene. The resulting gene is transcribed producing truncated tRNA molecules (Sampson and Uhlenbeck, Proc. Natl. Acad. Sci. USA 85:1033–37, 1988). Next, a dinucleotide is chemically linked to a modified amino acid or other marker by, for example, acylation. Using this procedure, markers can be synthesized and acylated to dinucleotides in high yield (Hudson, J. Org. Chem. 53:617–624, 1988; Happ et al., J. Org. Chem. 52:5387–91, 1987). These modified groups are bound together and linked via the dinucleotide to the truncated tRNA molecules in a process referred to as ligase coupling.

Figure 28:
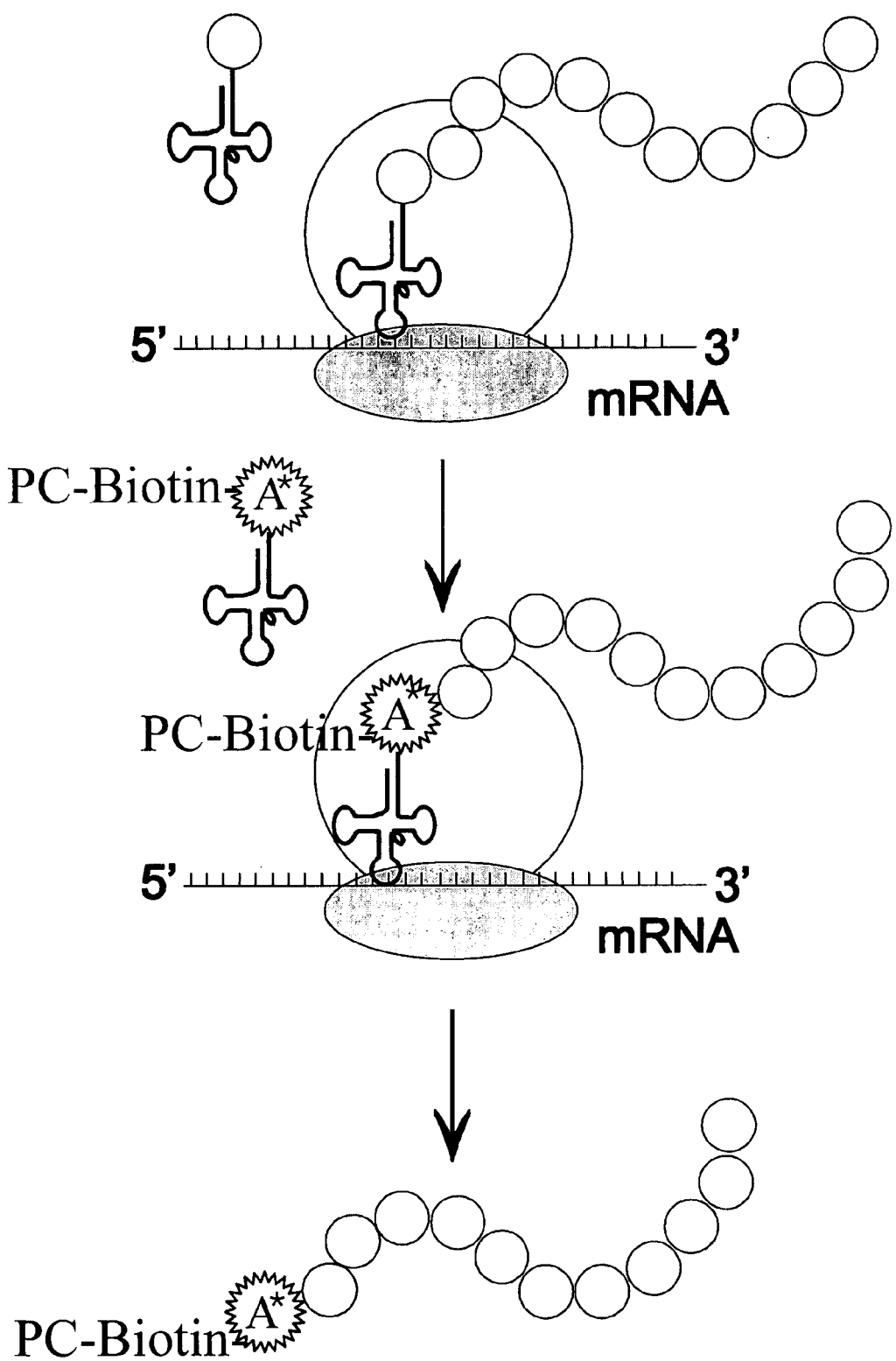
FIG. 28 depicts incorporation of PC-ICAT into proteins via the tRNA, which is aminoacylated with PC-Biotin conjugated amino acid (A), which carries stable isotope label.
Figure 29:
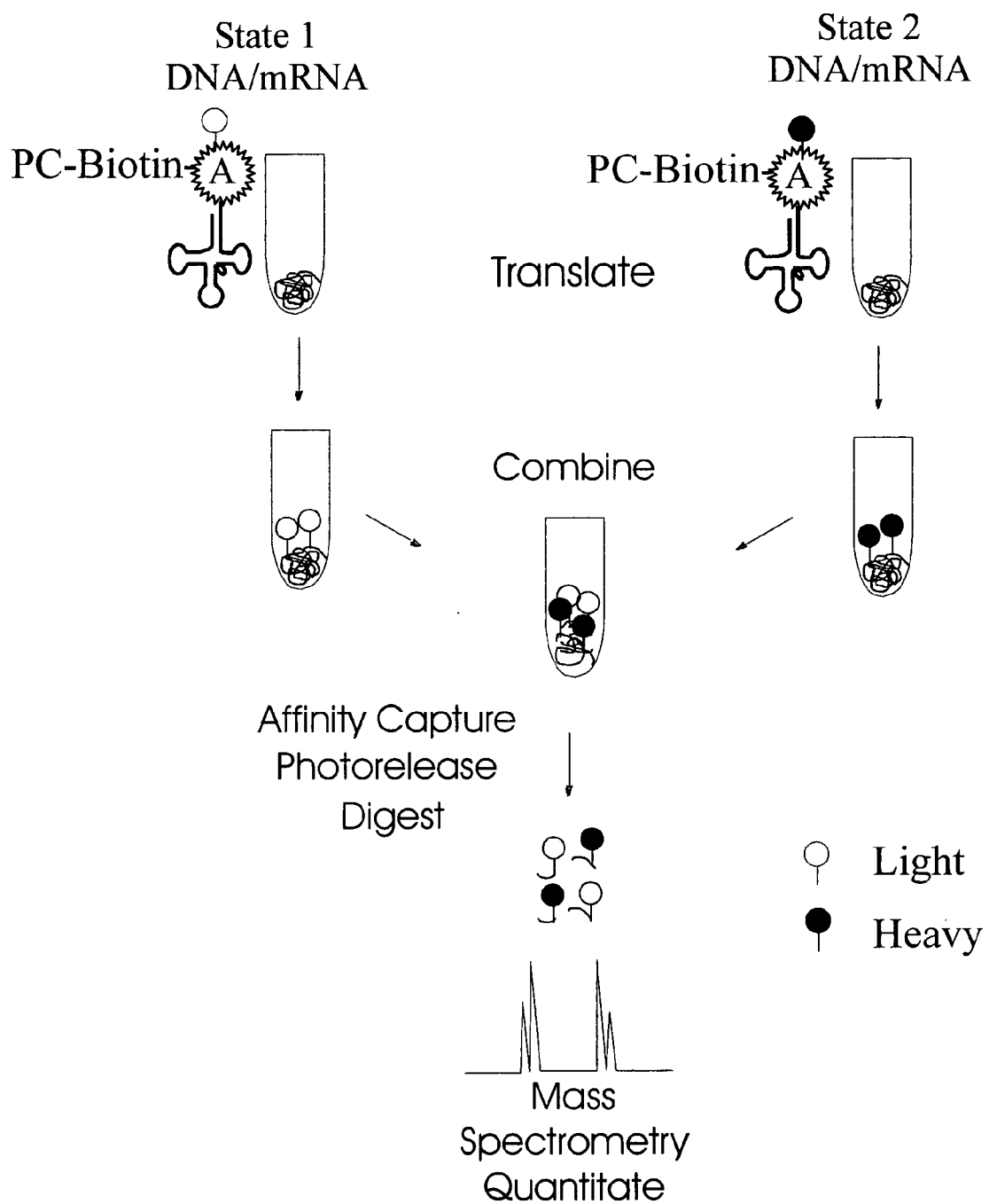
FIG. 29 illustrates protein abundance determination using translation with tRNAs labeled with light and heavy PC-ICAT.
Figure 30:
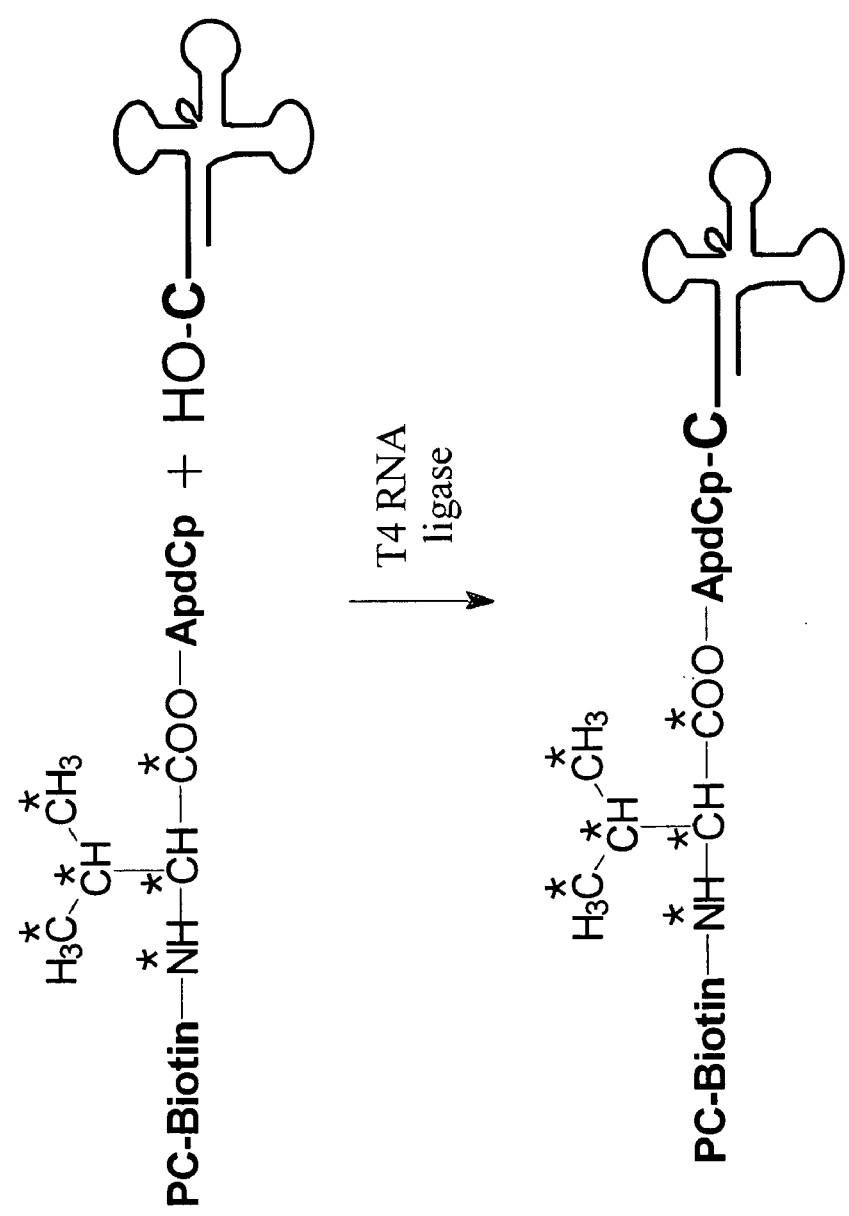
FIG. 30 illustrates the preparation of PC-Biotin-Valine-tRNA conjugate useful in performing protein abundance determination mediated by tRNA labeling at the N-terminal position of proteins. The valine amino acid contains stable isotopes.

An example of an introduction of PC-ICAT using protein translation is shown in FIGS. 28 and 29. A PC-biotin-amino acid is linked to tRNA via its carboxyl group and 2'(3')-OH group on the terminal adenosine of the tRNA to from PC-Biotin-aminoacylated tRNA. This tRNA is then added to a cellular or cell-free translation system and the PC-ICAT amino acid (PC-Biotin amino-acid) is incorporated into nascent protein. For example, the tRNA may consist of a $tRNA^{Lys}$ in which case the PC-biotin-lysine amino acid will be incorporated randomly into lysine positions in the protein. Alternatively, the tRNA may consist of an initiator tRNA whereby the PC-biotin-amino acid moiety will be incorporated at the N-terminal position of the protein (FIG. 30). In this case any isotopically labelled amino acid can be modified with PC-Biotin and incorporated at the N-terminus. It is also possible to utilize a mixture of tRNAs which are chemically misaminoacylated with the PC biotin-lysine conjugate. The methods for the preparation of chemically aminoacylated tRNAs are described in U.S. patent application Ser. No. 10/345,664 (filed Jan. 16, 2003), which is herein incorporated in its entirety as a reference. In this case, the lysine-biotin will be incorporated randomly in a variety of different amino acids throughout the protein sequence. The lysine which is incorporated into the nascent protein as part of a PC-biotin-lysine complex can function as a linker group, wherein said linker group comprises, for example, stable isotopes, such as deuterium, $^{13}C$, $^{15}N$ or other molecules to allow for the production of variants distinguishable by mass spectrometry. Linker groups with stable isotopes function as detectable groups. This allows for the comparison of two populations, e.g., one with the "heavy" reagent and the other with the "light" non-labeled reagent, both introduced separately using misaminoacylated tRNAs. This approach is shown in FIG. 29.

Figure 31:
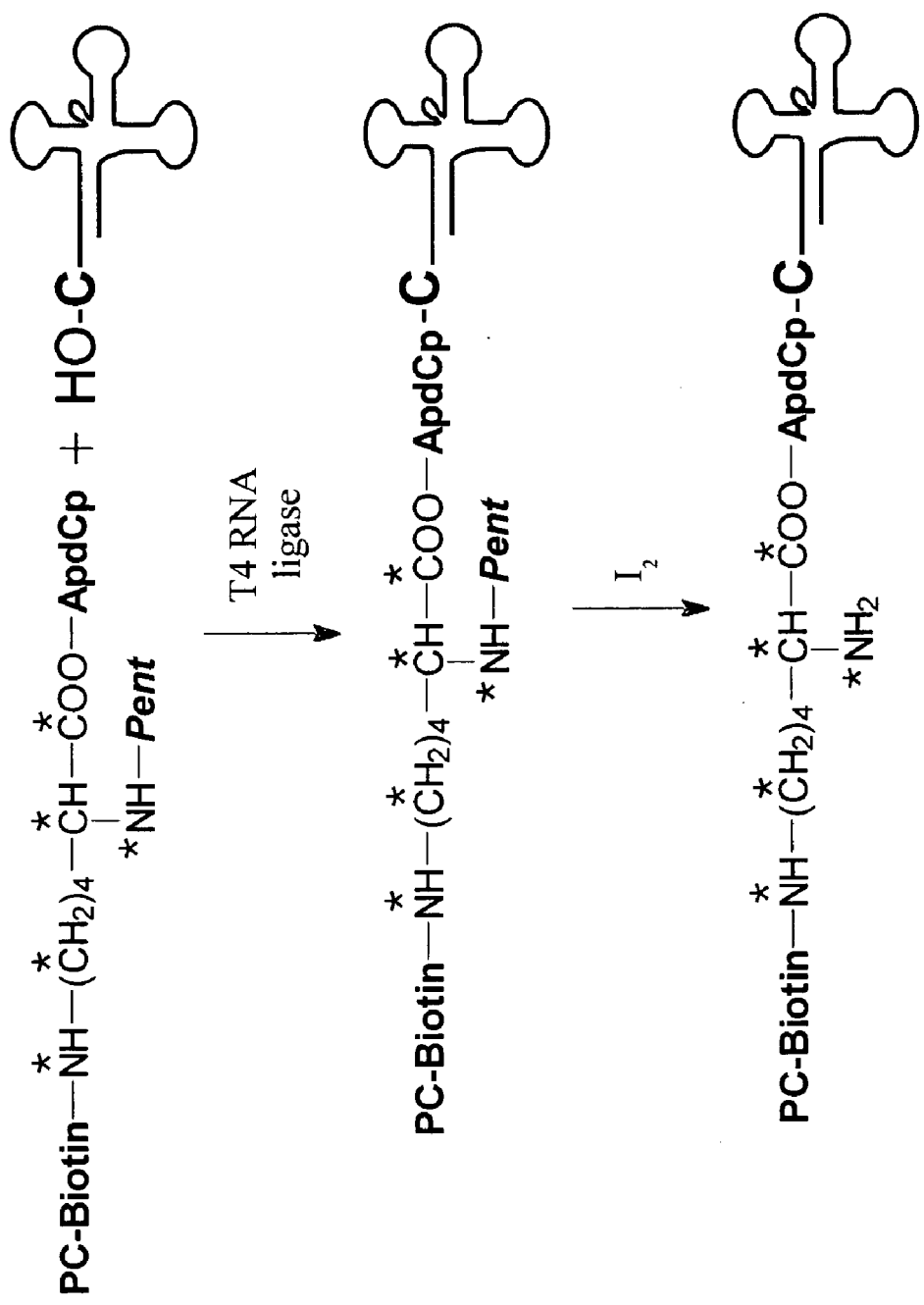
FIG. 31 illustrates the preparation of PC-Biotin-Lysine-tRNA conjugate useful in performing protein abundance determination mediated by tRNA labeling at any position of proteins. The lysine amino acid contains stable isotopes.
Figure 32:
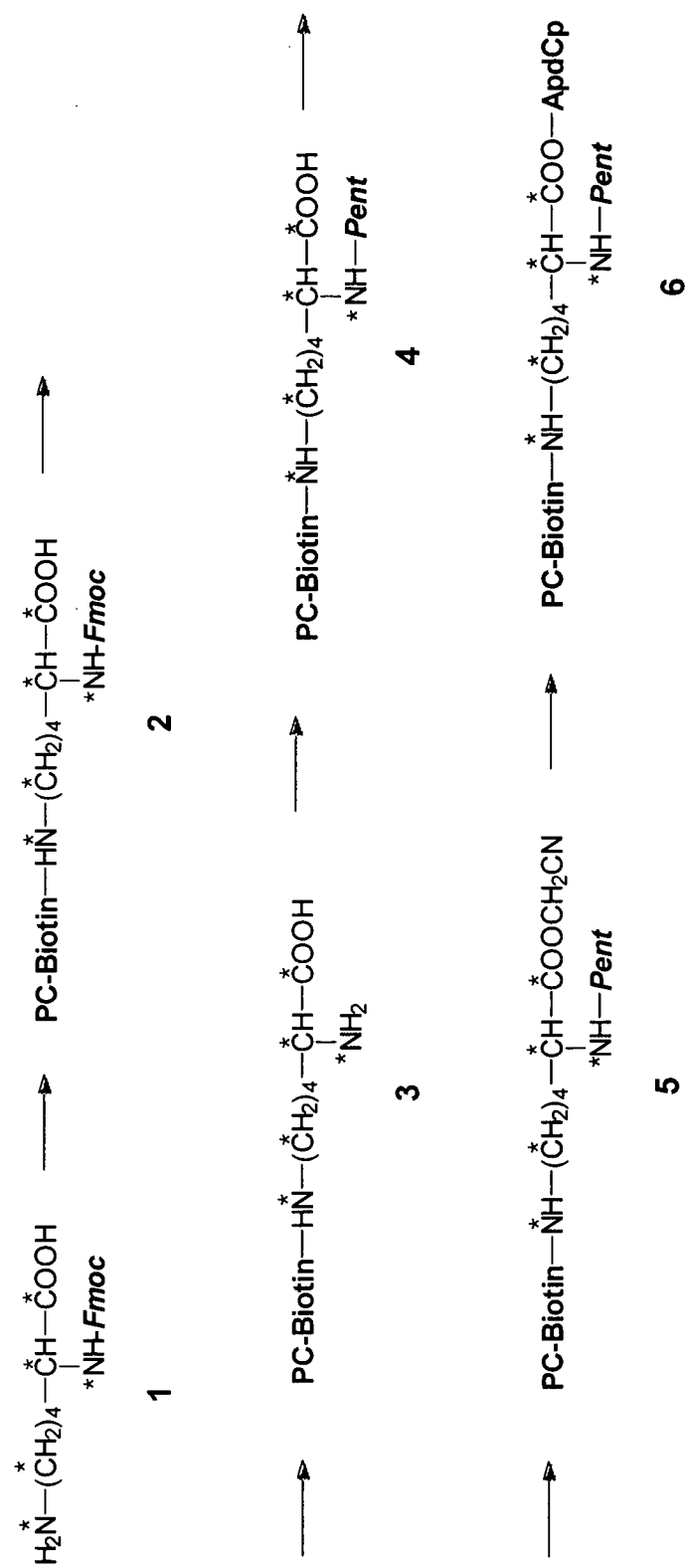
FIG. 32 illustrates steps in the preparation of PC-Biotin-lysine-pdCpA dinucleotide useful in preparing PC-ICAT tRNA conjugates. The lysine amino acid contains stable isotopes.

In one embodiment of the present invention, a protein is synthesized in a cell-free or cellular protein expression system using a tRNA misaminoacylated with PC-biotin-lysine (FIG. 31). Changes in expression level due to a stimulus can be detected using mass spectrometric analysis by using unlabelled and isotopically labeled lysines similar to analysis performed using proteins which are chemically labeled with isotope coded affinity tags (FIG. 29). One advantage of this approach compared to chemical labeling of the protein mixtures of this invention is that in a complex mixture only nascent proteins will contain the composition or label. An example of the synthesis of the PC_Biotin-Lys-pdCpA dinucleotide useful in the preparation of PC-ICAT tRNAs is shown in FIG. 32.

Experimental

The following examples are offered to illustrate various embodiments of the invention, but should not be viewed as limiting the scope of the invention.

EXAMPLE 1

Figure 12:
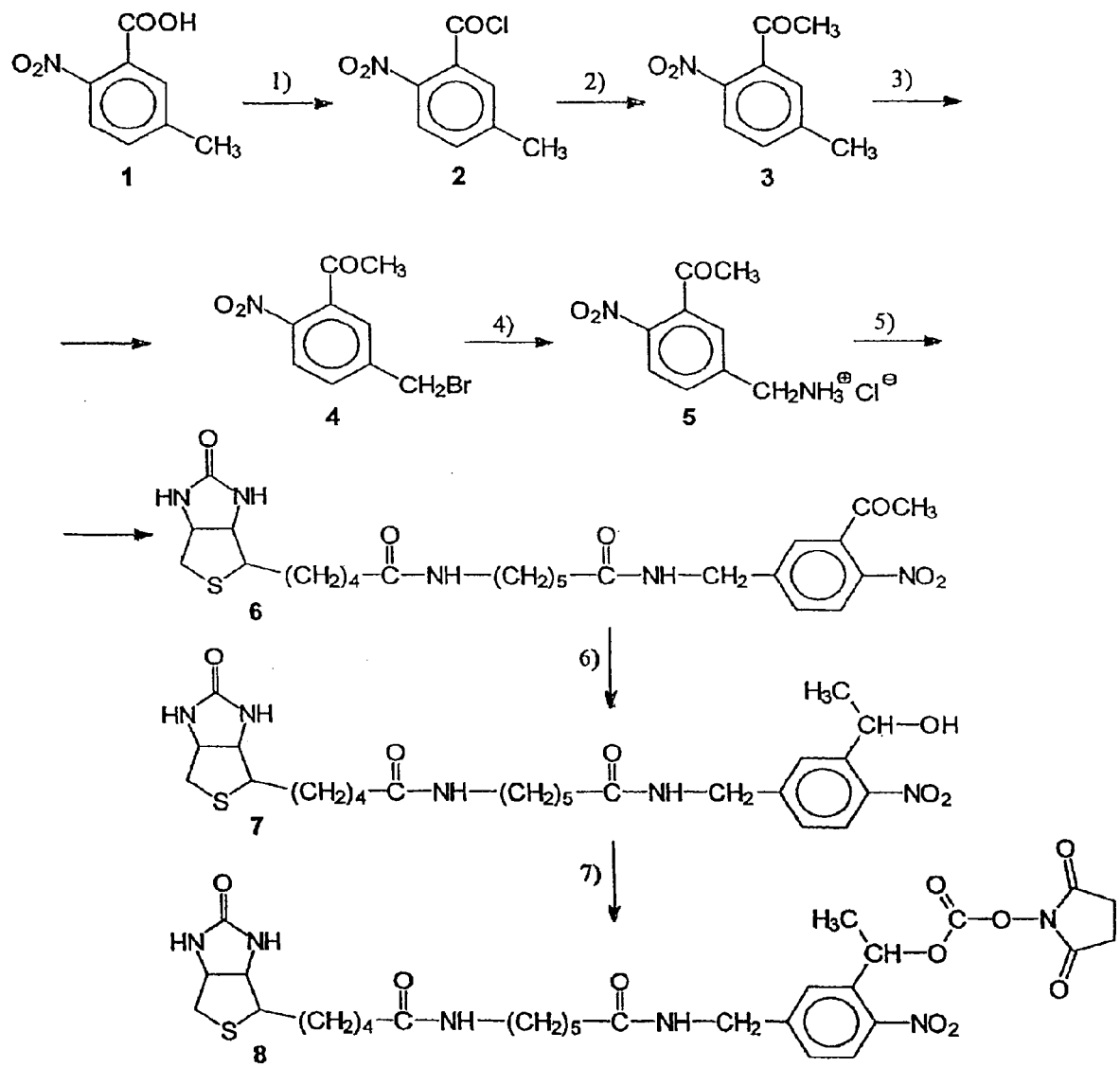
FIG. 12 shows a diagram depicting steps in one embodiment of the synthesis of PC-Biotin-NHS ester.

Photocleavable Biotin NHS carbonate (see, FIG. 12). This example shows the synthesis of a photocleavable Biotin NHS carbonate. 5-methyl-2-nitrobenzoic acid (1) (5 g; 27.6 mmol) was added in small portions to thionyl chloride (16.4 g; 138 mmol). After 10 hrs of stirring at room temperature excess of thionyl chloride was evaporated to give the acid chloride (2). Magnesium turnings (1.07 g; 44.2 mmol), absolute ethanol (6 ml), chlorobenzene (8 ml) and 0.1 mg of dry $CCL_4$ were refluxed for 2 hrs. Diethyl malonate (4.82 g; 30 mmol in 10 ml of chlorobenzene) was added, followed by the addition of the acid chloride (2) (5.49 g; 27.5 mmol in 10 ml chlorobenzene). The reaction mixture was stirred for 1 hr, acidified with 20 ml of 2N sulfuric acid, extracted with chloroform (3×20 ml), dried and evaporated to dryness. The residue was dissolved in acetic acid (8.25 ml), 5.4 ml of $H_2O$ and 1 ml of concentrated $H_2SO_4$ were added and the mixture was refluxed for 6 hrs. The reaction mixture was neutralized with aq. $Na_2CO_3$ and extracted with $CHCl_3$ (3×20 ml). Chloroform extracts were combined, dried and after removing the solvents in vacuo, the residue was crystallized from 95% ethanol to give 5-methyl-2-nitroacetophenone (3) (4.46 g, 81%). Compound (3) (3.51 g; 19.6 mmol), N-bromosuccinimide (3.66 g; 20.6 mmol) and benzoyl peroxide (46 mg; 0.01 eq.) were refluxed in 20 ml of $CCl_4$ for 5 hrs. The precipitate was filtered off, filtrate evaporated and the residue crystallized from $CCl_4$ to give 5-bromomethyl-2-nitroacetophenone (4) (3.64 g, 72%). Compound (4) (2.0 g; 7.75 mmol) was added to a solution of hexamethylenetramine (1.14 g; 8.13 mmol) in 15 ml of chlorobenzene. The mixture was stirred overnight, the resulting precipitate of 5-aminimethyl-22-nitroacetophenone hydrochloride (5) filtered off and washed with chlorobenzene (10 ml) and diethyl ether (20 ml). The precipitate (2.93 g; 7.36 mmol) was suspended in 39 ml of chlorobenzene and 19.5 ml of methanol. To this suspension 4.9 ml of concentrated HCl was added and the mixture was stirred overnight. 70 ml of diethyl ether was then added and the resulting precipitate washed with 2×50 ml of ether and dried under vacuum. Dimethylformamide (10 ml) was added followed by addition of a 5-biotinamidocaproic acid (3.29 g; 1.25 eq., in 35 ml of N-methylpyrrolidone), dicyclohexylcarbodiimide (2.28 g; 1.5 eq.) and triethylamine (1.28 ml; 1.25 eq.). This solution was stirred overnight at room temperature, the precipitate was filtered off and the filtrate was added to 700 ml of diethyl ether. The resulting precipitate was dried and purified on a silica gel column using step gradient (5–20%) of MeOH in $CHCl_3$ to give 5-(5-biotinamidocaproamidomethyl)-1-(2-nitrophenyl (6) (2.27 g, 58%).

Intermediate 6 (1 g; 1.87 mmol) was dissolved in 15 ml of 70% EtOH, and after cooling the solution to 0° C., sodium borohydride (141 mg; 4 eq.) was added. The solution was stirred at 0° C. for 30 min. and at room temperature for an additional 2 hrs. The reaction was quenched by addition of 1 ml acetone neutralized with 0.1 N HCl and concentrated to about 5 ml. Aqueous layer was decanted and the residue was washed with water (3×5 ml) and dried to give 5-(5-biotinamidocaproamidomethyl)-1-(2-nitrophenyl)ethanol (7) (0.71 g, 71%).

Compound 7 (1.07 g: 2 mmol) was dissolved in 10 ml dimethylformamide. To this solution N,N'-disuccinimidyl carbonate (Fluka) (1 g; 1.5 eq.) Was added followed by triethylamine (0.81 ml; 3 eq.). After 5 hr. of stirring at room temperature solvents were evaporated to dryness and the residue was applied to silica gel column and purified using step gradient of methanol in chloroform to give 1.04 g (69%) of 5-(5-biotinamidocaproamidonethyl)-1-(2-nitrophenyl) ethyl-N-hydroxysuccinimidyl carbonate (PC-Biotin-NHS) ester (8) which was characterized as follows: mp=113–114° C. (uncorrected); Cl-MS (M$^+$=676.5); UV-VIS (in phosphate buffer, pH=7.4) $\lambda_1$=204 nm, $\epsilon1$=19190 M$^{-1}$ cm$^{-1}$; $\lambda_2$=272 nm, $\epsilon_2$=6350 M$^{-1}$ cm$^{-1}$; $^1$H NMR [δ; ppm]: 8.48(t, 1H), 8.05–8.03(d,1H), 7.75–7.71(t,1H), 7.66(s,1H), 7.46–7.45(d,1H), 6.44(s,1H), 6.37(s,1H) 6.28–6.27(m,1H), 4.39(m,2H), 4.30(m,1H), 4.12(m,1H), 3.57(d,2H), 3.09(m, 1H), 3.01–2.99(m,2H), 2.79(m,5H), 2.58–2.55(d,1H), 2.17–2.15(m,2H), 2.04–2.02(m,2H), 1.72–1.71(m,2H), 1.66–1.43(m, br, 6H), 1.38–1.36(m, br, 2H), 1.26–1.25(m, br, 3H); IR (KBr): $v_{c=o}$ 1815 and 1790 cm$^{-1}$.

EXAMPLE 2

Figure 13:
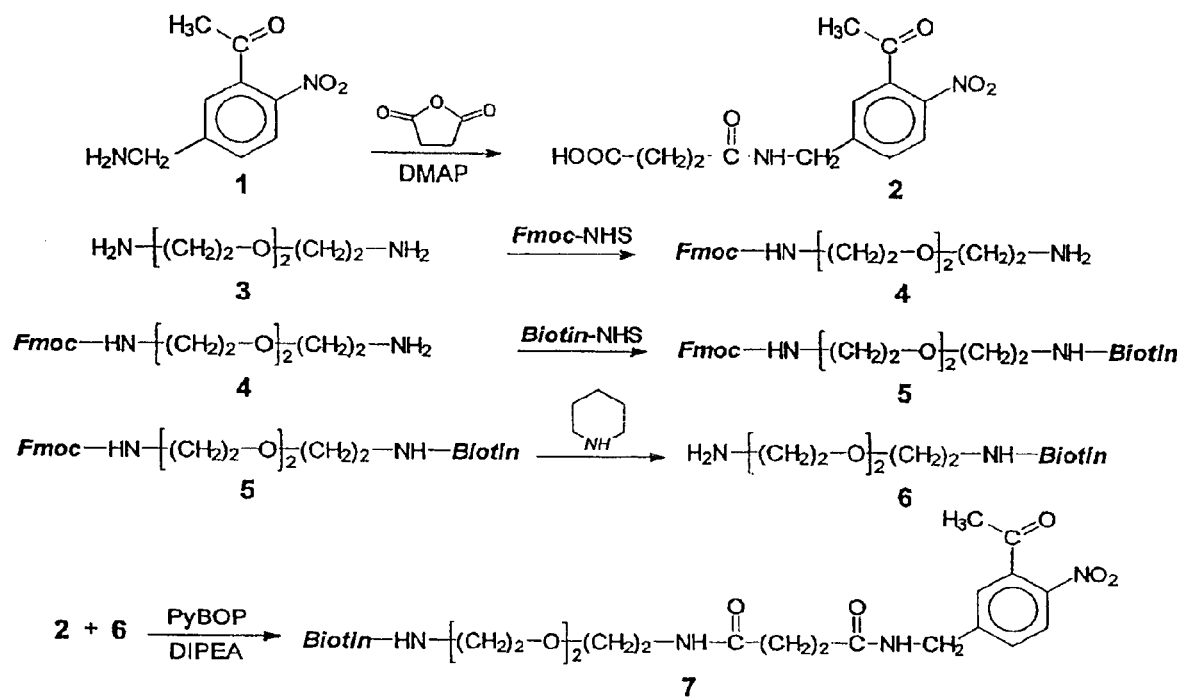
FIG. 13 shows a diagram depicting steps in one embodiment of the synthesis of water soluble PC-Biotin-NHS ester.

Water soluble PC-Biotin synthesis (see, FIG. 13). The example shows the synthesis of a water soluble PC-Biotin. 5-aminomethyl-2-nitroacctophenoe hydrochloride (1.73 g, 7.5 mmol) (FIG. 13, compound 1) was dissolved in 60 ml DMF. To this solution was added DIPEA (N,N,-diisopropylethylamine) (1.2 ml) DMAP (dimethylaminopyridine ) (0.46 g; 3.75 mmol) and succinic anhydride (0.75 g, 7.5 mmol). The reaction was stirred at room temperature overnight, added to 120 ml of 0.1 N HCl and extracted with 3×50 ml chloroform. Organic extracts were combined, dried and evaporated. Crude product was recrystallized from acetonitrile to give compound 2 (1.2 g, 49% yield).

To a stirred solution of 2,2'-(ethylenedioxy)-bis-(ethylamine) 3 (2 g; 13.5 mmol) in 100 ml of acetonitrile a solution of Fmoc-NHS (9-fluorenylmethyloxycarbonyl-NHS) (4.95 g, 14.8 mmol) in 50 ml acetonitrile was added during 30 minutes. The reaction mixture was stirred for additional 1 hr, concentrated under reduced pressure and purified on a silica gel using 0–6% step gradient of methanol in chloroform/0.8% triethylamine. Fractions containing mono-Fmoc derivative were polled and evaporated to give 2.50 g of compound 4 (52% yield).

To a stirred solution of compound 4 (2.5 g, 7 mmol) in 50 ml of methanol a solution of biotin-NHS (2.63 g, 7.7 mmol) in 60 ml of 95% methanol was added during 15 minutes. After additional 1 hr at room temperature TLC (chloroform/methanol/AcOH, 9:1:1 v/v/v) showed complete conversion into intermediate 3. The mixture was then concentrated under reduced pressure and purified on a silica gel using a 0–6% step gradient of MeOH in chloroform to give 2.2 g of intermediate 5 (54% yield).

Compound 5 (2.2 g, 3.8 mmol) was added to 6 ml of 20% piperidine in DMF. The resulting solution was stirred at room temperature for 10 minutes, concentrated under reduced pressure to about 2 ml and added to 20 ml of cold ether. After 30 minutes incubation at –70 ° C. the precipitate was isolated by centrifugation (4,000 rpm, 10 minutes). The precipitate (compound 6) was dissolved in 2 ml of methanol, reprecipitated as above and dried. Yield 1.1 g (82%).

Intermediate 2 (0.59 g, 1.94 mmol) was dissolved in 3 ml of DMF, to this solution was added a solution of PyBOP (Benzotriazol-1-yl-oxytripyrrolidinophosphonium hexafluorophosphate) (0.99 g, 1.94 mmol) in ml DMF followed by N,N-diisopropylethylamine (0.68 g, 3.9 mmol). The resulting solution was stirred at room temperature for 15 minutes and then a solution of Compound 6 (0.68 g, 1.94 mmol) in 3 ml DMF was added. Stirring continued overnight, solvents were evaporated under reduced pressure and the residue purified on a silica gel column using step gradient (0–20%) of methanol in chloroform to give 0.75 g of compound 7 (67% yield).

Reduction with sodium borohydride and conversion to the target N-hydroxysuccinimidyl carbonate was carried out as in the case described previously (Olejnik, et al., Proc. Natl. Acad. Sci. USA, 92, 7590–7594, 1995) to give the target water soluble PC-biotin NHS carbonate (Pondori, et al., Chem. Biol., 9(5), 567–573).

Figure 14A:
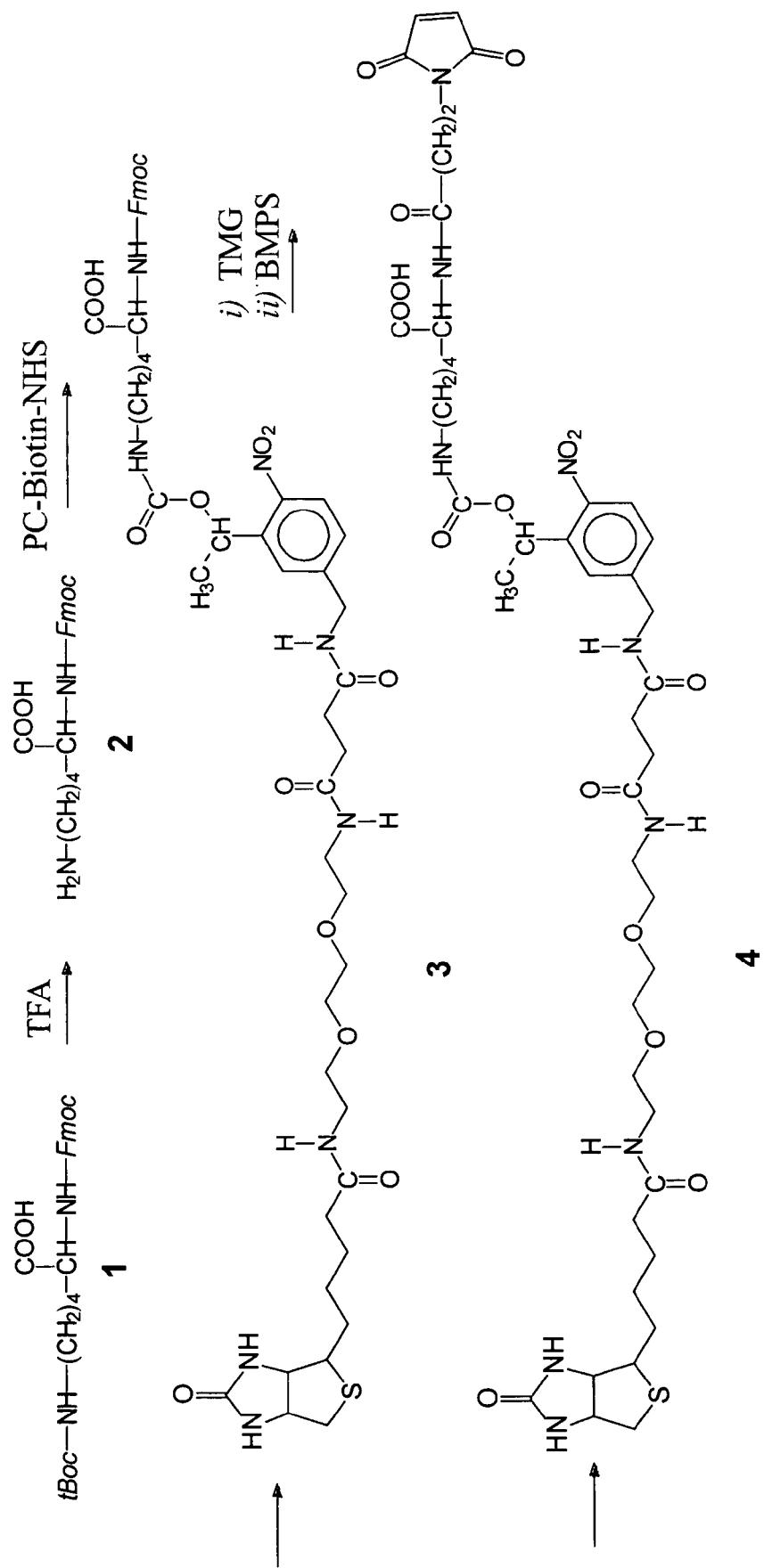
FIG. 14A shows a diagram depicting steps in one embodiment of the synthesis of water soluble PC-Biotin-lysine-maleimide conjugate.

EXAMPLE 3

α-Fmoc, ε-PC-Biotin-Lys(U-$^{12}C_6$,$^{14}N_2$)—OH (Compound 3, FIG. 14A)

Figure 14B:
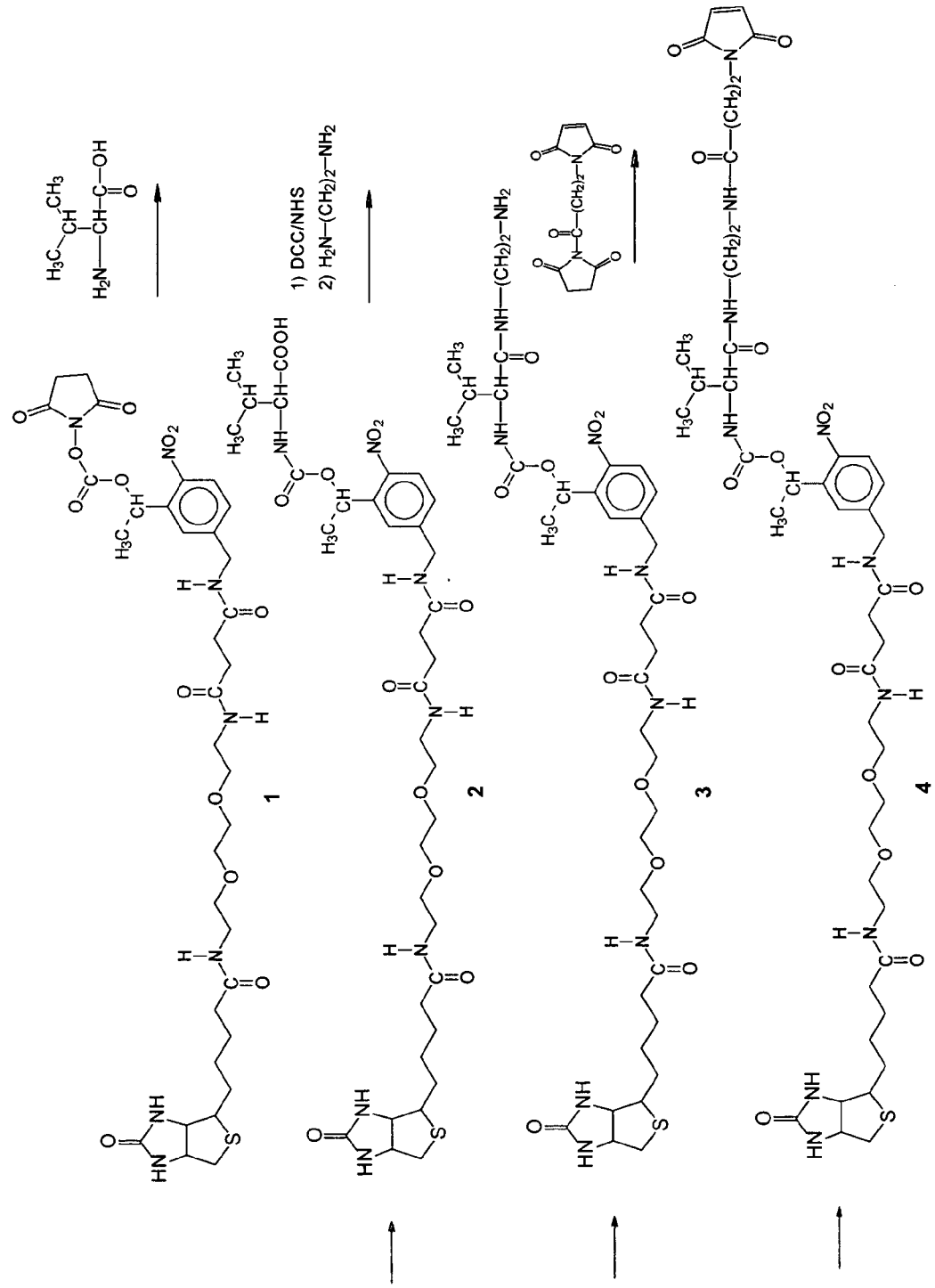
FIG. 14B shows a diagram depicting steps in one embodiment of the synthesis of water soluble PC-Biotin-valine-maleimide conjugate.
Figure 14C:
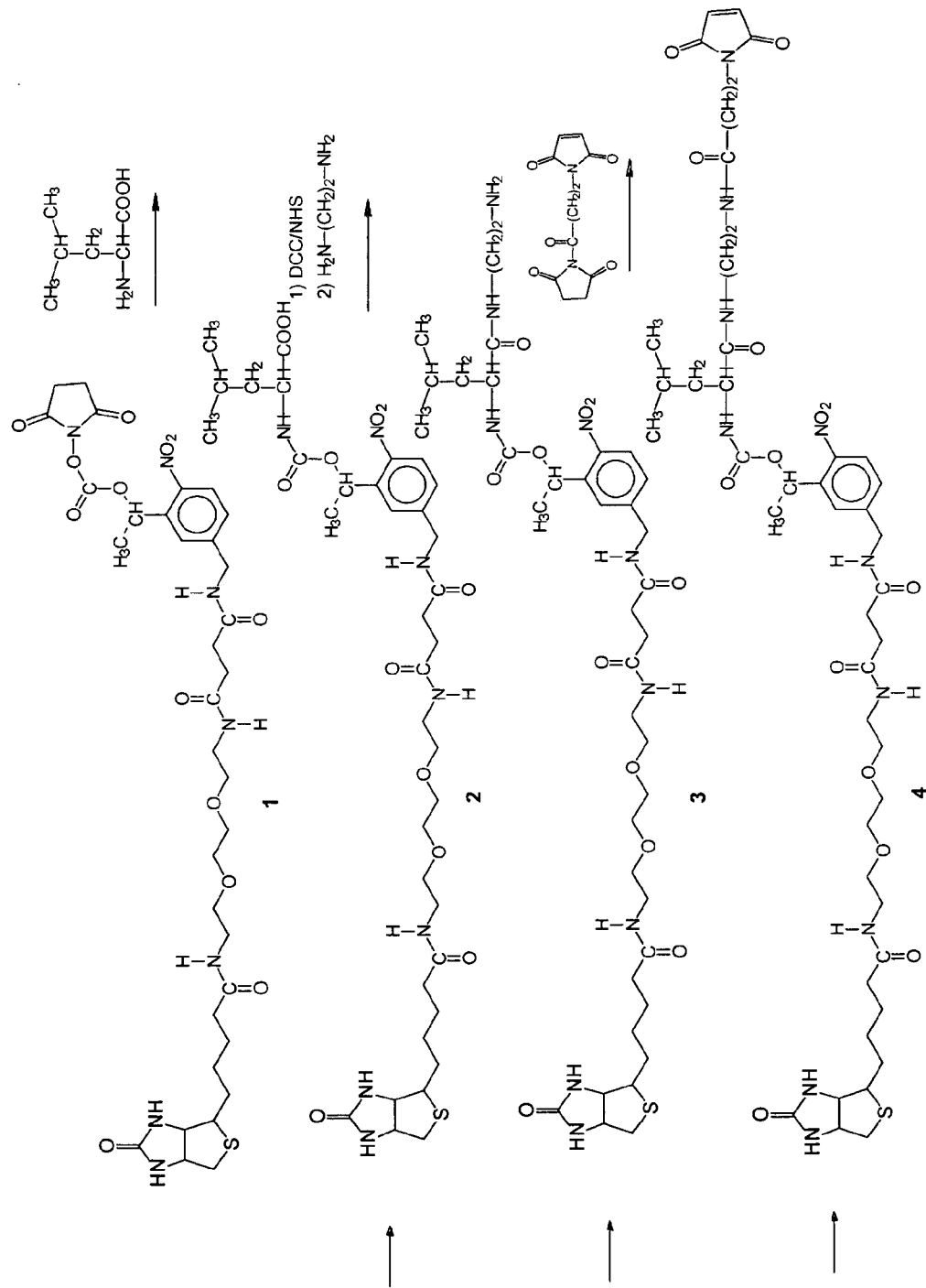
FIG. 14C shows a diagram depicting steps in one embodiment of the synthesis of water soluble PC-Biotin-leucine-maleimide conjugate.

This example shows the synthesis of an α-Fmoc, ε-PC-Biotin-Lys-OH. α-Fmoc, ε-tBoc-Lys-OH (Novabiochem, San Diego, Calif.) (12 mg, 25.16 mmols) (FIG. 14A, compound 1) was treated with 200 µl of a 50% TFA (trifluoroacetic acid) solution in methyl chloride at room temperature for 20 minutes. The volatile components of the mixture were then removed under temperature for 20 minutes. The volatile components of the mixture were then removed under reduced pressure and the mixture was co-evaporated with toluene (3×500 µl). The product was finally freeze-dried from acetonitrile and then dissolved in 200 µl of DMF. To this solution a solution of PC-Biotin (20 mg, 1 eq., 25 µmoles) was added in 200 µl of DMF followed by 2 eqs. Of N,N-diisopropylethylamine (50 µmoles, 9 µl). After stirring for 2 hrs at room temperature, the mixture was acidified to pH=2 by the addition of 1N HCl and extracted with chloroform (5×300 µl). The chloroform layers were combined, dried with $Na_2SO_4$ and evaporated. The solids were dissolved in acetonitrile and freeze-dried and analyzed using HPLC (NovaPak C18 10×100 mm, buffer A: 50 mM triethylammonium acetate, pH 4.5; buffer B: acetonitrile, 0–90% B in A over 45 minutes, flow 1 ml/min) (Run Time (RT)=27.0 min). An example of an immobilized version of this compound is shown in FIG. 14F, compound 7.

Figure 14D:
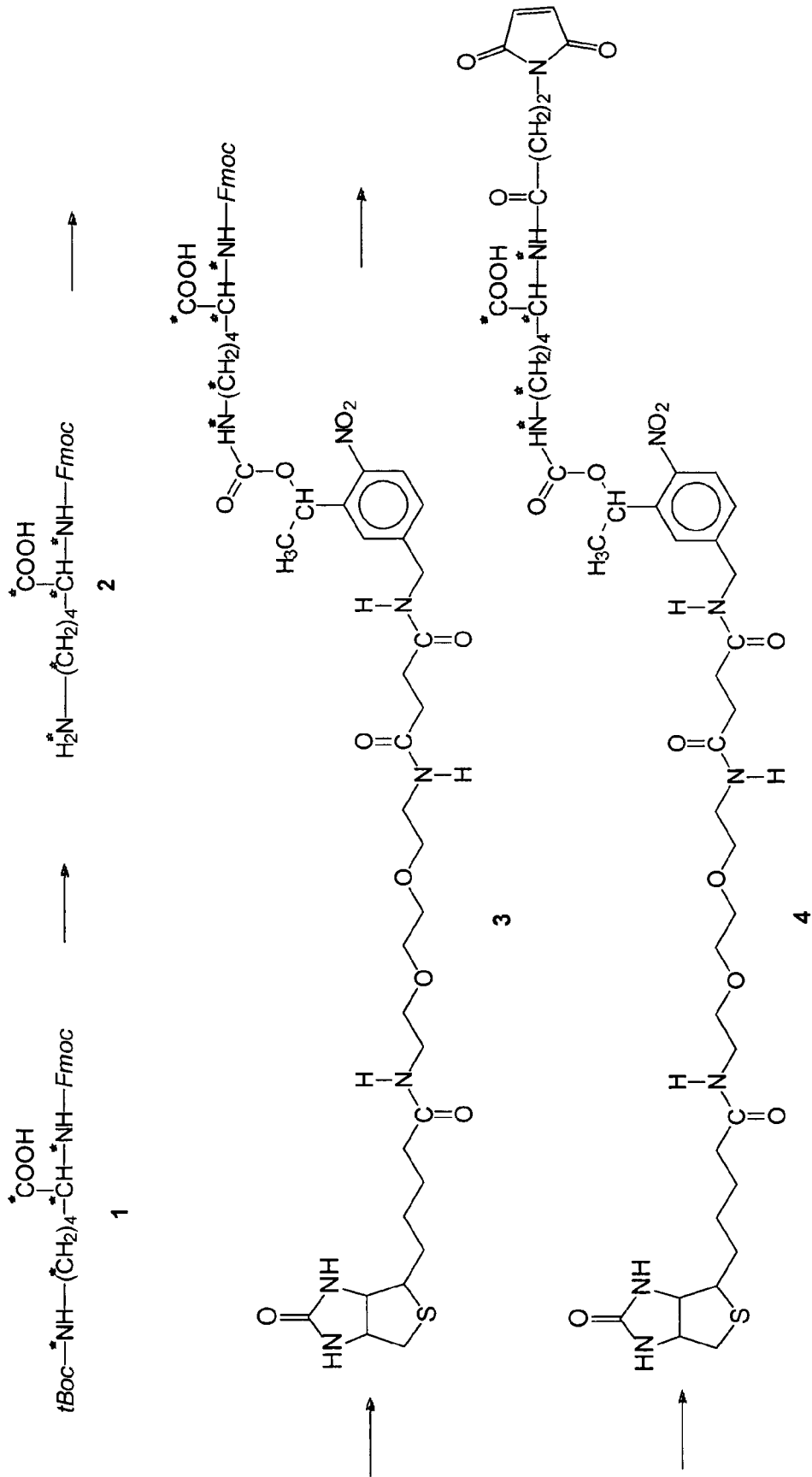
FIG. 14D shows Synthesis of PC-Biotin-lysine (U-$^{13}$C$_6$, $^{15}$N$_2$)-maleimide (α-Maleimidopropyloxy-, ε-PC-Biotin-Lys(U-$^{13}$C$_6$,$^{15}$N$_2$)—OH. The asterisks (*) indicate isotopic atoms. The U indicates that the lysine is uniformly labeled along all the carbon and nitrogen atoms.
Figure 14F:
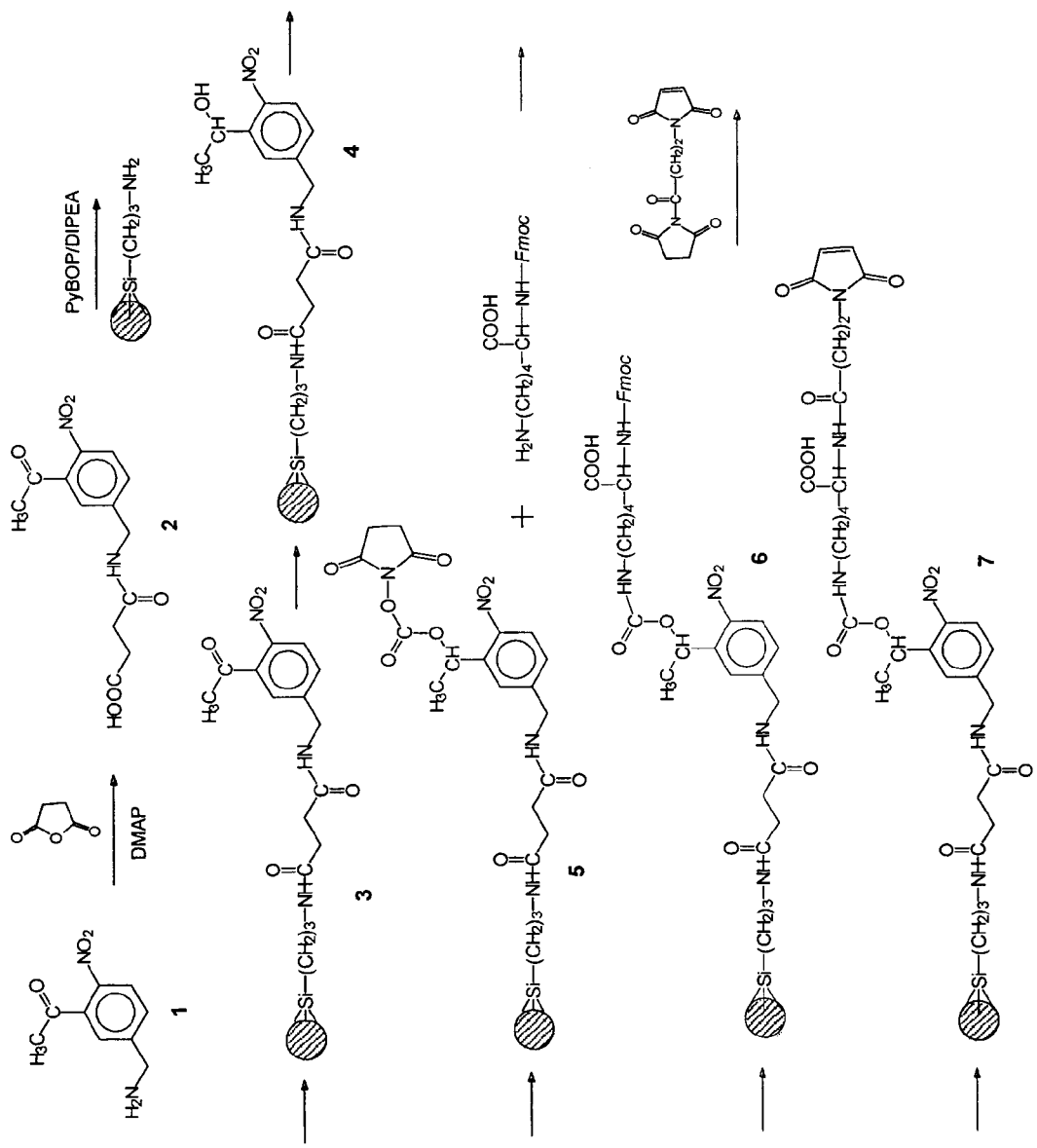
FIG. 14F shows synthesis of immobilized PC-ICAT. Figure depicts steps in their preparation of photocleavable lysine-maleimide conjugated to CPG support.

EXAMPLE 4

α-Fmoc, ε-PC-Biotin-Lys(U-$^{13}C_6$,$^{15}N_2$)—OH (Compound 3, FIG. 14D)

α-Fmoc, ε-tBoc-Lys-OH (U-$^{13}C_6$, 98%; $^{15}N_2$, 98%, Cambridge Isotope Laboratories, Andover, Mass.) (12 mg, 25.16 µmoles) (FIG. 14D, compound 1) was treated with 200 µl of a 50% TFA solution in methylene chloride at room temperature for 20 minutes. The volatile components of the mixture were then removed under reduced pressure, and the mixture was co-evaporated with toluene (3×500 µl). The product was finally freeze-dried from acetonitrile and then dissolved in 200 µl of DMF. To this solution a solution of water soluble PC-Biotin-NHS (Example 2) (20 mg, 1 eq, 25 µmoles) was added in 200 µl of DMF followed by 2 eqs. of N,N'-diisopropylethylamine (50 µmoles, 9 l). After stirring for 2 hrs at room temperature, the mixture was acidified to pH=2 by the addition of 1N HCl and extracted with chloroform (5×300 µl). The chloroform layers were combined, dried with $Na_2SO_4$, and evaporated. The solids were dissolved in acetonitrile and freeze-dried, and analyzed using HPLC (NovaPak C18 10×100 mm, buffer A: 50 mM triethylammonium acetate, pH 4.5; buffer B: acetonitrile, 0–90% B in A over 45 minutes, flow 1 ml/min) (RT=27.0 min.).

EXAMPLE 5

α-Maleimidopropyloxy-NH, ε-PC-Biotin-Lys(U-$^{12}C_6$,$^{14}N_2$)—OH (Compound 4, FIG. 14A)

Figure 15:
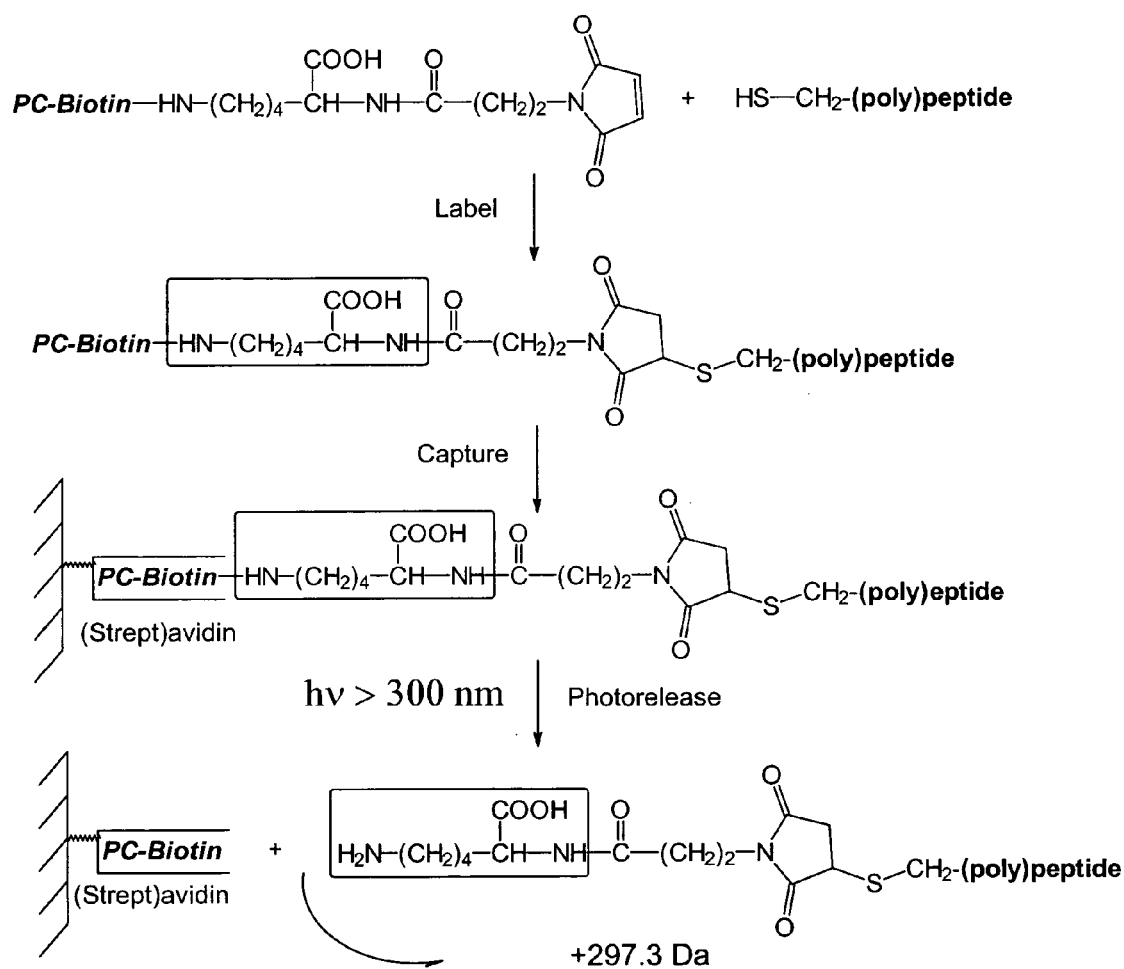
FIG. 15 shows a diagram depicting reaction of the PC-Biotin-lysine-maleimide (α-Maleimidopropyloxy-, ε-PC-Biotin-Lys-OH) conjugate with cysteine containing polypeptide, its affinity capture on streptavidin support and photorelease.
Figure 16:
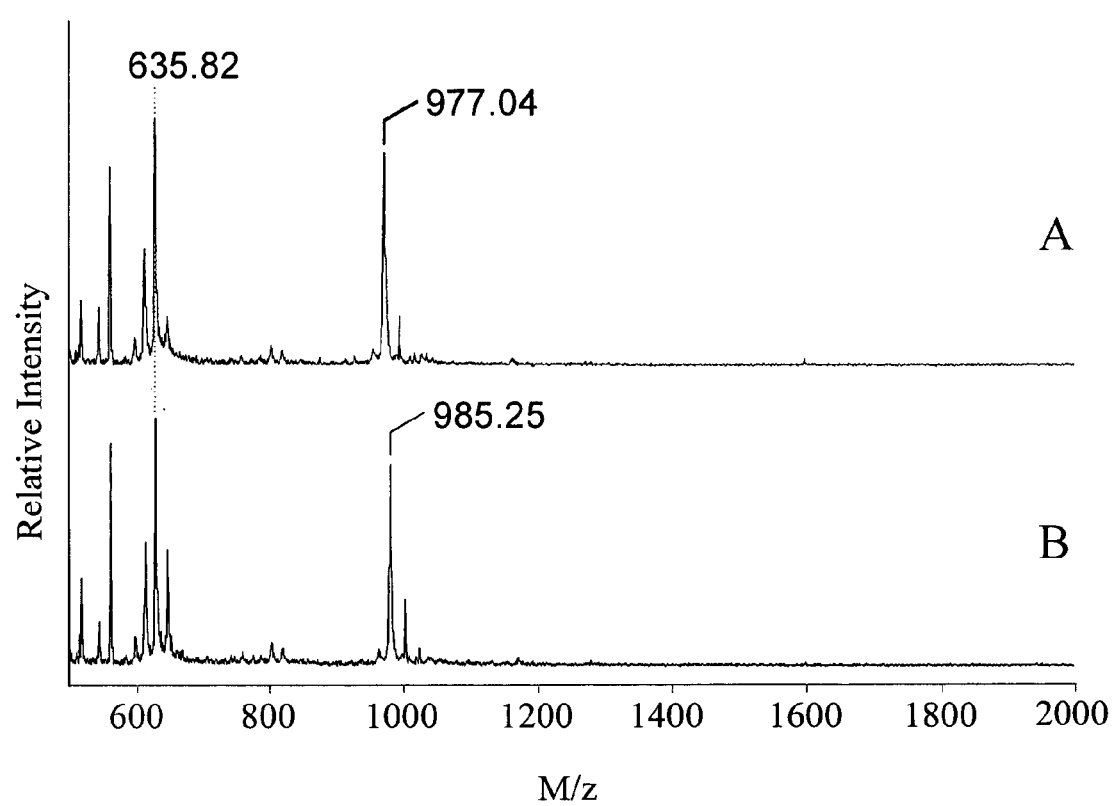
FIG. 16 shows UV-MALDI mass spectrum of the PC-Biotin-lysine-maleimide reagent (α-Maleimidopropyloxy-, ε-PC-Biotin-Lys-OH) (A-light (Lys(U-$^{12}$C$_6$,$^{14}$N$_2$)), B-heavy (Lys(U-$^{13}$C$_6$,$^{15}$N$_2$)).

This example shows the synthesis of α-Maleimidopropyloxy-NH, ε-PC-Biotin-Lys-OH. The α-Fmoc, ε-PC-Biotin-Lys-OH (12 µmoles) was dissolved in 20% piperinine/DMF (600 µl) incubated for 1 hr at room temperature and precipitated to 8 ml of diethyl ether. The precipitate was recovered by centrifugation, redissolved in 200 µl of DMF and reprecipitated to cold diethyl ether (4 ml). Precipitate was dissolved in acetonitrile (500 µl) and freeze-dried. When analyzed by HPLC the α-NH$_2$, ε-PC-Biotin-Lys-OH was characterized by the retention time of 19.6 minutes.

α-NH$_2$, ε-PC-Biotin-Lys-OH (4.5 mg, 6.1 µmoles) was dissolved in 70 µl of PBS (pH 7.4) and to this solution 40 µl of DMF was added followed by a solution of N-β-Maleimidopropyloxy-succinimide (BMPS, Pierce Chemical Co., Rockford, Ill.) (20 µl, 12 µmoles). 15 µl of 1N NaHCO$_3$ was added and the reaction mixture was incubated at room temperature for 2 hrs. The mixture was acidified by the addition of 20 µl of 3M NaOAc, pH 4.5 and purified using HPLC (retention time of the product=21 minutes) to homogeneity. The structure was verified by performing MALDI-MS (FIG. 16A) which gave the expected peak corresponding to the molecular ion of the compound 4 (977.94) as well as the signal resulting from the UV-MALDI induced photocleavage of the compound 4 (636.66). The isolation of this compound is shown diagrammatically in FIG. 15.

EXAMPLE 6

α-Maleimidopropyloxy-NH, ε-PC-Biotin-Lys(U-$^{13}C_6$,$^{15}N_2$)—OH (Compound 4, FIG. 14D)

The α-Fmoc, ε-PC-Biotin-Lys(U-$^{13}C_6$,$^{15}N_2$)—OH (12 µmoles) was dissolved in 20% piperidine/DMF (600 µl) incubated for 1 hr at room temperature, and precipitated to 8 ml of diethyl ether. The precipitate was recovered by centrifugation, re-dissolved in 200 µl of DMF and re-precipitated to cold diethyl ether (4 ml). Precipitate was dissolved in acetonitrile (500 l) and freeze-dried. When analyzed by HPLC the α-NH$_2$, ε-PC-Biotin-Lys(U-$^{13}C_6$,$^{15}N_2$)—OH is characterized by the retention time of 19.6 minutes.

α-NH$_2$, ε-PC-Biotin-Lys(U-$^{13}C_6$,$^{15}N_2$)—OH (4.5 mg, 6.1 µmoles) was dissolved in 70 µl of PBS (pH 7.4) and to this solution 40 µl of DMF was added followed by a solution of N-β-Maleimidopropyloxy-succinimide (BMPS, Pierce Chemical Co., Rockford, Ill.) (20 µl, 12 µmoles). 15 µl of 1N NaHCO$_3$ was added and the reaction mixture was incubated at room temperature for 2 hrs. The mixture was acidified by the addition of 20 µl 3M NaOAc, pH 4.5 and purified using HPLC (retention time of the product=21 minutes.) to homogeneity. The structure was verified by performing MALDI-MS (FIG. 16B) which gave the expected peak corresponding to the molecular ion of the compound 4 (985.25) as well as the signal resulting from the UV-MALDI induced photocleavage of the compound 4 (636.66).

EXAMPLE 7

Evaluation of the α-Maleimidopropyloxy-NH, ε-PC-Biotin-Lys(U-$^{12}C_6$,$^{14}N_2$)—OH and α-Maleimidopropyloxy-NH, ε-PC-Biotin-Lys(U-$^{13}C_6$,$^{15}N_2$)

This example evaluates the α-Maleimidopropyloxy-NH, ε-PC-Biotin-Lys-OH PC-reagents ICAT in its light and heavy version. The usefulness of the PC-ICAT-maleimide reagent (structure shown in FIG. 14E, PC-ICAT#1) was tested using model peptides shown below (SEQ ID NOS: 1 & 2).

Peptide 1=SV 40 Nuclear Transport Signal Peptide Analog (Bachem, Torrance, Calif.), sequence:

```
H2N-CGYGPLLLRLVGG-OH.         (SEQ ID NO.:1)
```

Peptide 2=HIV gs120 Antigenic Peptide (Bache, Torrance, Calif.), sequence:

```
H2N-CGKIEPLGVAPTKAKRRVVQREKR-OH.    (SEQ ID NO.:2)
```

Both these peptides contain a single reactive cysteine that can be derivatized with the PC-ICAT-maleimide reagent. To evaluate the performance of the PC-ICAT reagent reactions with both peptides, analogs were prepared and analyzed both in solution and after specific capture on neutravidin-agarose beads. Stock solutions of both peptides and the reagent (α-Maleimidopropyloxy-NH, ε-PC-Biotin-Lys-OH) were prepared at a concentration of 1 mg/ml in 50% acetonitrile. 2 μl of the peptide stock (7.2–14.4 nmoles) was added to 1 μl of the reagent stock (~10 nmoles) followed by 1 μl of PBS. The reactions were incubated at room temperature for 2 hrs, diluted 1,000-fold and analyzed by MALDI-MS using ((α-cyano-4-hydroxycinnamic acid (CHCA) as a matrix (dried droplet ample preparation). The matrix was dissolved in 50% acetonitrile, 1% TFA at a concentration of 10 mg/ml and 1 μl spotter on the stainless steel MALDI target followed by 1 μl of the sample. The samples were analyzed using Voyager DE mass spectrometer (PerSeptive Biosystems, Framingham, Mass.).

Figure 17:
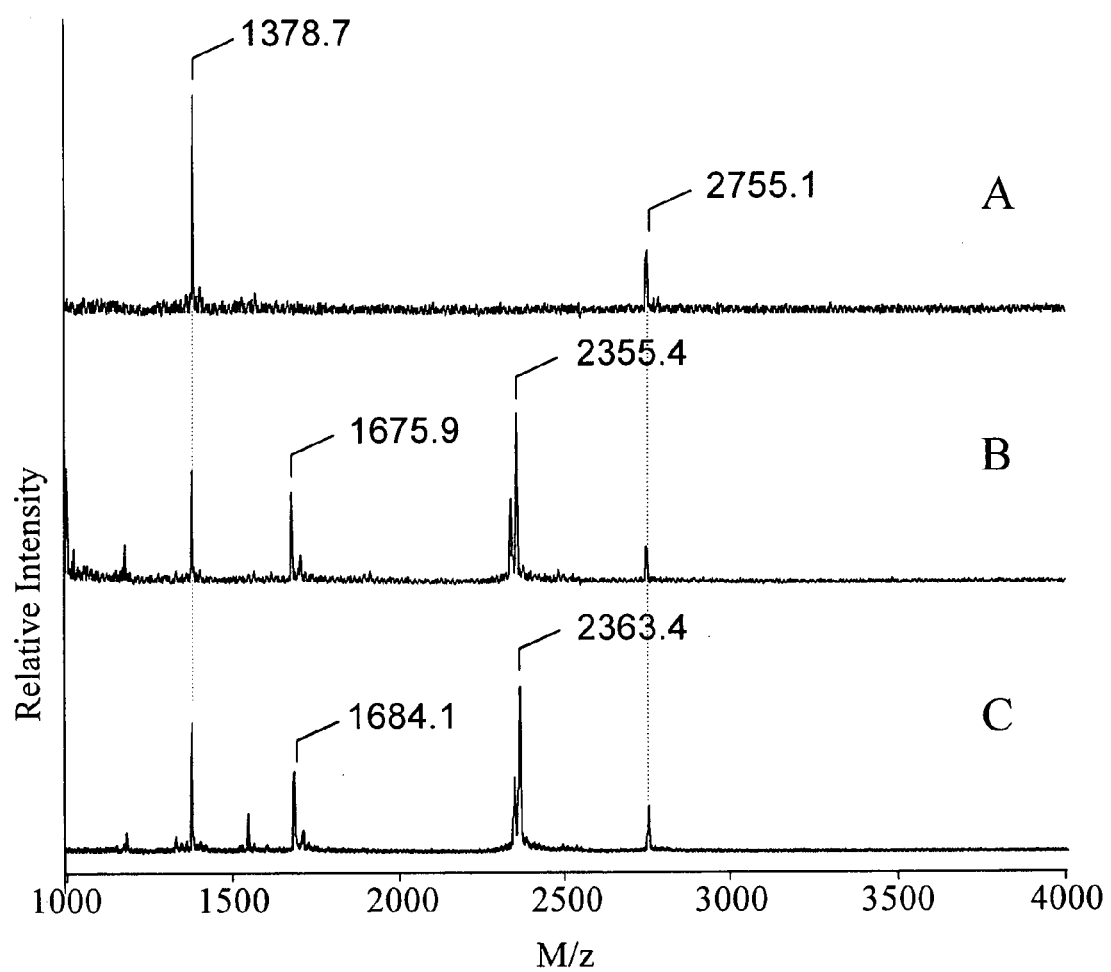
FIG. 17 shows UV-MALDI mass spectrum of the SV40 peptide analog (A), its reaction with PC-Biotin-lysine-maleimide PC-ICAT reagents (α-Maleimidopropyloxy-, ε-PC-Biotin-Lys-OH) (B-light (Lys(U-$^{12}$C$_6$,$^{14}$N$_2$)) and C-heavy (Lys(U-$^{13}$C$_6$,$^{15}$N$_2$)).

FIG. 17A shows the mass spectrum of the SV40 peptide analog and FIGS. 17B and 17C show the mass spectra of the reaction products with light PC-ICAT-maleimide and heavy PC-ICAT maleimide, respectively. In the spectrum of the SV40 peptide analog a peak at 1378.7 Da is observed, which is attributed to the monoprotonated molecular ion. In addition, a peak at 2755.1 Da is observed which is most likely due to the formation of the gas phase dimer by the peptide. Upon reaction with the PC-ICAT maleimide, two new peaks are observed at 2355.4 Da (light, FIG. 17B) or 2363.4 (heavy, FIG. 17C). The intensity of the peak at 1378.7 Da decreases significantly at the same time. Partial photocleavage products produced by the nitrogen laser of the MS-MALDI instrument are also visible at 1675.9 Da (light, FIG. 17B) or at 1684.1 Da (heavy, FIG. 17C).

Figure 18:
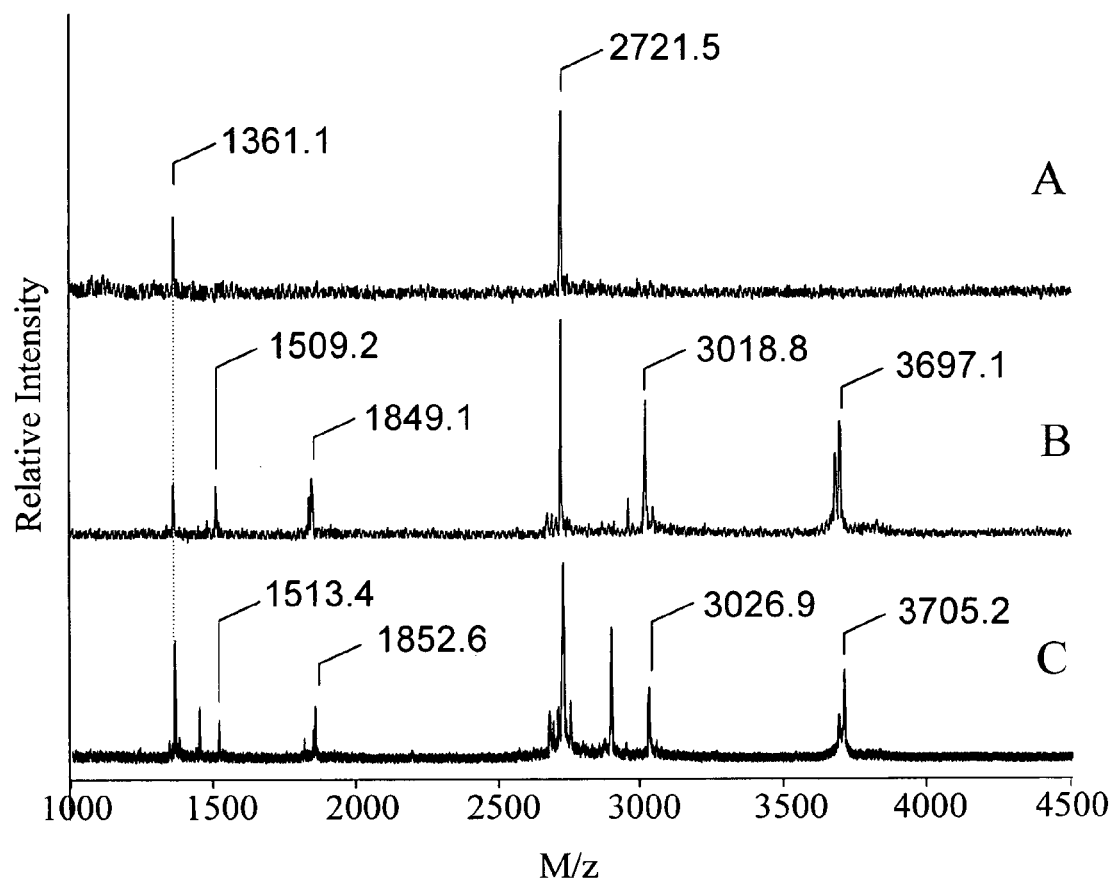
FIG. 18 shows UV-MALDI mass spectrum of the gp120 peptide analog (A), its reaction with PC-Biotin-lysine-maleimide PC-ICAT reagents (α-Maleimidopropyloxy-, ε-PC-Biotin-Lys-OH) (B-light (Lys(U-$^{12}$C$_6$,$^{14}$N$_2$)) and C-heavy (Lys(U-$^{13}$C$_6$,$^{15}$N$_2$)).

Similarly to the SV40 peptide analog, the usefulness of the PC-ICAT maleimide reagent was also tested by reacting it with another model peptide, gp120 peptide analog, containing single cysteine residue. The spectrum of the gp120 peptide analog is shown in FIG. 18A. A major peak at 2721.5 Da is observed in this spectrum, which can be attributed to the monoprotonated molecular ion. In addition, a peak at 1361.1 Da is observed in this spectrum, which can be assigned to the doubly-protonated molecular ion of the parent peptide. Upon reaction with PC-ICAT-maleimide reagent a peak at 3697.1 Da (light, FIG. 18B) or at 3705.2 Da (heavy, FIG. 18C) which can be assigned to the monoprotonated molecular ion of the reaction product. In addition peaks attributable to partial photocleavage by MALDI laser beam are observed at 3018.8 Da (light, FIG. 18B) or 3026.9 Da (heavy, FIG. 18C). A series of doubly charged ions of the reaction product and photocleavage product is also observed at lower mass range (light, FIG. 18B, 1849.1 Da; 1509.2 Da;), (heavy, FIG. 18C, 1852.6, 1513.4 Da).

As expected, in both cases the thioether adduct of the reagent with the peptide was formed (mass of the peptide increases by ~976 (light, FIGS. 17B, 18B) or 984 (heavy, FIGS. 17C, 18C) Da. In addition, a presence of cleavage product was also observed (mass of the peptide increased by ~297 (light, FIGS. 17B, 18B) or ~305 (heavy, FIGS. 17C, 18C) Da) caused by UV-laser. FIG. 20 shows calculated and measured masses for these reactions in solution as well as desorbed from neutravidin agarose beads.

Figure 21:
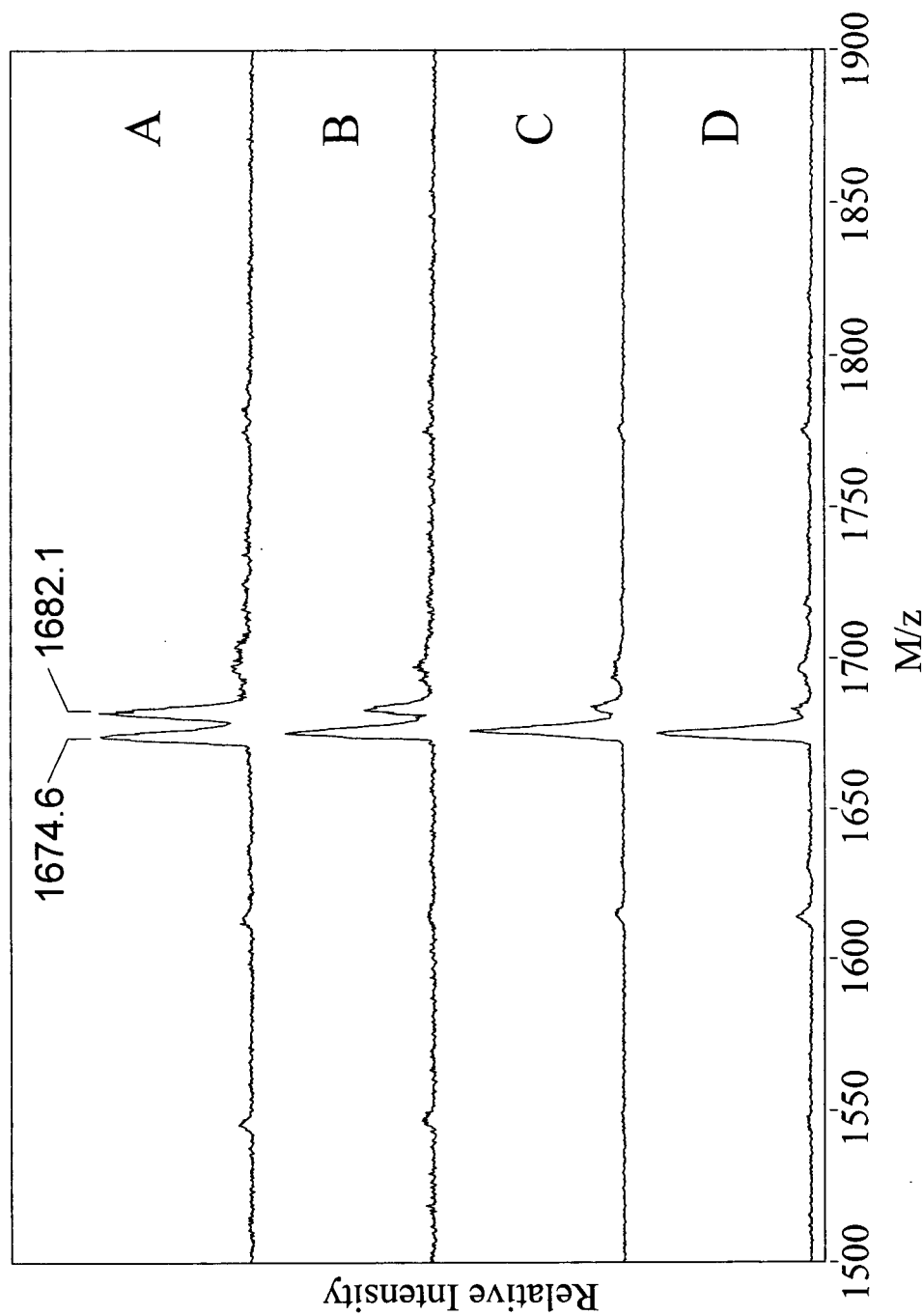
FIG. 21 shows MALDI-TOF mass spectra obtained from SV40 peptide analog modified with light α-Maleimidopropyloxy-, ε-PC-Biotin-Lys (U-$^{12}$C$_6$,$^{14}$N$_2$)—OH and heavy α-Maleimidopropyloxy-, ε-PC-Biotin-Lys(U-$^{13}$C$_6$,$^{15}$N$_2$)—OH PC-ICAT reagents, mixed at various ratios, captured on streptavidin agarose beads, photoreleased and analyzed by MALDI-MS. The following light/heavy ratios were used: A-1:1, B-2:1, C-5:1, D-10:1.

To evaluate the usefulness of light and heavy PC-ICAT reagents in quantitation, experiments using mass spectrometry the separate reactions of the SV40 peptide analog with light and heavy PC-ICAT reagents were set up. The reactions were then mixed at various proportions, captured on neutravidin beads, photoreleased and analyzed using MALDI-MS. The results of these experiments are shown in FIG. 21. As can be seen two peaks were observed, separated by ~8 Da, indicating that these peaks originated from PC-ICAT modification. In addition, the peak areas were proportional to the ratio the reactions were mixed at initially, confirming the usefulness of this approach for the relative abundance determination.

Figure 22:
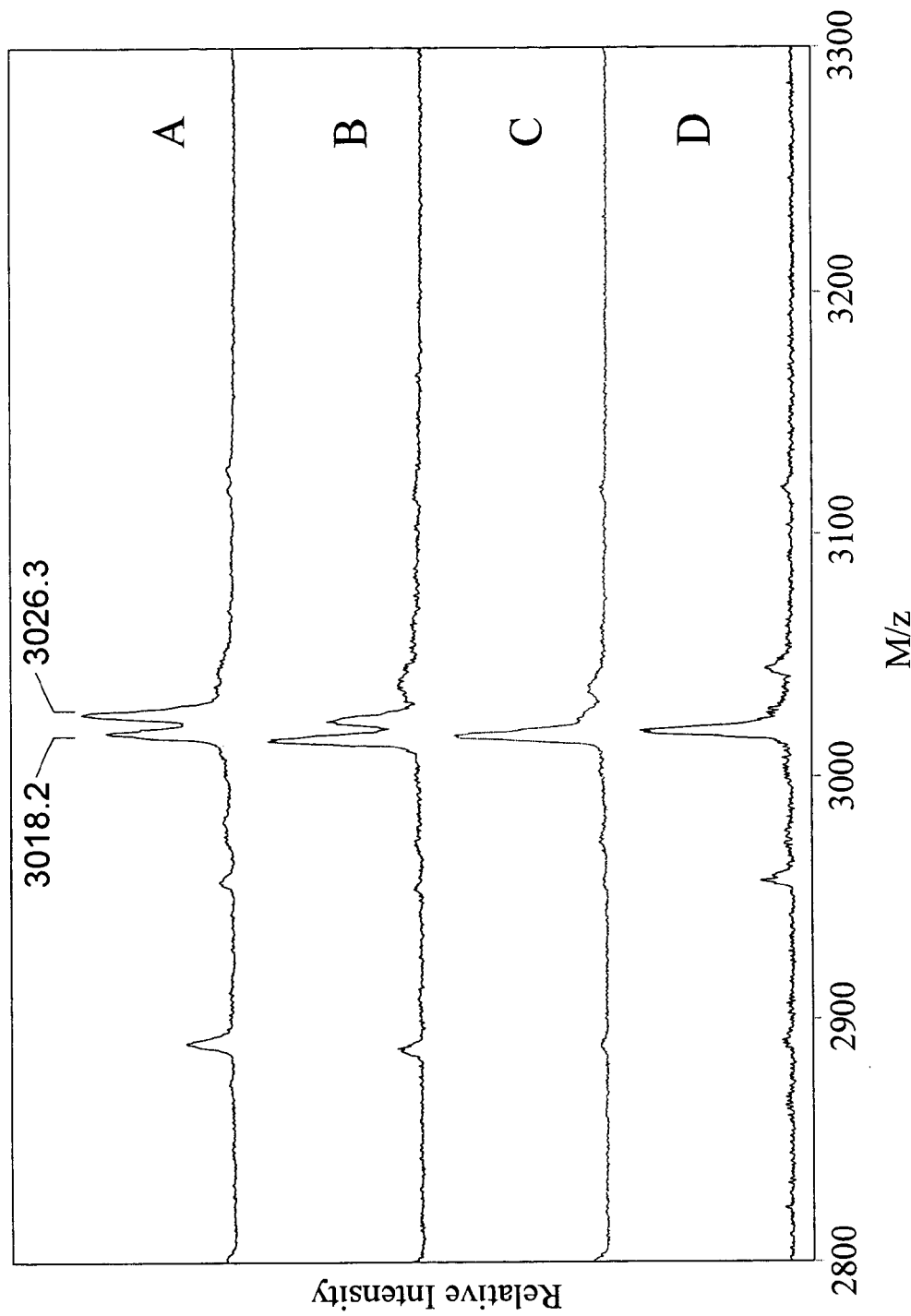
FIG. 22 shows MALDI-TOF mass spectra obtained from gp120 peptide analog modified with light α-Maleimidopropyloxy-, ε-PC-Biotin-Lys(U-$^{12}$C$_6$,$^{14}$N$_2$)—OH and heavy α-Maleimidopropyloxy-, ε-PC-Biotin-Lys(U-$^{13}$C$_6$,$^{15}$N$_2$)—OH PC-ICAT reagents, mixed at various ratios, captured on streptavidin agarose beads, photoreleased and analyzed by MALDI-MS. The following light/heavy ratios were used: A-1:1, B-2:1, C-5:1, D-10:1.

The usefulness the light and heavy PC-ICAT reagents was also tested in reactions with the gp120 peptide analog. Two separate reactions containing both light and heavy PC-ICAT reagents were set up, reactions mixed at various proportions, captured on neutravidin beads, photoreleased and analyzed using MALDI-MS. The results of these experiments are shown in FIG. 22. As can be seen two peaks were observed, separated by ~8 Da, indicating that these peaks originated from PC-ICAT modification. In addition, the peak areas were proportional to the ratio the reactions were mixed at initially, confirming the usefulness of this approach for the relative abundance determination.

EXAMPLE 8

Capture of the Reaction Products on the Neutravidin and Photorelease

Figure 19:
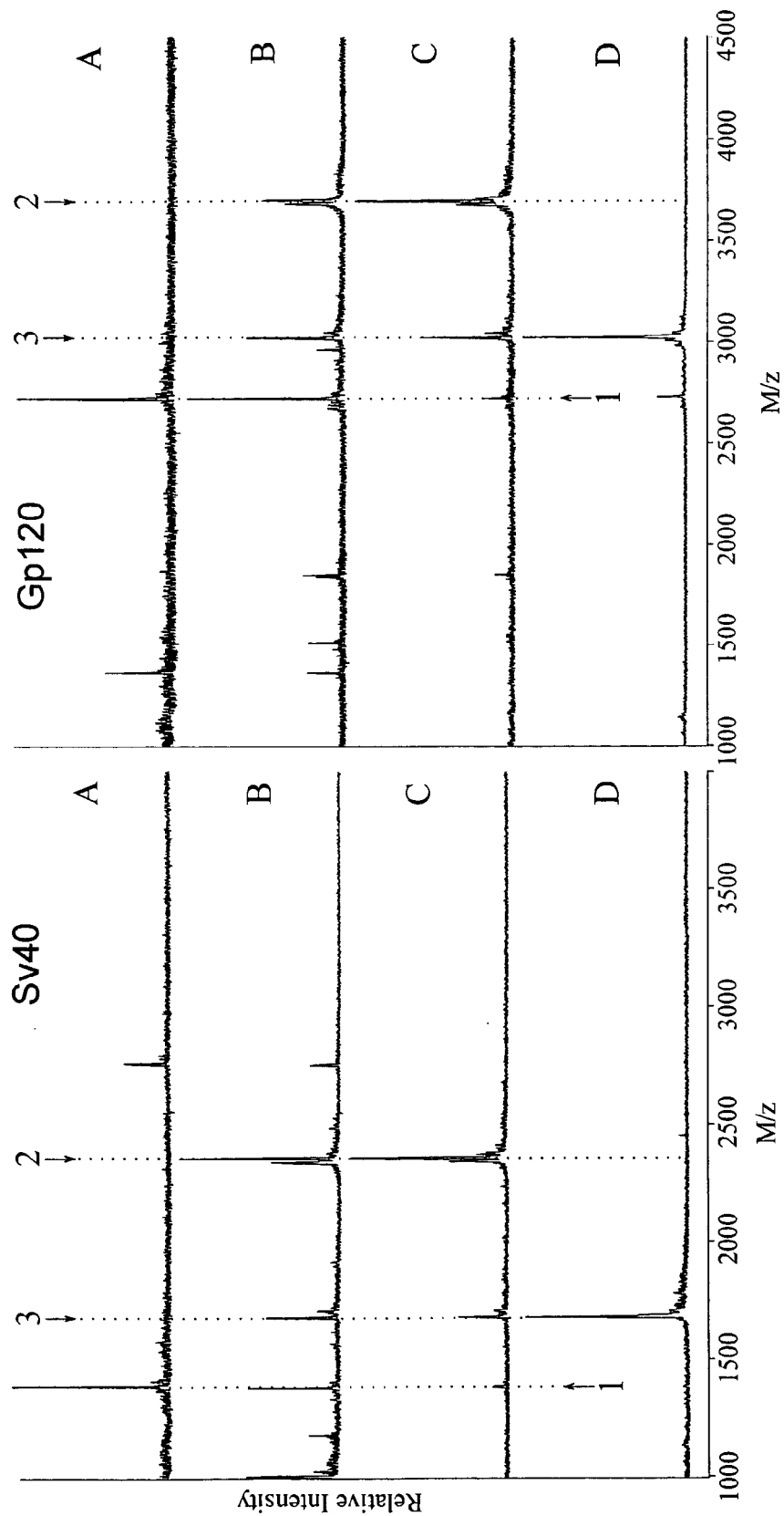
FIG. 19 shows MALDI-TOF mass spectra for two model peptides, SV40 (left panel) and gp120 (right panel) are shown: A) peptide before modification, B) peptide+ (α-Maleimidopropyloxy-, ε-PC-Biotin-Lys(U-$^{12}$C$_6$,$^{14}$N$_2$)—OH (light) mixture, C) reaction mixture captured on streptavidin-agarose beads-direct desorption from beads, D) PC-Biotin-lysine-maleimide (α-Maleimidopropyloxy-, ε-PC-Biotin-Lys(U-$^{12}$C$_6$,$^{14}$N$_2$)—OH (light) modified peptide after photorelease from streptavidin beads. Peaks corresponding to unmodified peptide (1), peptide modified with PC-Biotin-lysine-maleimide (light) reagent (2), and photocleavage product-mass tagged peptide (3) with mass increased by 297.3 Da.

This example demonstrates the capture of substrate with the compounds of the present invention and their subsequent photorelease and characterization. Stock solutions of both peptides (SV40 and gp120 analogs, see Example 7) and the light (Lys-U-$^{12}C_6$,$^{14}N_2$) and heavy (Lys-U-$^{13}C_6$,$^{15}N_2$) reagent (α-Maleimidopropyloxy-NH, ε-PC-Biotin-Lys-OH) were prepared at a concentration of 1 mg/ml in 50% acetonitrile. 2 μl of the peptide stock (7.2–14.4 nmoles) was added to 1 μl of the reagent stock (~10 nmoles) followed by 1 μl of PBS. The reactions were incubated at room temperature for 2 hrs and added to 50 μl of Neutravidin suspension (Pierce Chemical Co., Rockford, Ill.) in PBS, incubated for 1 hr with gentle shaking and the mixture transferred to the filter tip, washed with 3×100 μl of PBS and 3×10 μl of 50 mM NH$_4$OAc. The beads were resuspended in 50 mM NH$_4$OAc and aliquots (1 μl) were spotted directly on the MALDI target and mixed with the CHCA matrix solution. The remaining suspension was subjected to irradiation with near UV light for 15 minutes (see, FIGS. 19A–D) and the aliquots of the supernatant were analyzed by MALDI-MS. The results of the experiments for reactions with light version of the reagent are presented in FIG. 19 and Table 5.

|  | Mass calculated (MH)+ | Mass measured |
|---|---|---|
| Reagent PC-Bio-Lys-Mal | 976.41 (uncleaved); 635.28 (cleaved) | 977.94; 636.66 |
| SV-40 peptide | 1378.69; 2755.38 (homodimer) | 2754.06 (homodimer); 1378.74; |
| SV-40 peptide + PC-Bio-Lys-Mal | 2355.1 (uncleaved); 1676.0 (cleaved) | 2753.53 (homodimer) 2354.36; 1675.98; 1378.36 |

-continued

| | Mass calculated (MH)+ | Mass measured |
|---|---|---|
| HIV gp120 peptide | 2721.30 | 2720.52; 1361.14 (MH$_2$)+ |
| HIV gp120 peptide + PC-Bio-Lys-Mal | 3697.71 (uncleaved) 3018.61 (cleaved) | 3697.09; 3018.82; 2721.45; 1849.13; 1511.18; 1361.88 (MH$_2$)+ |

As expected, in the case of neutravidin beads analysis, the peaks assigned to the peptide modified with the reagent (+976 Da) and cleavage product (+297.3 Da) were observed. In the case of off-line photocleavage only the cleavage product (+297.3 Da) was observed in the spectrum. See, Table 6.

| | Mass calculated (MH)+ | Mass measured |
|---|---|---|
| SV-40 peptide + PC-Bio-Lys-Mal | 2355.1 (uncleaved); 1676.0 (cleaved) | A) On beads: 2354.69; 1676.33; B) Cleaved/ supernatant: 1677.07 |
| HIV gp120 peptide + PC-Bio-Lys-Mal | 3697.71 (uncleaved) 3018.61 (cleaved) | A) On beads: 3695.26; 3016.66; B) Cleaved/ supernatant: 3015.47 |

EXAMPLE 9

Peptide Ratio Determination Using PC-ICAT Reagents

Two separate reactions with model peptide SV40 (or gp120) were prepared with either light or heavy versions of the PC-ICAT reagent as described in Example 7. The resulting light and heavy PC-ICAT reaction mixtures were then mixed at various light:heavy ratios (i.e., 1:1, 1:2, 1:5, 1:10) and aliquots irradiated with near UV light and analyzed by MALDI-MS. The MALDI-MS spectra of the peptides modified with light and heavy PC-ICAT reagents mixed at various ratios are shown in FIGS. 21 and 22. Peaks resulting from the modification with light and heavy PC-ICAT reagent separated by 8 Da were identified and the integrated intensity of these peaks used to calculate the input ratio of the peptides in two samples. The ratios calculated using PC-ICAT reagent isotope labeling for two model peptides are shown in FIG. 25.

EXAMPLE 10

Example of PC-ICAT Synthesis Utilizing Leucine

The synthesis of the photocleavable isotope coded affinity tag reagent based on leucine is presented in FIG. 14C. It is similar to the PC-ICAT synthesis utilizing lysine (FIG. 14A) and valine (FIG. 14B). Briefly, free valine is dissolved in a mixture of acetonitrile-water in the presence of 2 equivalents of triethylamine. A solution of PC-Biotin-NHS (1) in DMF is added slowly during 15 minutes with stirring. The reaction is stirred at room temperature for additional 1 hr and then acidified to pH=6.0 with 1N HCl, evaporated to dryness under reduced pressure and product purified on silica gel using a step gradient of methanol in chloroform. PC-Biotin-Valine conjugate (2) is then converted into active NHS ester by standard DCC mediated coupling with N-hydroxysiccin- imide and the active ester formed coupled with excess ethylenediamine to give intermediate (3). The intermediete 3 is then converted into the sulfhydryl reactive target compound (4) by reacting it with bifunctional crosslinker N-b-Maleimidopropyloxy-succinimide (BMPS, Pierce Chemical Co., Rockford, Ill.).

Zhou, et al., (Nature Biotech. 19:512 (2002), described the synthesis of the immobilized photocleavable ICAT reagent based on the use of 4-[4-(Fmoc-amino)-2-methoxy-5-nitrophenoxy)butanoic acid. The use of the 2-nitrobenzyl group with electron-donating substituents is known to decrease the rate of the photocleavage reaction (Hasan, A., et al., Tetrahedron 53:4247–4264, 1997). This necessitated very long irradiation times to achieve the photocleavage (1 hr with 100 W electrical power light source). The linkers used in the present invention are known to exhibit very fast and efficient photocleavage (Milburn, T., et al., Biochemistry, 28(1):49–55, 1989; Walker, et al., J. Am. Chem. Soc., 110:7170–7177, 1988) with exposure times as short as 5 minutes and the source with electrical power of only 30 W giving nearly quantitative photocleavage (Olejnik, J., et. al., Nucleic Acids Res. 24(2):361–366, 1996). In addition, the linker design described by Zhou, et al., (Nature Biotech. 19:512, 2002) causes the peptide fragment to be released as primary amide, whereas the linker of present invention generates primary amines, which are known to be photocleaved easier and in addition act as a "charge tag" for mass spectrometry applications.

EXAMPLE 11

Solid Phase PC-ICAT Synthesis Using 1-(2-nitrophenyl) ethyl Group.

In addition to PC-Biotin based reagents, which rely on the interaction between biotin and streptavidin for specific capture of modified peptides, this invention also contemplates photocleavable ICAT reagents that do not rely on biotin-streptavidin interaction. This can be achieved, for example, by linking photocleavable linker directly to suitable solid support. The scheme showing the synthesis of on such PC-ICAT reagent is shown in FIG. 14F. In this example, controlled pore glass (CPG) which has been modified with aminopropyl(triethoxysilane) or other similar aminosilane reagent. 5-aminomethyl-2-nittroacetophenone (1) is reacted with succinic anhydride in the presence of 2,6-dimethylami-nopyridine (DMAP) to give 5-succinyloamidomethyl-2-nitroacetophenone (2). This intermediate is coupled to aminopropyl-glass beads (Sigma) using PyBOP/DIPEA activation procedure to give intermediate (3). The beads with coupled 5-succinyloamidomethyl-2-nitroacetophenone are then resuspended in ethanol and excess of sodium borohydride is added and the mixture stirred for 1 hr at room temperature. The beads are washed with ethanol and dried (intermediate 4). The resulting secondary 1-(2-nitrophenyl)-ethyl group is then converted into active NHS carbonate by reacting with excess of N,N-disuccinimidyl carbonate to give the intermediate (5). This intermediate was then coupled with excess of ε-NH$_2$,-α-Fmoc-Lys-OH in DMF using N,N-diisopropylethylamine as base to give the intermediate (6). The Fmoc group has been removed by using 20% piperidine in DMF and the support was then converted into the target formula (7) by reacting with bifunctional crosslinker N-β-Maleimidopropyloxy-succinimide (BMPS, Pierce Chemical Co., Rockford, Ill.).

EXAMPLE 12

Reaction of α-Maleimidopropyloxy-NH, ε-PC-Biotin-Lys-OH (Compound 4, FIG. 14A) with Bovine α-lactalbumin The PC-ICAT reagents of the present invention are also useful for determination of protein abundance. To demonstrate the usefulness of these reagents for protein abundance determination, two equal size samples of lactalbumin protein were separately derivatized with "light" and "heavy" versions of the PC-ICAT maleimide reagent. They were then combined and subjected to proteolysis, captured on immobilized neutravidin support and finally photoreleased into aqueous medium. Samples were then premixed with MALDI matrix and analyzed.

Figure 23A:
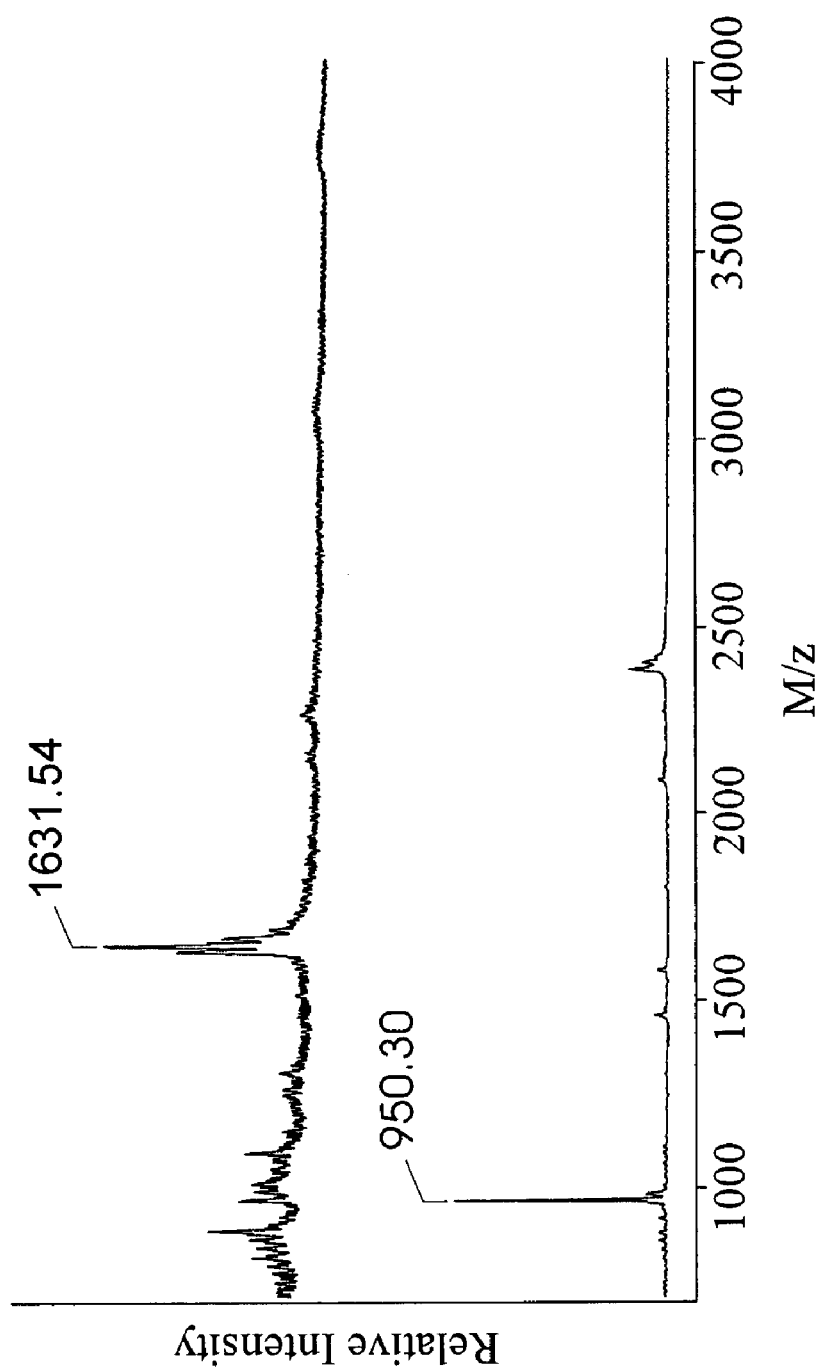
FIG. 23A shows MALDI-TOF mass spectra obtained from sample of bovine lactalbumin modified with light (Lys(U-$^{12}$C$_6$,$^{14}$N$_2$) version of PC-ICAT reagent, digested with trypsin and captured on neutravidin-agarose beads. Top spectrum is the spectrum obtained by desorption from beads, bottom obtained from the supernatant after irradiation with near UV light.

In greater detail, to a solution of bovine lactalbumin (1 mg, 70 nmol) in 100 ul of PBS buffer 3 ul of a 0.5 M solution of tricarboethoxyphosphine (TCEP) was added and the solution was incubated at RT for 1 hour. The solution was then loaded onto the NAP-5 gel filtration column (Amersham-Pharmacia) and eluted with 1 ml of PBS buffer. 10 μl aliquot of reduced lactalbumin (10 μg, 0.7 nmoles) was then withdrawn and a solution of α-Maleimidopropyloxy-NH, ε-PC-Biotin-Lys-OH (compound 4, FIG. 14A; 5 nmoles) in 5 μl of PBS was added. The mixture was incubated at room temperature for 1 hr and then 50 μl of 100 mM Tris-HCl, pH=8.0 was added followed by a solution of sequencing grade trypsin (Roche Molecular Biochemicals, 2 μg in 20 μl). After 2 hrs at 37° C., the reaction mixture was diluted with PBS to 200 μl and mixed with 50 μl of Neutravidin-agarose suspension (Pierce Chemical Co.,). The suspension was incubated at room temperature for 1 hr, washed with 1M NaCl (3×200 μl), PBS (3×200 μl) and 50 mM NH$_4$OAc, pH 5.0 (3×200 μl). The Neutravidin beads were premixed with the CHCA matrix and analyzed using MALDI-MS. The spectrum obtained by direct desorption from beads is shown in FIG. 23A (top). The beads were also resuspended in 50 mM NH4OAc, pH 5.0 and subjected to 10 minutes of irradiation with near UV light (Blak Ray XX-15, UVP Inc.) and the supernatant was analyzed using MALDI-MS. The spectrum of the irradiated supernatant is shown in FIG. 23A (bottom). Table below summarizes masses calculated and observed for the peptide CEVFR containing single cysteine and being a result of proteolytic digestion of lactalbumin. This peptide with a mass of 653.30 upon the reaction with the PC-ICAT reagent α-Maleimidopropyloxy-NH, ε-PC-Biotin-Lys-OH generates a product with a calculated mass of 1631.54 and upon photocleavage another product with a calculated mass of 950.30. The masses observed in the mass spectra agree well with those predicted.

| Mass measured | Mass calculated (MH)+ |
|---|---|
| A) On beads: 1634.89; | A) Uncleaved 1631.54 |
| B) Cleaved/supernatant: 950.41 | B) Cleaved 950.30 |

Figure 23B:
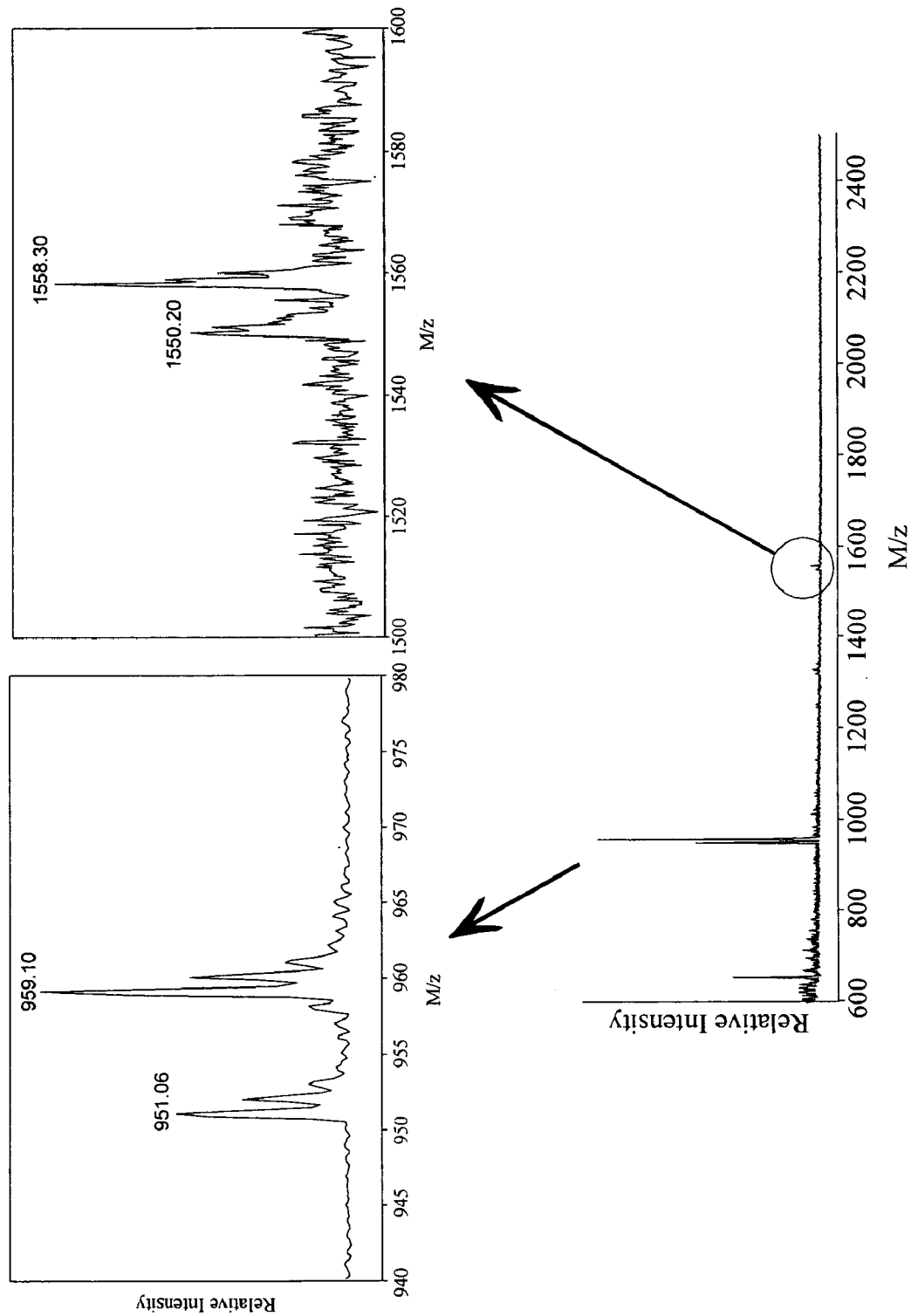
FIG. 23B shows MALDI-TOF mass spectra obtained from sample of bovine lactalbumin modified with light (Lys(U-$^{12}$C$_6$,$^{14}$N$_2$)) and heavy (Lys(U-$^{13}$C$_6$,$^{15}$N$_2$)) versions of PC-ICAT reagent (α-Maleimidopropyloxy-, ε-PC-Biotin-Lys-OH), mixed at 1:1 ratio, digested with trypsin and purified using affinity capture and photorelease from streptavidin agarose. Bottom; spectrum in the full 500–2500 M/z range, top insets showing regions with isotopically labeled peaks separated by 8 Da.

As can be seen in FIG. 23B, the spectra contain two sets of peaks each separated by about 8 Da, indicating that they originated from the modification by the PC-ICAT reagent. The abundance of each protein in the sample can be determined from the ratio of the areas of "light" and "heavy" peaks of any peptide resulting from the digestion and carrying the PC-ICAT modification.

Figure 24:
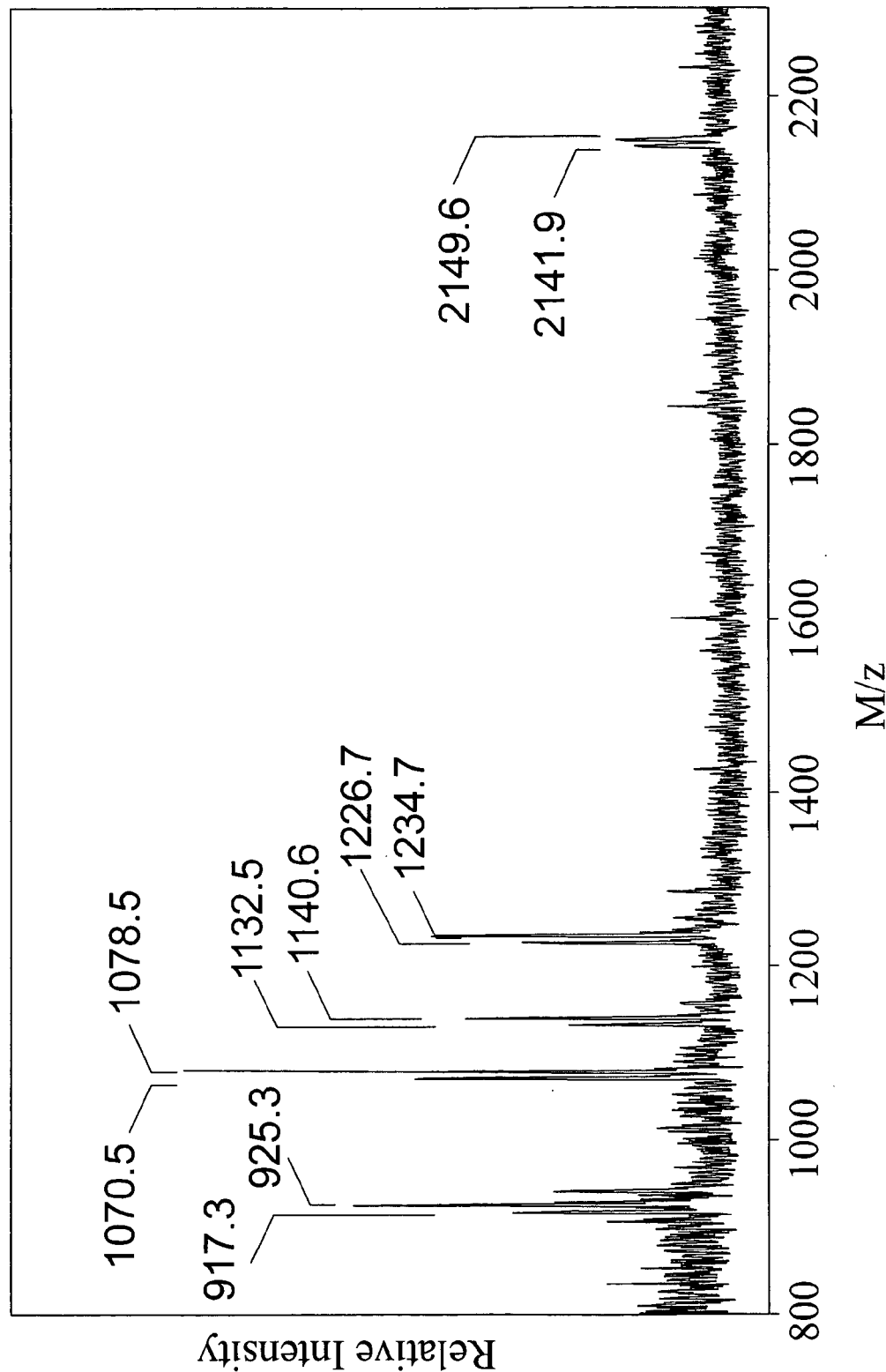
FIG. 24 shows MALDI-TOF mass spectra obtained from sample of chicken ovalbumin modified with light (Lys(U-$^{12}$C$_6$,$^{14}$N$_2$)) and heavy (Lys(U-$^{13}$C$_6$,$^{15}$N$_2$)) versions of PC-ICAT reagent (α-Maleimidopropyloxy-, ε-PC-Biotin-Lys-OH), mixed at 1:1 ratio, digested with trypsin and purified using affinity capture and photorelease from streptavidin agarose. Five sets of isotopically labeled peaks separated by 8 Da are visible.

Results from another example utilizing chicken ovalbumin is shown in FIG. 24. As is evident from the forgoing, the present invention provides compounds and methods for the detection, isolation, quantification and characterization of peptides, peptide fragments and other biomolecules. Other embodiments and uses of the invention will be apparent to those skilled in the art from consideration of the specification and practice of the invention disclosed herein. It is intended that the specification and examples be considered exemplary only, with the true scope and spirit of the invention being indicated by the following claims.

The invention claimed is:

1. A photocleavable compound having the general formula:

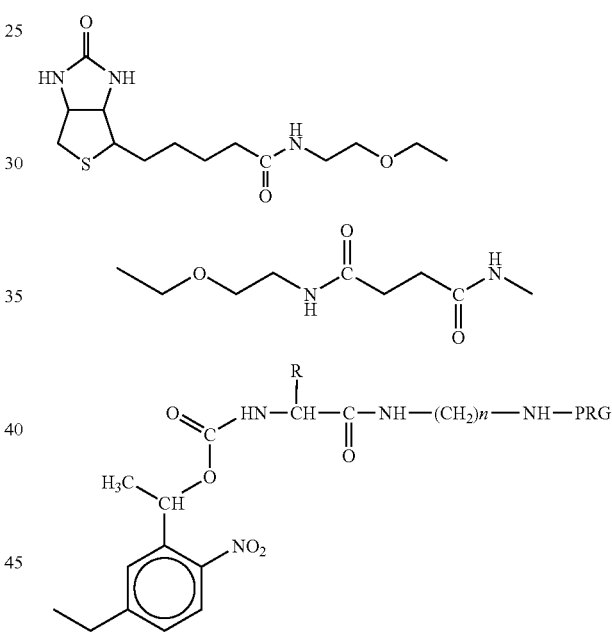

wherein R is an aliphatic hydrocarbon chain, wherein the aliphatic hydrocarbon chain is C1–C10 alkyl, linear or branched; wherein the portion defined by

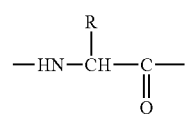

comprises one or more stable isotopes selected from the group consisting of $^2$H, $^{13}$C, and $^{15}$N; and PRG is a protein reactive group that reacts with functional groups on proteins.

2. The compound of claim 1, wherein said protein reactive group is a sulfhydryl reactive group or an amine reactive group.

3. A photocleavable compound having the general formula:

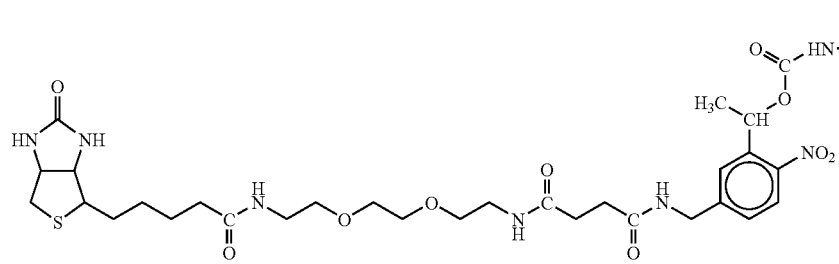
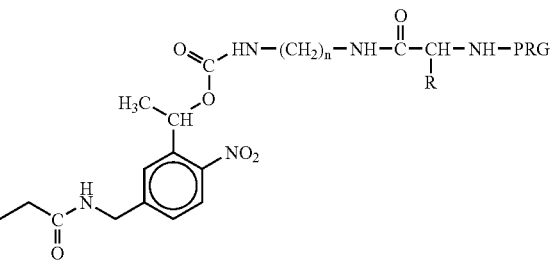

wherein R is an aliphatic hydrocarbon chain, wherein the aliphatic hydrocarbon chain is C1–C10 alkyl, linear or branched; wherein the portion defined by

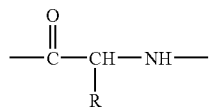

comprises one or more stable isotopes selected from the group consisting of $^2H$, $^{13}C$, and $^{15}N$; and PRG is a protein reactive group that reacts with functional groups on proteins.

4. The compound of claim 3, wherein said protein reactive group is a sulfhydryl reactive group or an amine reactive group.

5. A photocleavable compound having the general formula:

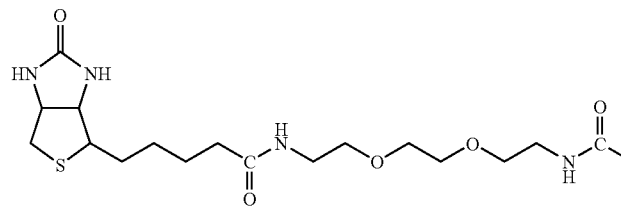
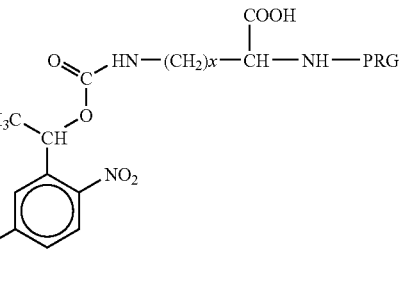

wherein x is a whole number between 1 and 10; wherein the portion defined by

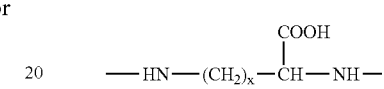

comprises one or more stable isotopes selected from the group consisting of $^2H$, $^{13}C$, and $^{15}N$; and PRG is a protein reactive group that reacts with functional groups on proteins.

6. The compound of claim 5, wherein said protein reactive group is a sulfhydryl reactive group or an amine reactive group.

7. A photocleavable compound having the general formula:

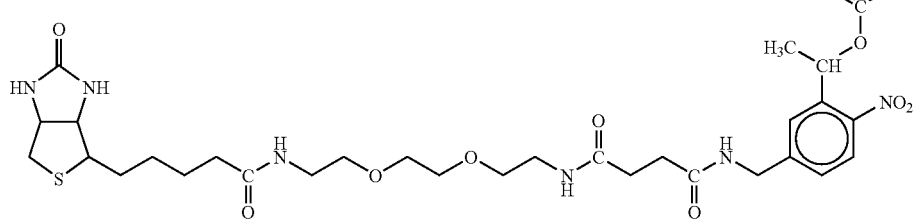

wherein x is a whole number between 1 and 10; wherein the portion defined by

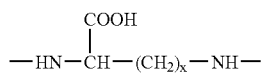

comprises one or more stable isotopes selected from the group consisting of $^2$H, $^{13}$C, and $^{15}$N; and PRG is a protein reactive group that reacts with functional groups on proteins.

8. The photocleavable compound of claim 2, wherein said protein reactive group is a malemide or iodocetamide.

9. The photocleavable compound of claim 4, wherein said protein reactive group is a malemide or iodocetamide.

10. The photocleavable compound of claim 6, wherein said protein reactive group is a malemide or iodocetamide.

11. The compound of claim 7, wherein said protein reactive group is a sulfhydryl reactive group or an amine reactive group.

12. The photocleavable compound of claim 11, wherein said protein reactive group is a malemide or iodocetamide.

* * * * *